(12) United States Patent
Anémian et al.

(10) Patent No.: US 8,906,893 B2
(45) Date of Patent: Dec. 9, 2014

(54) SUBSTITUTED TETRAARYLBENZENES

(75) Inventors: Rémi Manouk Anémian, Seoul (KR); Aurélie Ludemann, Frankfurt am Main (DE); Thomas Eberle, Landau (DE); Sigurd Hoeger, Bonn (DE); Eva Maria Reis, Breuberg (DE); Vanessa Bobbe, Bonn (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/991,919

(22) PCT Filed: Nov. 17, 2011

(86) PCT No.: PCT/EP2011/005810
§ 371 (c)(1),
(2), (4) Date: Jun. 6, 2013

(87) PCT Pub. No.: WO2012/079678
PCT Pub. Date: Jun. 21, 2012

(65) Prior Publication Data
US 2013/0261708 A1    Oct. 3, 2013

(30) Foreign Application Priority Data
Dec. 13, 2010 (DE) .......................... 10 2010 054 316

(51) Int. Cl.
| | | |
|---|---|---|
| C07D 251/00 | (2006.01) |
| H01L 51/00 | (2006.01) |
| C09B 3/78 | (2006.01) |
| C07C 15/38 | (2006.01) |
| C09K 11/06 | (2006.01) |
| A61N 5/06 | (2006.01) |
| C09B 3/02 | (2006.01) |
| C07C 13/62 | (2006.01) |
| C07D 251/24 | (2006.01) |
| C09B 57/00 | (2006.01) |
| C07C 15/28 | (2006.01) |
| C07C 225/22 | (2006.01) |
| C09B 1/00 | (2006.01) |
| C07C 13/567 | (2006.01) |
| H05B 33/14 | (2006.01) |
| C07C 15/30 | (2006.01) |
| C07C 211/61 | (2006.01) |
| H01L 51/50 | (2006.01) |

(52) U.S. Cl.
CPC .... *H01L 51/0058* (2013.01); *C09K 2211/1011* (2013.01); *C07C 2103/24* (2013.01); *C09K 2211/1088* (2013.01); *H01L 51/0067* (2013.01); *C07C 2103/26* (2013.01); *C09K 2211/1007* (2013.01); *C09B 3/78* (2013.01); *C07C 15/38* (2013.01); *C09K 11/06* (2013.01); *C07C 2103/54* (2013.01); *A61N 5/0613* (2013.01); *H01L 51/5012* (2013.01); *C09B 3/02* (2013.01); *C09K 2211/1059* (2013.01); *C07C 13/62* (2013.01); *H01L 51/0072* (2013.01); *C07D 251/24* (2013.01); *C09B 57/008* (2013.01); *C09B 57/00* (2013.01); *C07C 15/28* (2013.01); *H01L 51/0052* (2013.01); *C09K 2211/1044* (2013.01); *C07C 225/22* (2013.01); *C09B 1/00* (2013.01); *C07C 2103/42* (2013.01); *C09K 2211/1029* (2013.01); *H01L 51/005* (2013.01); *C07C 13/567* (2013.01); *H05B 33/14* (2013.01); *C07C 15/30* (2013.01); *C07C 211/61* (2013.01); *C09B 57/001* (2013.01); *Y02E 10/549* (2013.01); *C09B 57/007* (2013.01)
USPC .......................................................... 514/180

(58) Field of Classification Search
USPC ........................................................ 544/180
See application file for complete search history.

(56) References Cited

U.S. PATENT DOCUMENTS 5,858,771 A * 1/1999 Lee et al. ................ 435/320.1

FOREIGN PATENT DOCUMENTS

| JP | 2004014334 A | * | 1/2004 |
| JP | 2005302657 A | | 10/2005 |
| WO | WO-02/36641 A2 | | 5/2002 |
| WO | WO-2009054253 A1 | | 4/2009 |
| WO | WO-2011108902 A2 | | 9/2011 |

OTHER PUBLICATIONS

Hussain, Munawar, et al., "Synthesis of Aryl-Substituted Pyrimidines by Site-Selective Suzuki-Miyura Cross-Coupling Reactions of 2,4,5,6-Tetrachloropyrimidine", Adv. Synth. Catal., vol. 352, (2010), pp. 1429-1433.
Fujioka, Yasuhiro, et al., Synthesis and Spectral Characteristics of Seven Polyphenyls Containing Highly Branched *para*-Phenylene Ring(s), Chem. Pharma. Bull., vol. 33, No. 1, (1985), pp. 22-29.
Hintermann, Lukas, et al., "The Azaryphos Family of Ligands for Ambifunctional Catalysis: Synthesis and Use in Ruthenium-Catalyzed anti-Markovnikov Hydration of Terminal Alkynes", Chem. Eur. J., vol. 15, (2009), pp. 7167-7179.
Caplus Database, XP-002668186, (1969).
International Search Report for PCT/EP2011/005810 mailed Feb. 16, 2012.

* cited by examiner

*Primary Examiner* — Jeffrey H Murray
*Assistant Examiner* — Oluwafemi Masha
(74) *Attorney, Agent, or Firm* — Drinker Biddle & Reath LLP

(57) ABSTRACT

The present invention relates to substances, to electroluminescent device comprising these substances, and to the use thereof.

11 Claims, No Drawings

SUBSTITUTED TETRAARYLBENZENES

CROSS-REFERENCE TO RELATED APPLICATIONS

This application is a national stage application (under 35 U.S.C. §371) of PCT/EP2011/005810, filed Nov. 17, 2011, which claims benefit of German Application No. 10 2010 054 316.0, filed Dec. 13, 2010 which are both incorporated by reference.

The present invention relates to organic electroluminescent devices and to materials for use in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here, besides fluorescent emitters, are increasingly organometallic complexes which exhibit phosphorescence (M. A. Baldo et al., Appl. Phys. Lett. 1999, 75, 4-6). For quantum-mechanical reasons, an up to four-fold energy and power efficiency is possible using organometallic compounds as phosphorescence emitters. In general, there is still a need for improvement both in the case of OLEDs which exhibit singlet emission and also in the case of OLEDs which exhibit triplet emission, in particular with respect to efficiency, operating voltage and lifetime. This applies, in particular, to OLEDs which emit in the relatively short-wave region, i.e. green and in particular blue.

The properties of OLEDs are determined not only by the emitters employed. In particular, the other materials used, such as host and matrix materials, hole-blocking materials, electron-transport materials, hole-transport materials and electron- or exciton-blocking materials, are also of particular importance here. Improvements in these materials can thus also result in significant improvements in the OLED properties.

According to the prior art, ketones (for example in accordance with WO 2004/093207 or WO 2010/006680) or phosphine oxides (for example in accordance with WO 2005/003253), inter alia, are used as matrix materials for phosphorescent emitters. Further matrix materials in accordance with the prior art are represented by triazines (for example WO 2008/056746, EP 0906947, EP 0908787, EP 0906948).

For fluorescent OLEDs, it is mainly condensed aromatic compounds, in particular anthracene derivatives, that are used in accordance with the prior art as host materials, especially for blue-emitting electroluminescent devices, for example 9,10-bis(2-naphthyl)anthracene (U.S. Pat. No. 5,935,721). WO 03/095445 and CN 1362464 disclose 9,10-bis(1-naphthyl)anthracene derivatives for use in OLEDs. Further anthracene derivatives are disclosed in WO 01/076323, in WO 01/021729, in WO 2004/013073, in WO 2004/018588, in WO 2003/087023 or in WO 2004/018587. Host materials based on aryl-substituted pyrenes and chrysenes are disclosed in WO 2004/016575. Host materials based on benzanthracene derivatives are disclosed in WO 2008/145239. For high-quality applications, it is desirable to have improved host materials available.

However, there is still a need for improvement in the case of the use of these host and matrix materials as also in the case of other host and matrix materials, in particular with respect to the efficiency and lifetime of the device.

Although OLEDs based on small molecules (SMOLEDs) in some cases exhibit fairly good efficiencies, lifetimes and/or operating voltage, thermal vacuum vapour-deposition methods are necessary, which are restricted to a certain device size. For mass production and for larger displays, however, it is desirable to apply the organic materials from solution, for example by means of spin-coating or ink-jet processes, which additionally enable the production costs to be reduced. Light-emitting polymers, oligomers and/or dendrimers are usually used in order to process electroluminescent devices from solution. These compounds often exhibit good solubility in organic aromatic solvents and have good film-formation properties. A further possibility for improving processability consists in incorporating long alkyl chains into a molecule as solubility-promoting groups. Unfortunately, the devices processed from solution using polymers, oligomers and/or dendrimers or molecules having alkyl chains usually have worse performance than comparable small molecules with respect to efficiency, lifetime and operating voltage.

The object of the present invention is the provision of compounds which are suitable for use in a fluorescent or phosphorescent OLED, for example as host and/or matrix material or as hole-transport/electron-blocking material or exciton-blocking material or as electron-transport or hole-blocking material, and which result in good device properties on use in an OLED, and the provision of the corresponding electronic device.

A further object of the present invention consists in the provision of molecules which have improved solubility and can therefore be processed from solution in the production of a light-emitting device Still a further object of the present invention consists in the provision of molecules which are particularly suitable for producing light-emitting devices from the gas phase, i.e. providing molecules which can be applied particularly well by vapour deposition.

Surprisingly, it has been found that certain compounds described in greater detail below achieve these objects and result in good properties of the organic electroluminescent device, in particular with respect to the lifetime, efficiency and operating voltage. The present invention therefore relates to electronic devices, in particular organic electroluminescent devices, which comprise compounds of this type and to the corresponding preferred compounds.

The present invention relates to compounds of the general formula (1)

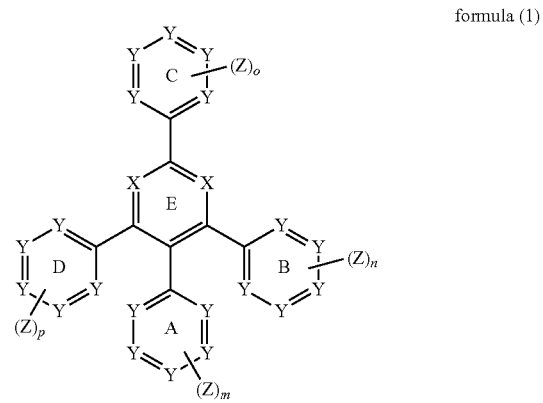

formula (1)

where the following applies to the symbols and indices used:
X is on each occurrence, identically or differently, CH or N;
Y is on each occurrence, identically or differently, $CR^1$, N, P or $PR^1_2$;

n is an integer from 0 to 5, where, if n is greater than or equal to 1, the n substituents Z are bonded to Y=CR$^1$ and in each case have replaced the radical R$^1$ here;

m is an integer from 0 to 5, where, if m is greater than or equal to 1, the m substituents Z are bonded to Y=CR$^1$ and in each case have replaced the radical R$^1$ here;

o is an integer from 0 to 5, where, if o is greater than or equal to 1, the o substituents Z are bonded to Y=CR$^1$ and in each case have replaced the radical R$^1$ here;

P is an integer from 0 to 5, where, if p is greater than or equal to 1, the p substituents Z are bonded to Y=CR$^1$ and in each case have replaced the radical R$^1$ here;

where the following condition must be satisfied: m+n+o+p=1, 2, 3 or 4;

and where at least one of the rings A, B, C or D must be substituted by a substituent Z in the meta position;

R$^1$ is, identically or differently on each occurrence, H, D, F, Cl, Br, I, N(R$^2$)$_2$, CN, NO$_2$, Si(R$^2$)$_3$, B(OR$^2$)$_2$, C(=O)R$^2$, P(=O)(R$^2$)$_2$, S(=O)R$^2$, S(=O)$_2$R$^2$, OSO$_2$R$^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals R$^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy, arylalkoxy or heteroaryloxy group having 5 to 60 aromatic ring atoms, which may be substituted by one or more radicals R$^2$, or a diarylamino group, diheteroarylamino group or arylheteroarylamino group having 10 to 40 aromatic ring atoms, which may be substituted by one or more radicals R$^2$, or a combination of two or more of these groups or a crosslinkable group Q;

R$^2$ is, identically or differently on each occurrence, H, D, F, Cl, Br, I, N(R$^3$)$_2$, CN, NO$_2$, Si(R$^3$)$_3$, B(OR$^3$)$_2$, C(=O)R$^3$, P(=O)(R$^3$)$_2$, S(=O)R$^3$, S(=O)$_2$R$^3$, OSO$_2$R$^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals R$^3$, where one or more non-adjacent CH$_2$ groups may be replaced by R$^3$C=CR$^3$, C≡C, Si(R$^3$)$_2$, Ge(R$^3$)$_2$, Sn(R$^3$)$_2$, C=O, C=S, C=Se, C=NR$^3$, P(=O)(R$^3$), SO, SO$_2$, NR$^3$, O, S or CONR$^3$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^3$, or an aryloxy, arylalkoxy or heteroaryloxy group having 5 to 60 aromatic ring atoms, which may be substituted by one or more radicals R$^3$, or a diarylamino group, diheteroarylamino group or arylheteroarylamino group having 10 to 40 aromatic ring atoms, which may be substituted by one or more radicals R$^3$, or a combination of two or more of these groups; two or more adjacent radicals R$^2$ here may form a mono- or polycyclic, aliphatic or aromatic ring system with one another;

R$^3$ is, identically or differently on each occurrence, H, D, F or an aliphatic, aromatic and/or heteroaromatic hydrocarbon radical having 1 to 20 C atoms, in which, in addition, one or more H atoms may be replaced by F; two or more substituents R$^3$ here may also form a mono- or polycyclic, aliphatic or aromatic ring system with one another;

Z is on each occurrence, identically or differently, R$^1$, with the proviso that at least one of the radicals Z must be an aromatic or heteroaromatic group having 5 to 60 aromatic ring atoms.

"Crosslinkable group" in the sense of the resent invention means a functional group which is capable of reacting irreversibly. A crosslinked material, which is insoluble, is thereby formed. The crosslinking can usually be supported by heat or by UV, microwave, X-ray or electron radiation. Due to the high stability of the polymer according to the invention, less by-product formation occurs during the crosslinking. In addition, the crosslinkable groups in the polymer according to the invention crosslink very easily, meaning that lower amounts of energy are necessary for the crosslinking (for example <200° C. in the case of thermal crosslinking).

Examples of crosslinkable groups Q are units which contain a double bond, a triple bond, a precursor which is capable of in-situ formation of a double or triple bond, or a heterocyclic addition-polymerisable radical. Preferred radicals Q include vinyl, alkenyl, preferably ethenyl and propenyl, C$_{4-20}$-cycloalkenyl, azide, oxirane, oxetane, di(hydrocarbyl) amino, cyanate ester, hydroxyl, glycidyl ether, C$_{1-10}$-alkyl acrylate, C$_{1-10}$-alkyl methacrylate, alkenyloxy, preferably ethenyloxy, perfluoroalkenyloxy, preferably perfluoroethenyloxy, alkynyl, preferably ethynyl, maleimide, tri(C$_{1-4}$)-alkylsiloxy and tri(C$_{1-4}$)-alkylsilyl. Particular preference is given to vinyl and alkenyl.

An aryl group in the sense of this invention contains 6 to 40 C atoms; a heteroaryl group in the sense of this invention contains 1 to 39 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (anellated) aryl or heteroaryl group, for example naphthalene, anthracene, phenanthrene, quinoline, isoquinoline, etc. Aromatic groups which are linked to one another by a single bond, such as, for example, biphenyl, are, by contrast, not referred to as aryl or heteroaryl group, but instead as aromatic ring system.

An aromatic ring system in the sense of this invention contains 6 to 60 C atoms in the ring system. A heteroaromatic ring system in the sense of this invention contains 1 to 59 C atoms and at least one heteroatom in the ring system, with the proviso that the sum of C atoms and heteroatoms is at least 5. The heteroatoms are preferably selected from N, O and/or S. For the purposes of this invention, an aromatic or heteroaromatic ring system is intended to be taken to mean a system which does not necessarily contain only aryl or heteroaryl groups, but instead in which, in addition, a plurality of aryl or heteroaryl groups may be linked by a non-aromatic unit, such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are interrupted, for example, by a short alkyl group. Furthermore, systems in which a plurality of aryl and/or heteroaryl groups are linked to one another by a single bond, such as, for example, biphenyl, terphenyl or bipyridine, are intended to be taken to be an aromatic or heteroaromatic ring system.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or CH$_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent CH$_2$ groups may be replaced by R$^1$C═CR$^1$, C≡C, Si(R$^1$)$_2$, Ge(R$^1$)$_2$, Sn(R$^1$)$_2$, C═O, C═S, C═Se, C═NR$^1$, P(═O)(R$^1$), SO, SO$_2$, NR$^1$, O, S or CONR$^1$; furthermore, one or more H atoms may also be replaced by D, F, Cl, Br, I, CN or NO$_2$, preferably F, Cl or CN, further preferably F or CN, particularly preferably CN.

An aromatic or heteroaromatic ring system having 5-60 aromatic ring atoms, which may also in each case be substituted by the above-mentioned radicals R$^1$ or a hydrocarbon radical and which may be linked to the aromatic or heteroaromatic ring system via any desired positions, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

A preferred embodiment of the present invention are compounds of the general formula (2)

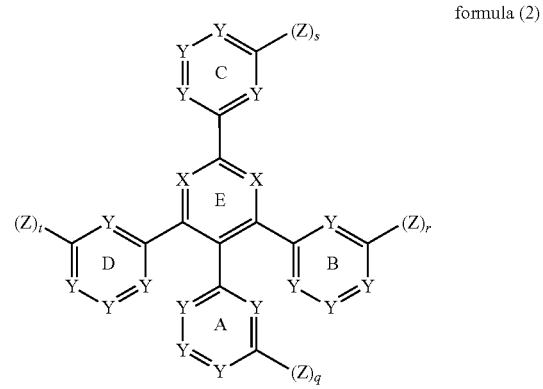

formula (2)

where the above definitions apply to the symbols and indices indicated; and
q, r, s, t is, independently of one another, either 0 or 1, where, u=q+r+s+t=1, 2, 3, 4.

Preference is furthermore given in the sense of the present invention to compounds of the formula (3)

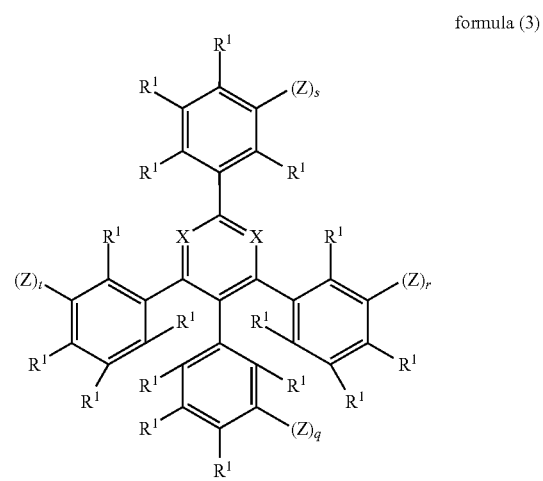

formula (3)

where the above definitions apply to the symbols and indices used.

Very preference is given in the sense of the present invention to compounds of the formula (4)

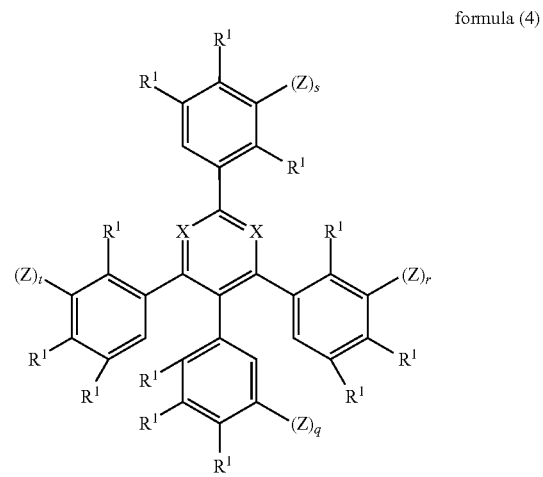

formula (4)

where the above definitions apply to the symbols and indices used.

Very particularly preferred compounds of the present invention are those of the formula (5)

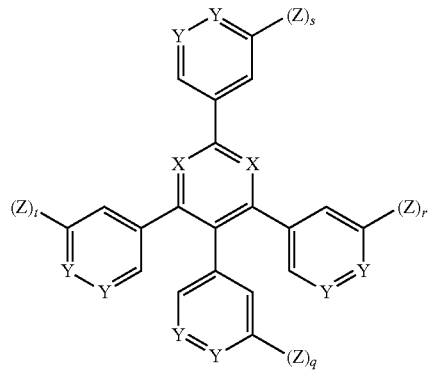

formula (5)

where the above definitions apply to the symbols and indices used.

Especially preferred compounds in the sense of the present invention are those of the general formula (6)

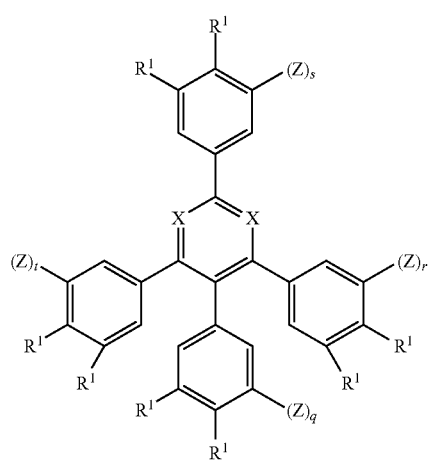

formula (6)

where the above definitions apply to the symbols and indices used.

In a furthermore preferred embodiment of the present invention, $u=q+r+s+t=3$.

Preferred embodiments of the present invention are therefore the compounds of the formula (7) to (9).

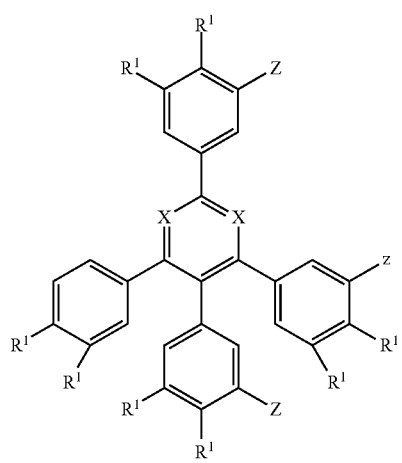

formula (7)

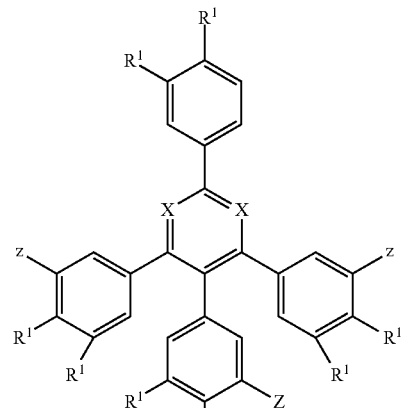

formula (8)

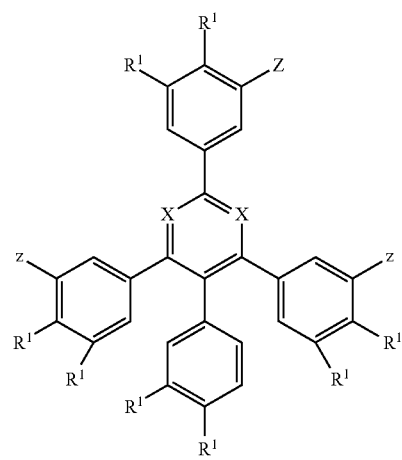

formula (9)

where the above definitions apply to the symbols and indices used.

Preference is furthermore given in the sense of the present invention to compounds of the formula (2) to (6) where $u=2$.

In a very preferred embodiment of the present invention, $u=1$ for the compounds of the formula (2) to (6). The compounds of the formula (10) to (12) represent very preferred embodiments of the present invention.

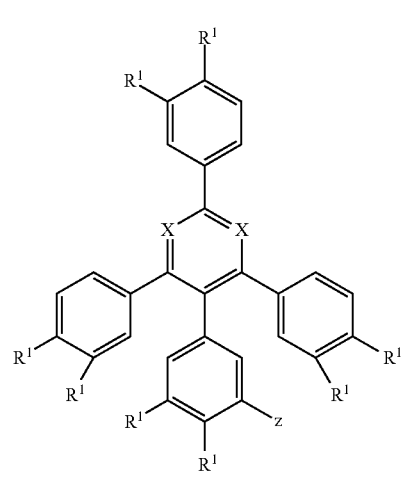

formula (10)

-continued formula (11)

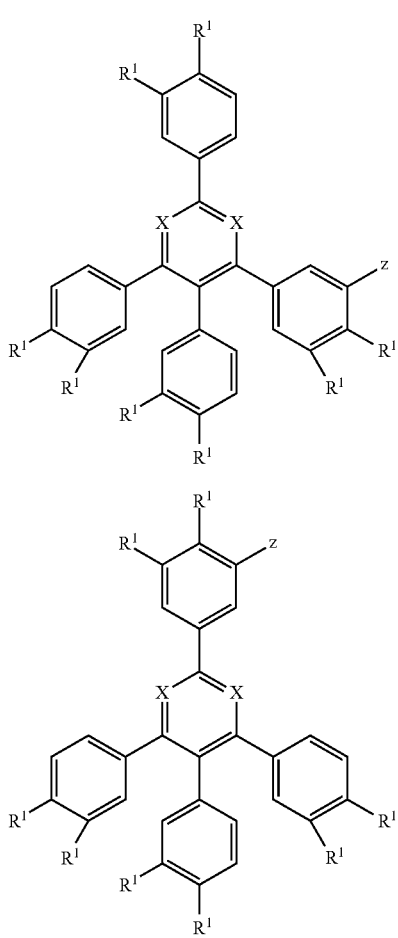

formula (12)

where the above definitions apply to the symbols and indices used.

In furthermore preferred embodiments of the present invention, X in the compounds having the formulae (1) to (12) is, identically on each occurrence, either CH or N.

It is very particularly preferred if X=N. Particularly preferred embodiments of the present invention are therefore the compounds of the formula (13).

formula (13)

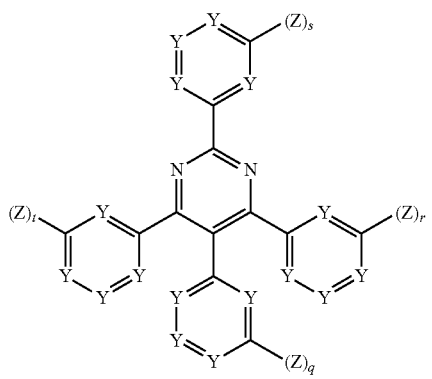

where the above definitions apply to the symbols and indices used.

Furthermore preferred embodiments of the present invention are the compounds of the formula (14)

formula (14)

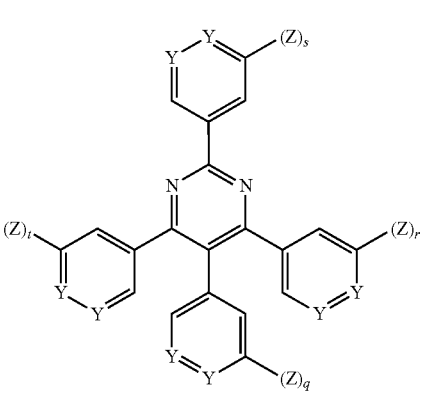

where the above definitions apply to the symbols and indices used.

Furthermore preferred embodiments of the present invention are the compounds of the formula (15)

formula (15)

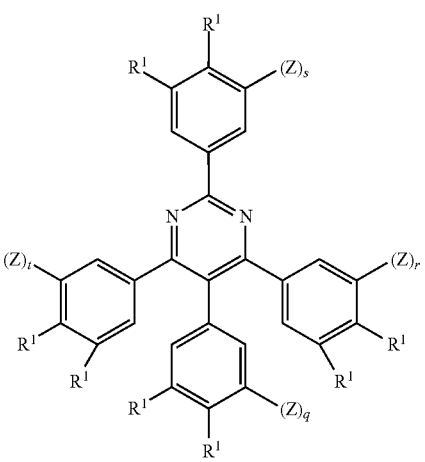

where the above definitions apply to the symbols and indices used.

In a very particularly preferred embodiment of the present invention, X=CH. Very particularly preferred compounds in the sense of the present invention are therefore compounds of the formula (16).

formula (16)

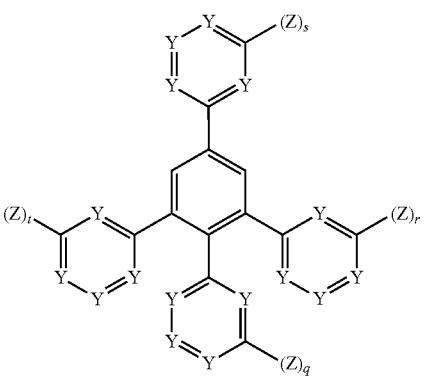

where the above definitions apply to the symbols and indices indicated.

Furthermore preferred compounds in the sense of the present invention are compounds of the formula (17).

formula (17)

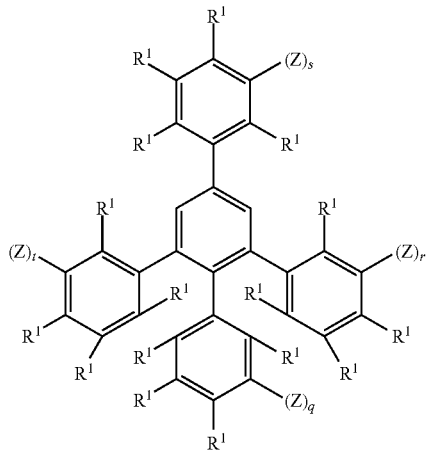

where the above definitions apply to the symbols and indices used.

Furthermore very preferred compounds in the sense of the present invention are compounds of the formula (18).

formula (18)

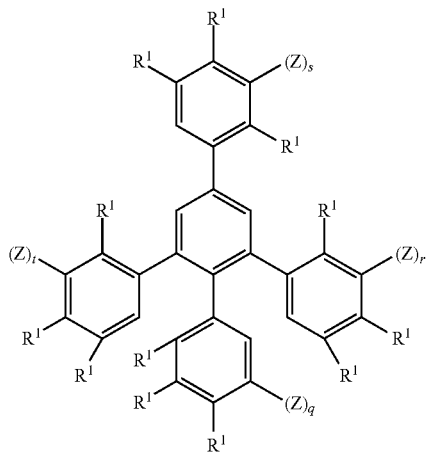

where the above definitions apply to the symbols and indices used.

Furthermore preferred embodiments of the present invention are the compounds of the formula (19)

formula (19)

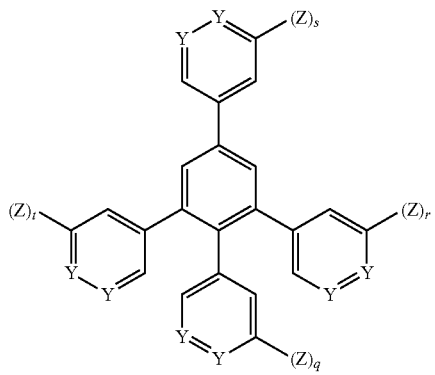

where the above definitions apply to the symbols and indices used.

Furthermore preferred embodiments of the present invention are the compounds of the formula (20)

formula (20)

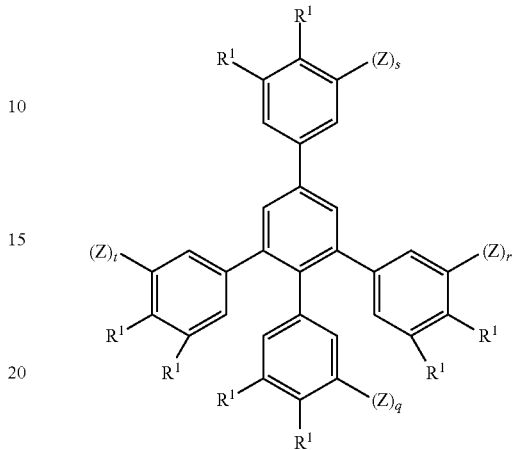

where the above definitions apply to the symbols and indices used.

In a furthermore preferred embodiment of the present invention, $u=q+r+s+t=3$.

Preferred embodiments of the present invention are therefore, in particular, the compounds having the formulae (21) to (23).

formula (21)

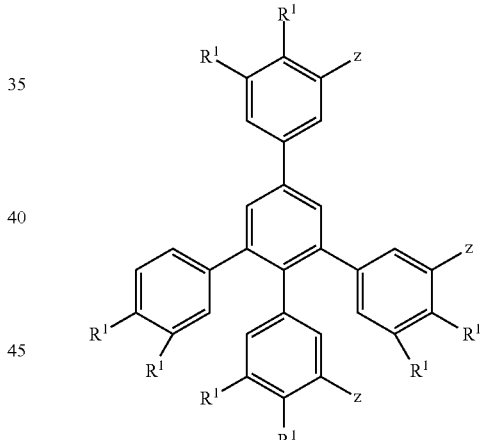

formula (22)

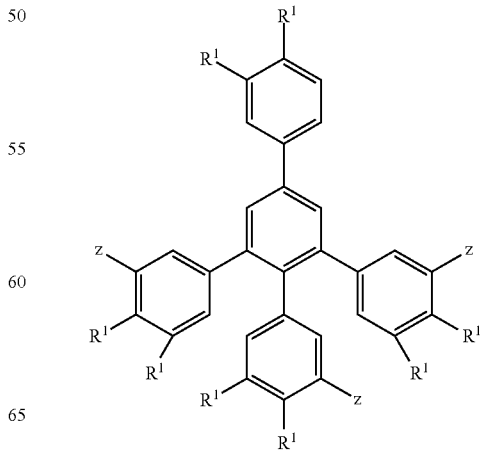

formula (23)

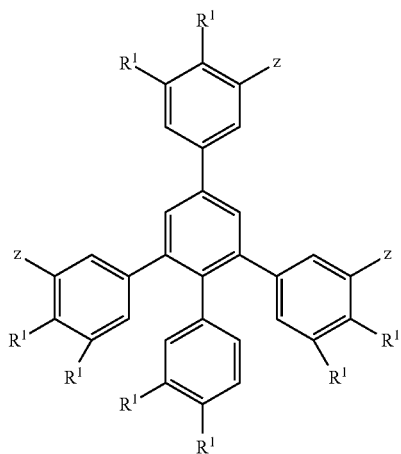

formula (26)

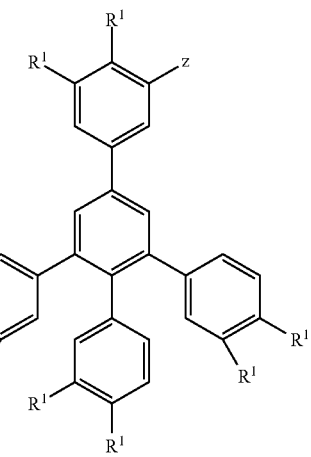

where the above definitions apply to the symbols used.

Preference is furthermore given in the sense of the present invention to compounds of the formula (17) to (20) where u=2.

In a very preferred embodiment of the present invention, u=1, i.e. the compounds of the formula (24) to (26) represent very preferred embodiments of the present invention.

where the above definitions apply to the symbols used.

A further preferred embodiment of the present invention relates to compounds of the formulae (1) to (26) which contain only one substituent Z, which is located on one of the rings A to D, but always in the meta position to the central ring E, and where X=CH and merely in each case a maximum of one Y on each ring A, B, C, D is equal to $CR^1$ (see formulae (27) to (29)).

formula (24)

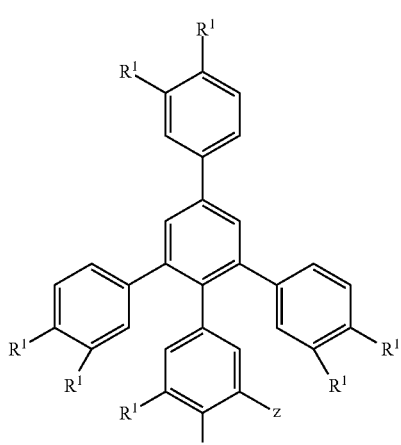

formula (27)

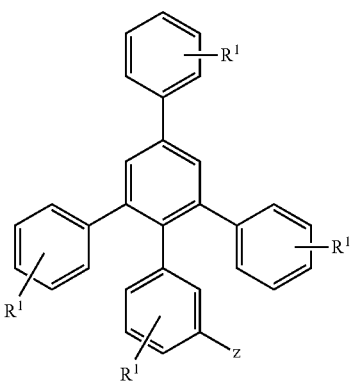

formula (25)

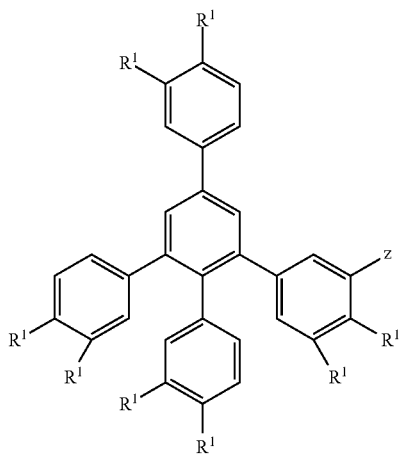

formula (28)

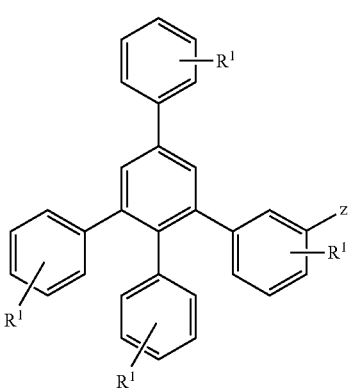

formula (29)

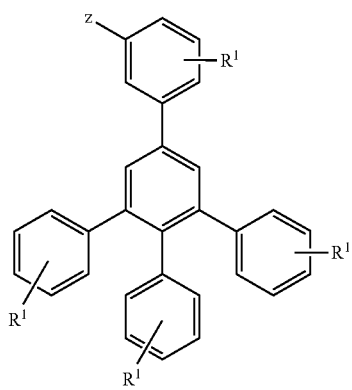

where the above definitions apply to the symbols used.

Furthermore preferred embodiments of the compounds (27) to (29) are those in which, besides the radical Z, only one radical $R^1$ occurs in the molecule, where the radical R may occur in any possible position of the rings A, B, C and D. Particular preference is given here to the compounds of the formula (30) to (62).

formula (30)

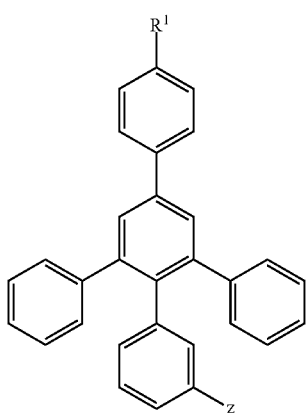

formula (31)

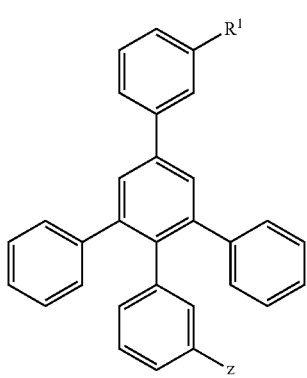

formula (32)

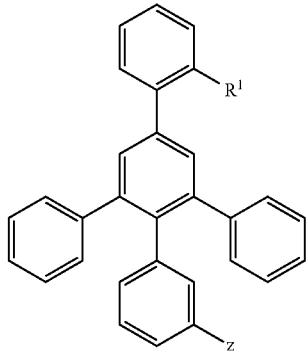

formula (33)

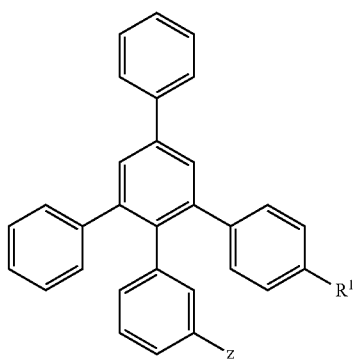

formula (34)

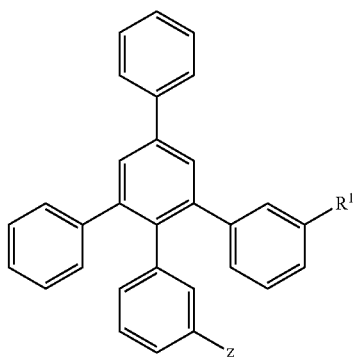

formula (35)

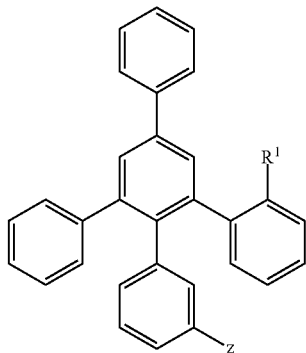

formula (36)
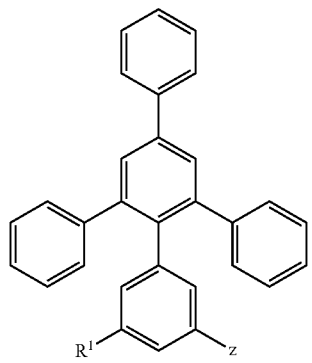
formula (37)
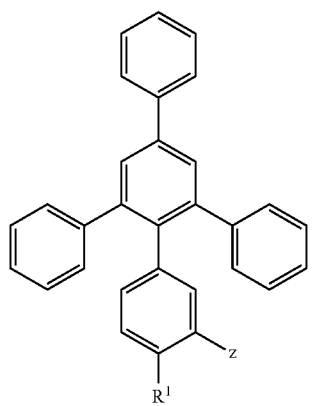
formula (38)
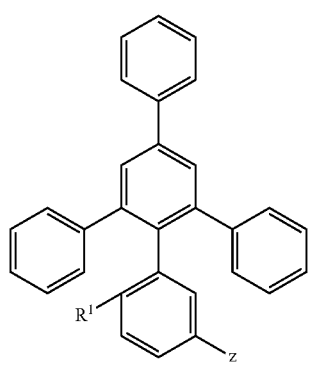
formula (39)
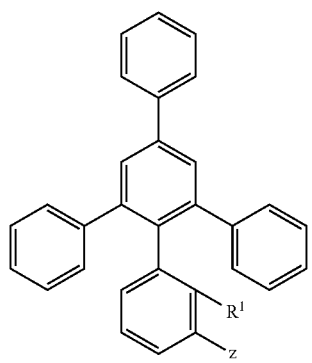
formula (40)
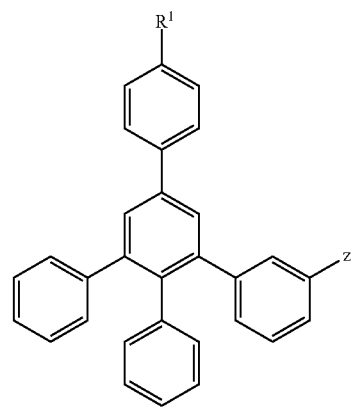
formula (41)
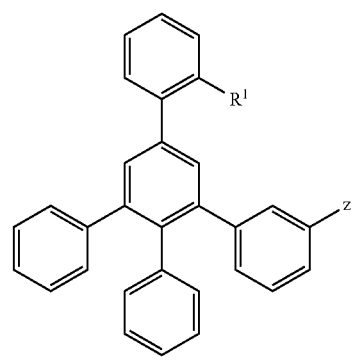
formula (42)
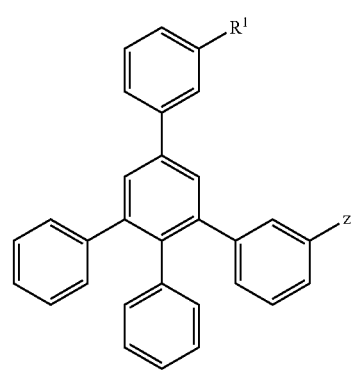
formula (43)
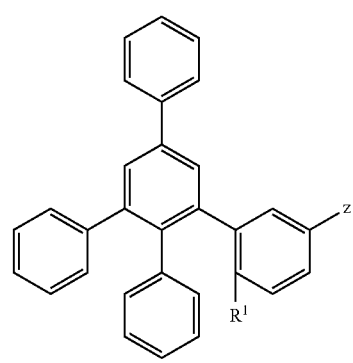

formula (44)
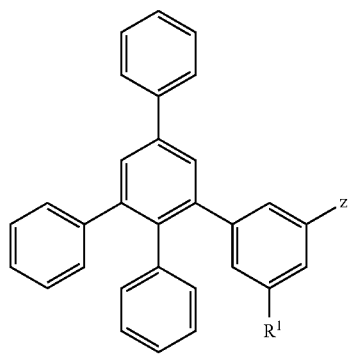
formula (45)
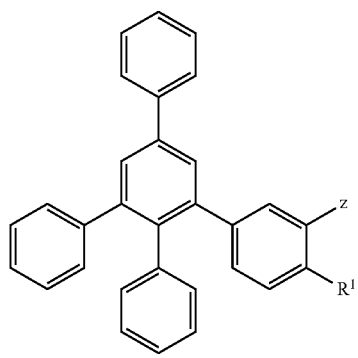
formula (46)
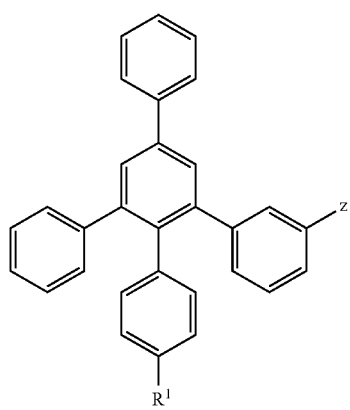
formula (47)
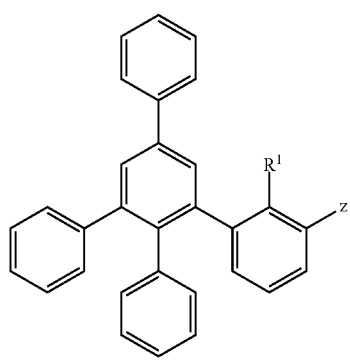
formula (48)
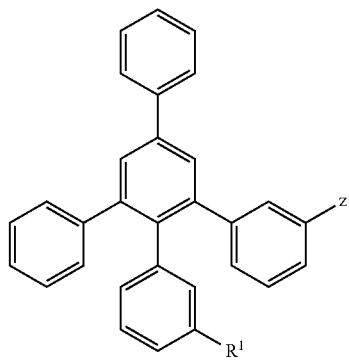
formula (49)
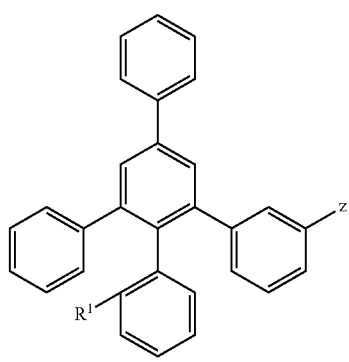
formula (50)
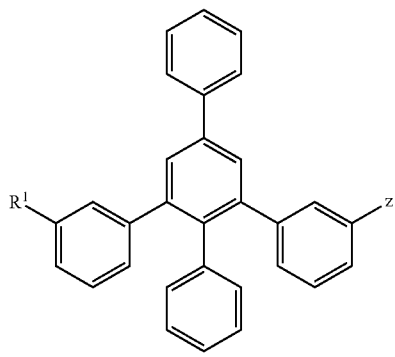
formula (51)
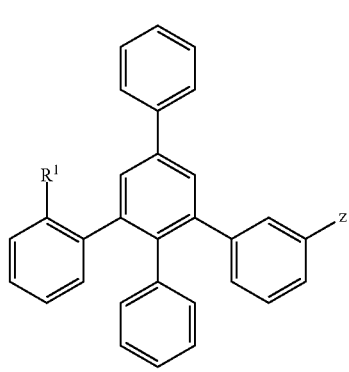

formula (52)
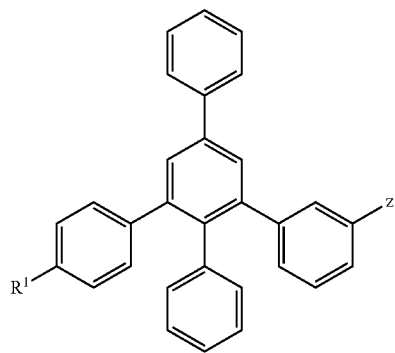
formula (53)
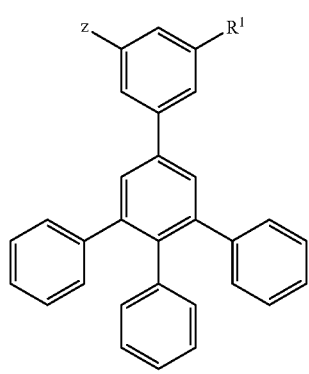
formula (54)
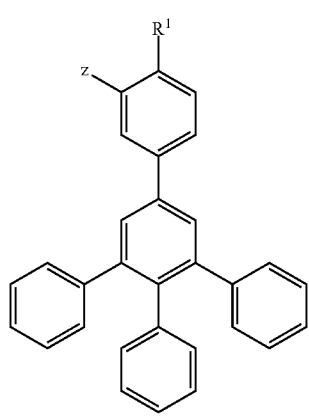
formula (55)
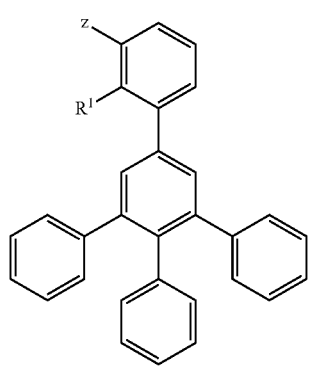
formula (56)
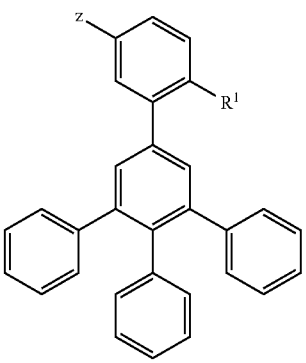
formula (57)
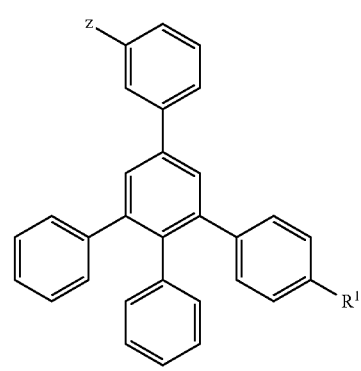
formula (58)
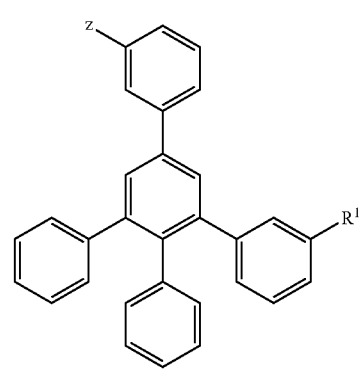
formula (59)
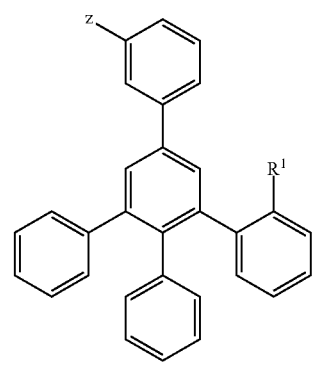

formula (60)

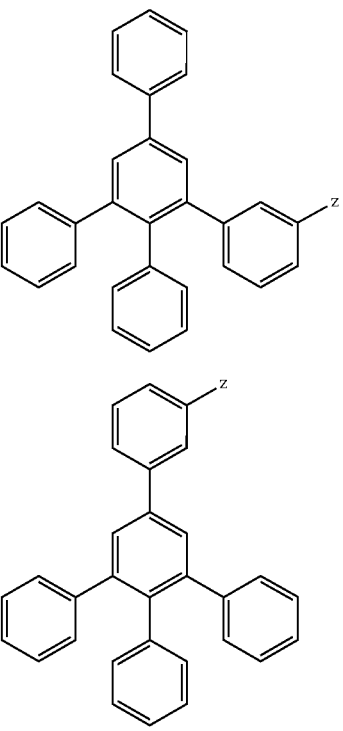

formula (64)

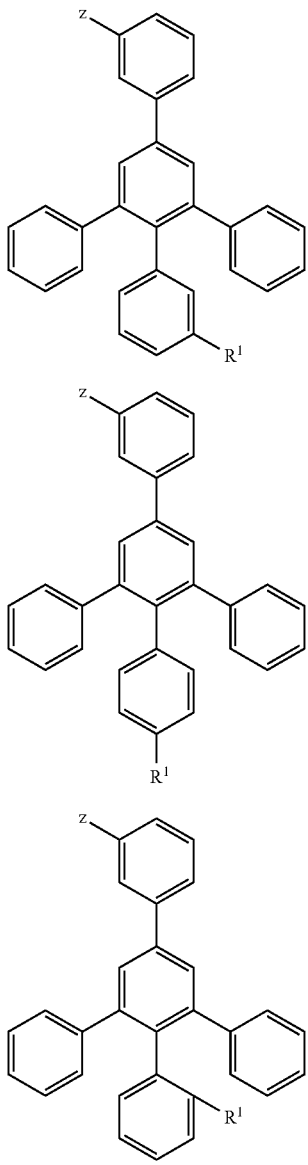

formula (61)

formula (65)

formula (62)

In a preferred embodiment of the present invention, Z is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^2$, where one or more non-adjacent $CH_2$ groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups, with the proviso that at least one of the radicals Z occurring must be an aromatic or heteroaromatic group having 5 to 60 aromatic ring atoms.

In an especially preferred embodiment of the present invention, the compound of the formula (1) contains only one substituent Z, which is located on one of the rings A to D, but always in the meta position to the central ring E, and where X═CH and Y═CR¹, where R¹═H (see formulae (63) to (65))

formula (63)

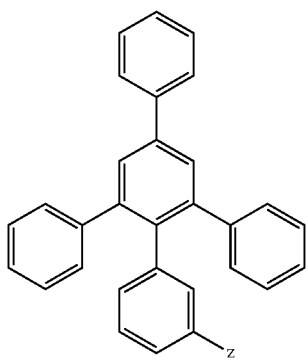

In a furthermore preferred embodiment of the present invention, Z in the compounds having the formulae (1) to (65) is, identically or differently on each occurrence, a straight-chain alkyl, alkoxy or thioalkoxy group having 1 to 20 C atoms or a straight-chain alkenyl or alkynyl group having 2 to 20 C atoms or a branched or cyclic alkyl, alkenyl, alkynyl, alkoxy, alkylalkoxy or thioalkoxy group having 3 to 20 C atoms, each of which may be substituted by one or more radicals $R^2$, where one or more non-adjacent $CH_2$ groups may be replaced by $R^2C=CR^2$, $C≡C$, $Si(R^2)_2$, $C=O$, $C=S$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an $Si(R^2)_3$ group, or an aromatic or heteroaromatic ring system having 5 to 60 aromatic ring atoms, which may in each case be substituted by one or more radicals $R^2$, or an arylketo, aryloxy, arylalkoxy, alkylaryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; at least one of the radicals Z occurring here must contain an aromatic or heteroaromatic group having 5 to 60 aromatic ring atoms, with the proviso that at least one of the radicals Z occurring must be an aromatic or heteroaromatic group having 5 to 60 aromatic ring atoms.

In a very preferred embodiment of the present invention, Z in the compounds having the formulae (1) to (65) is, identically or differently on each occurrence, a straight-chain alkyl or alkoxy group having 1 to 20 C atoms or a straight-chain alkenyl or alkynyl group having 2 to 20 C atoms or a branched or cyclic alkyl, alkenyl, alkynyl, alkoxy or alkylalkoxy group having 3 to 20 C atoms, each of which may be substituted by one or more radicals $R^2$, where one or more non-adjacent $CH_2$ groups may be replaced by $R^2C=CR^2$, $C≡C$, $Si(R^2)_2$, $C=O$, $C=S$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an $Si(R^2)_3$ group, or an aromatic or heteroaromatic ring system having 5 to 60 aromatic ring atoms, which may in each case be substituted by one or more radicals $R^2$, or an arylketo, aryloxy, arylalkoxy, alkylaryloxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups; at least one of the radicals Z occurring here must contain an aromatic or heteroaromatic group having 5 to 60 aromatic ring atoms, with the proviso that at least one of the radicals Z occurring must be an aromatic or heteroaromatic group having 5 to 60 aromatic ring atoms.

In a further very preferred embodiment of the present invention, at least one of the radicals Z occurring in the compounds having the formulae (1) to (65) is an aromatic or heteroaromatic group having 5 to 60 aromatic ring atoms, where the group of the aromatic and heteroaromatic groups having 5 to 60 ring atoms also include condensed aromatic and heteroaromatic ring systems.

If the compound of the formula (1) to (65) is used as matrix material for a phosphorescent electroluminescent device, Z is preferably selected from the group consisting of benzene, pyridine, pyrimidine, pyridazine, pyrazine, triazine, pyrrole, thiophene, furan, naphthalene, quinoline, isoquinoline, quinoxaline, indole, benzothiophene or benzofuran, each of which may be substituted by one or more radicals $R^1$. Particularly preferred groups Z are built up from in each case one or more groups benzene, pyridine, pyrimidine, pyridazine, pyrazine or triazine, each of which may be substituted by one or more radicals $R^1$, in particular benzene, which may be substituted by one or more radicals $R^1$. Further preferred groups Z for use as triplet matrix material are triphenylene, carbazole, indenocarbazole, indolocarbazole, each of which may be substituted by one or more radicals $R^1$. Likewise suitable are combinations of the aryl and heteroaryl groups mentioned as preferred. If the compound of the formula (1) to (65) is used in another function, for example as singlet host material and/or electron-transport material, preferred groups Z may also contain larger condensed aryl or heteroaryl groups, for example anthracene, pyrene or perylene, each of which may be substituted by one or more radicals $R^1$.

If the compounds of the formula (1) to (65) are employed as host materials for fluorescent emitters, Z is then preferably an anthracene, benzanthracene, pyrene, perylene, indenofluorene, fluorene, spirobifluorene, phenanthrene, dihydrophenanthrene, thiophene, imidazoles, each of which may be substituted by one or more radicals $R^1$.

In a particularly preferred embodiment of the invention, Z is selected from the group consisting of the units of the following formulae (66) to (80).

formula (66)

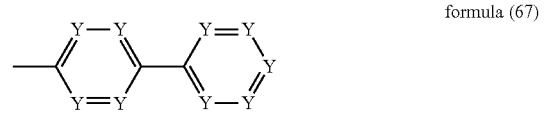

formula (67)

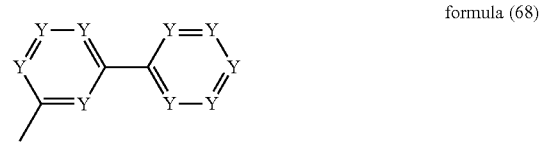

formula (68)

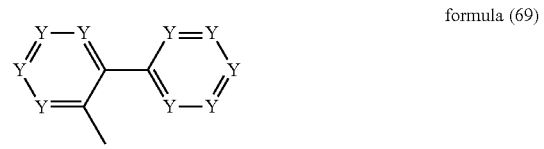

formula (69)

formula (70)

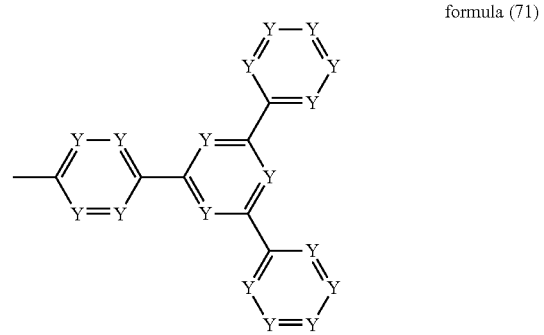

formula (71)

-continued formula (72)
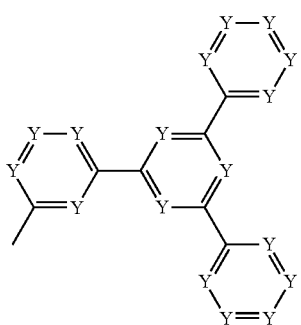

formula (73)
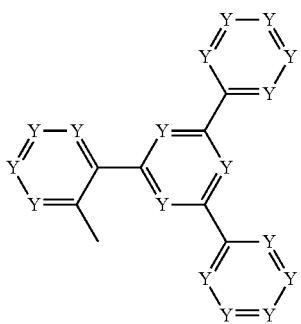

formula (74)
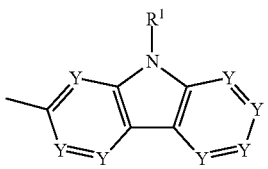

formula (75)
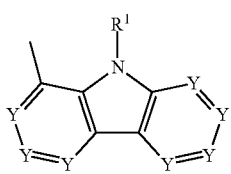

formula (76)
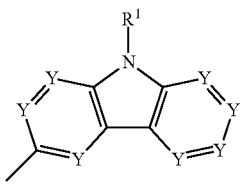

formula (77)
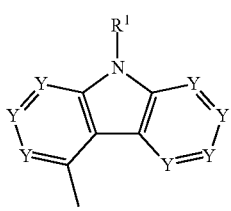

formula (78)
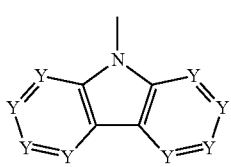

-continued formula (79)
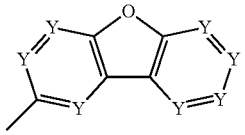

formula (80)
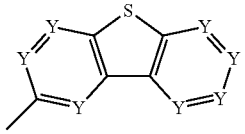

where the symbols used have the meanings given above.

In a preferred embodiment of the present invention, $R^1$ is, identically or differently on each occurrence, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^2$, where one or more non-adjacent $CH_2$ groups may be replaced by $R^2C=CR^2$, $C≡C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups.

It is furthermore preferred in the sense of the present invention for $R^1$ to be, identically or differently on each occurrence, H, D, F, Cl, Br, I, $N(R^2)_2$, CN, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which may be substituted by one or more radicals $R^2$, where one or more non-adjacent $CH_2$ groups may be replaced by $R^2C=CR^2$, $C≡C$, $Si(R^2)_2$, $Sn(R^2)_2$, $C=O$, $C=S$, $C=NR^2$, $P(=O)(R^2)$, $SO_2$, $NR^2$, O, S or $CONR^2$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$, or a combination of two or more of these groups.

If the compound of the formulae (1) to (65) is employed as triplet matrix material, in particular for emitters which emit green or blue light, and the radical $R^1$ stands for an aromatic or heteroaromatic ring system, it is preferred for the latter to contain no aryl groups having more than two condensed aryl rings. This preference can be explained by the low triplet level of aryl groups having more than two condensed aryl rings, making compounds of this type less suitable as triplet matrix material. The aromatic or heteroaromatic ring system particularly preferably contains no condensed aryl groups. Preferred aromatic or heteroaromatic ring systems $R^1$ for use as triplet matrix material are therefore built up from in each case one or more of the groups benzene, pyridine, pyrimidine, pyridazine, pyrazine, triazine, pyrrole, thiophene, furan, naphthalene, quinoline, isoquinoline, quinoxaline, indole, benzothiophene or benzofuran, each of which may be substituted by one or more radicals $R^2$. Particularly preferred groups Z are built up from in each case one or more groups benzene, pyridine, pyrimidine, pyridazine, pyrazine or triazine, each of which may be substituted by one or more radicals $R^2$, in particular benzene, which may be substituted by one or more radicals $R^2$. Further preferred groups $R^1$ for use as triplet matrix material are triphenylene and carbazole. Preference is likewise given to combinations of the aryl and heteroaryl groups mentioned as preferred. If the compound of the formula (1) is used in another function, for example as singlet host material and/or electron-transport material, preferred groups $R^1$ may also contain larger condensed aryl or heteroaryl groups, for example anthracene, pyrene or perylene, each of which may be substituted by one or more radicals $R^2$.

In a very particularly preferred embodiment of the present invention, at least one of the radicals Z occurring in the compounds having the is an aromatic or heteroaromatic group having 5 to 60 aromatic ring atoms, where the aromatic and heteroaromatic group merely includes naphthyl groups as condensed aromatic groups, but not other condensed aromatic and heteroaromatic groups.

In a very particularly preferred embodiment of the present invention, at least one of the radicals Z occurring in the compounds having the formula (1) to (65) is an aromatic or heteroaromatic group having 5 to 60 aromatic ring atoms, where condensed aromatic and heteroaromatic groups are not included.

In a very preferred embodiment of the present invention, the radical Z is selected from the formulae (81) to (289), where the formulae indicated may themselves be substituted by one or more radicals $R^3$, which may be identical or different on each occurrence and with the proviso that at least one of the radicals Z must be an aromatic or heteroaromatic group having 5 to 60 aromatic ring atoms.

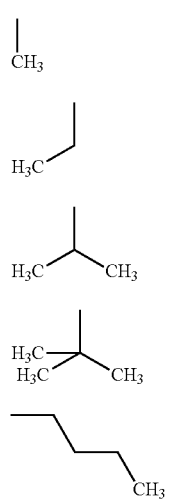

formula (81)

formula (82)

formula (83)

formula (84)

formula (85)

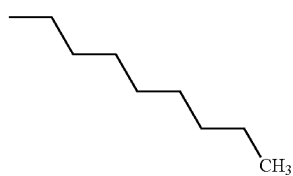

formula (86)

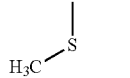

formula (87)

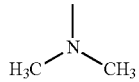

formula (88)

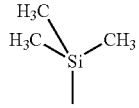

formula (89)

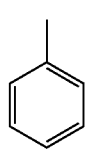

formula (90)

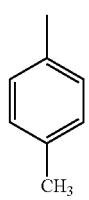

formula (91)

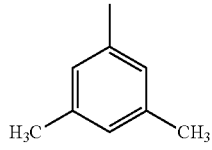

formula (92)

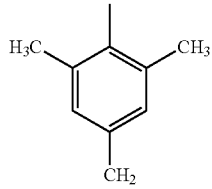

formula (93)

formula (94)

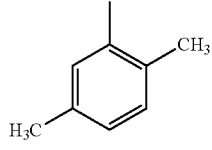

formula (95)

formula (96)
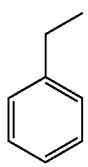
formula (97)
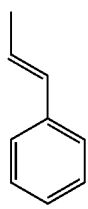
formula (98)
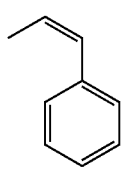
formula (99)
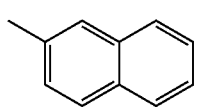
formula (100)
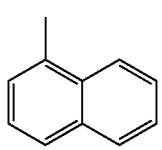
formula (101)
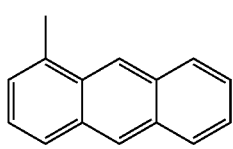
formula (102)
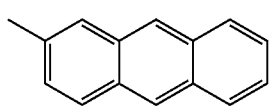
formula (103)
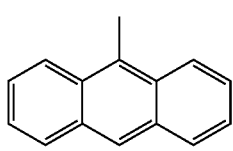
formula (104)
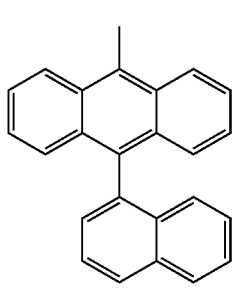
formula (105)
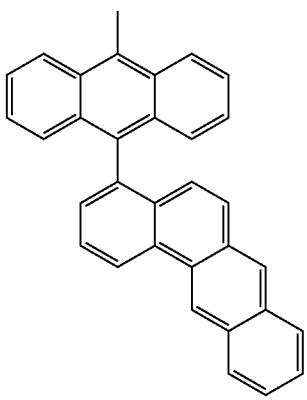
formula (106)
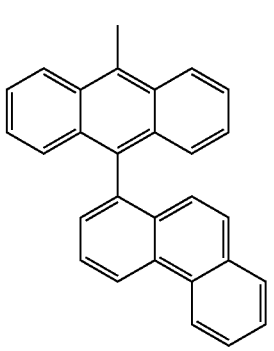
formula (107)
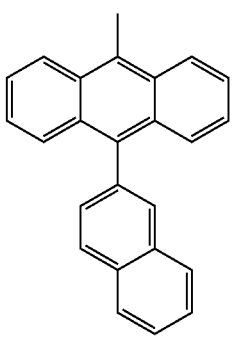
formula (108)
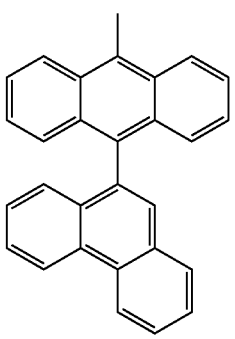

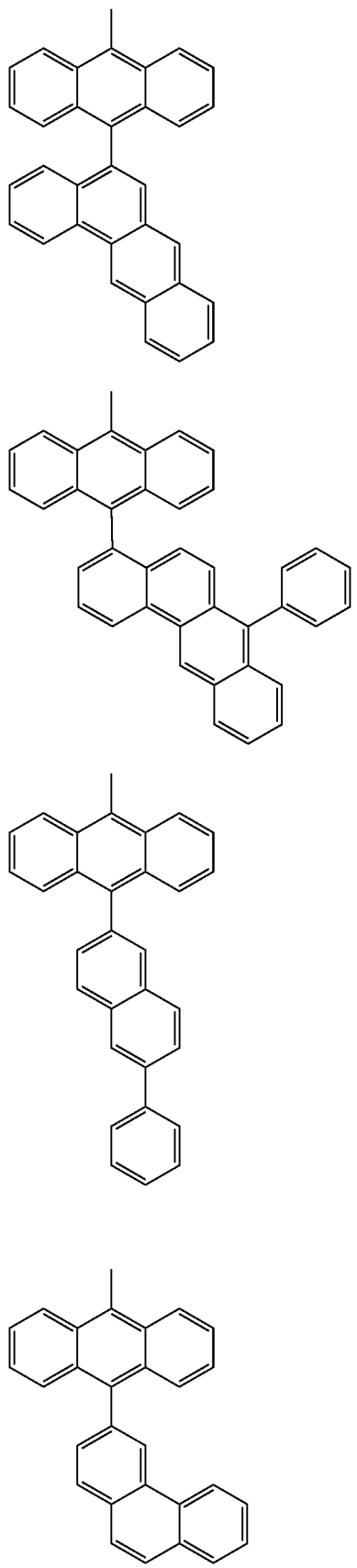
formula (109)
formula (110)
formula (111)
formula (112)
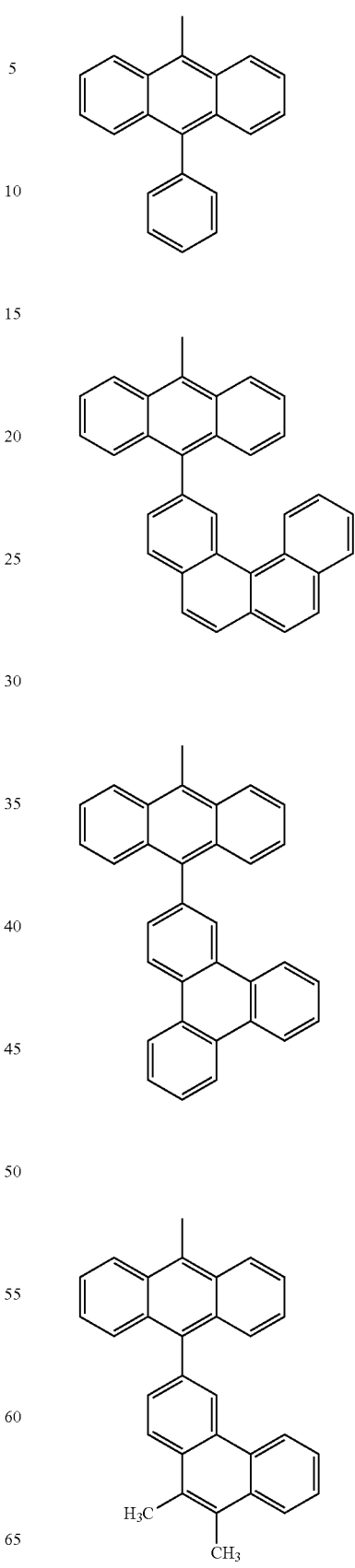
formula (113)
formula (114)
formula (115)
formula (116)

formula (117)
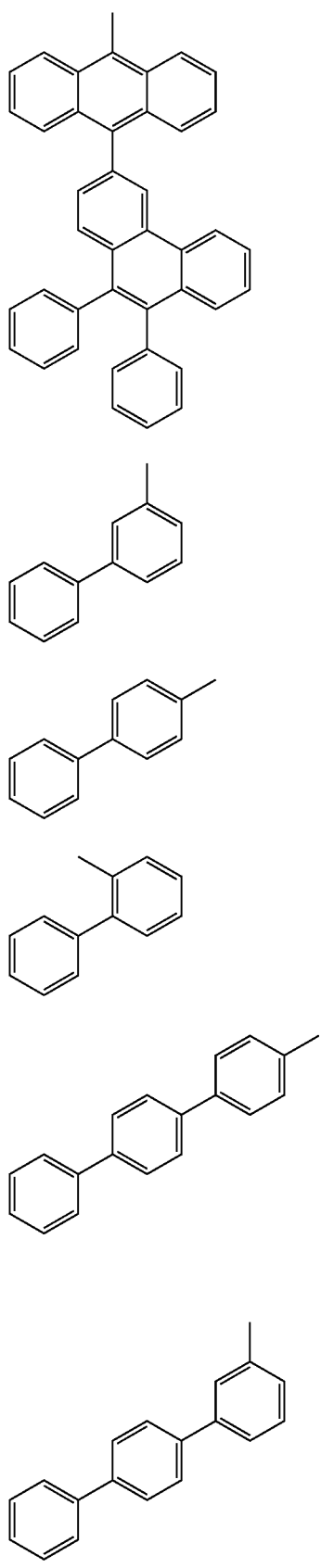
formula (118)
formula (119)
formula (120)
formula (121)
formula (122)
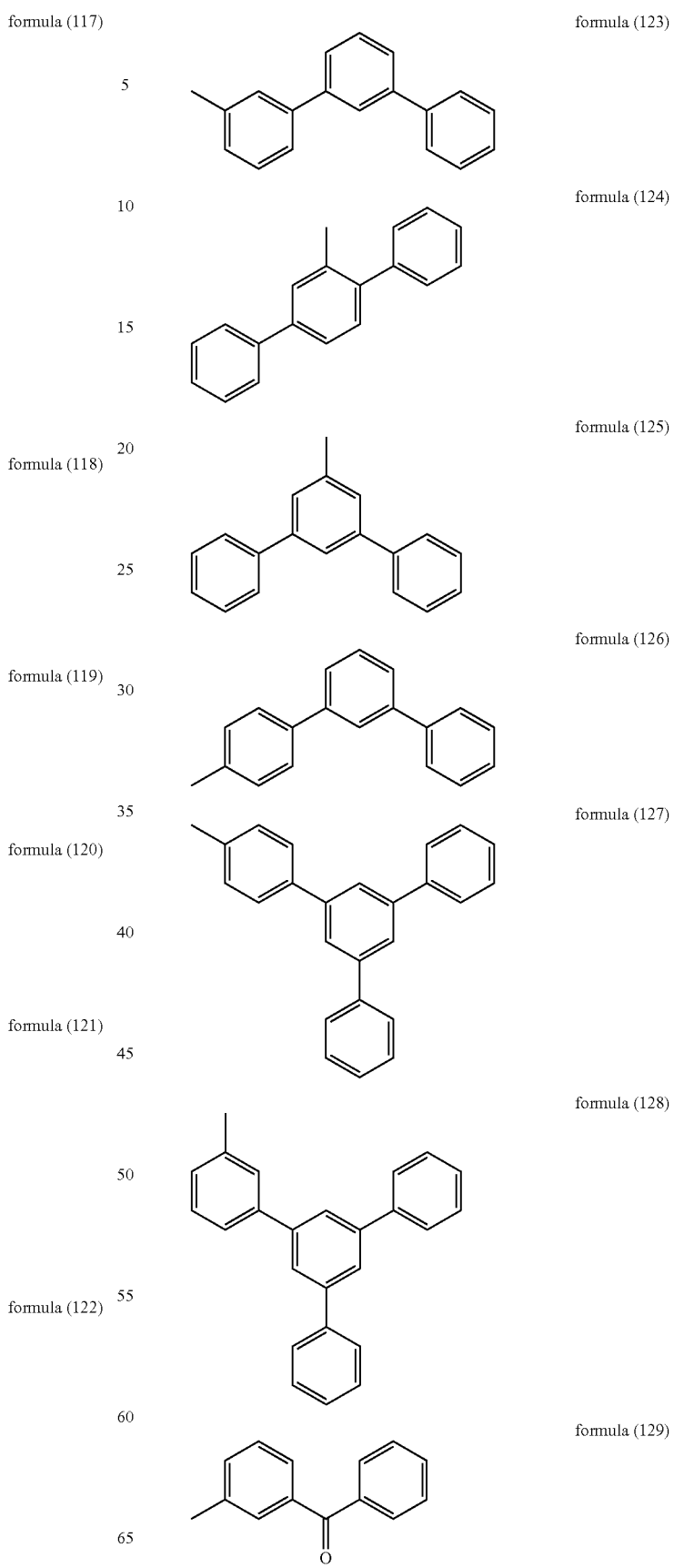
formula (123)
formula (124)
formula (125)
formula (126)
formula (127)
formula (128)
formula (129)

formula (130)

formula (131)

formula (132)

formula (133)

formula (134)

formula (135)

formula (136)

formula (137)

formula (138)

formula (139)

formula (140)

formula (141)

formula (142)
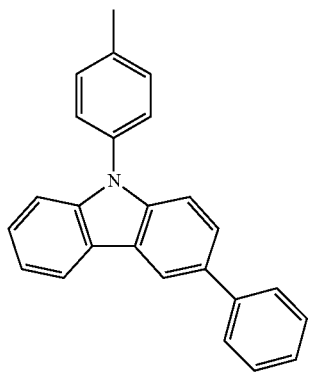
formula (143)
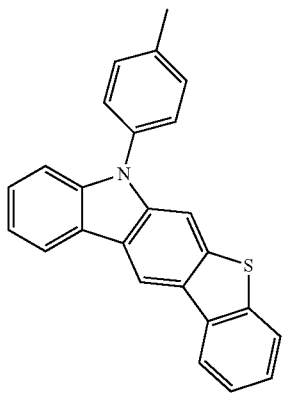
formula (144)
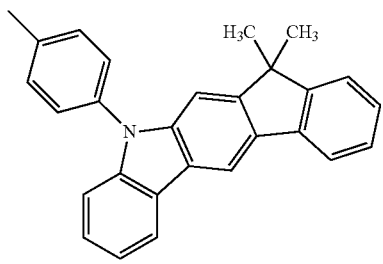
formula (145)
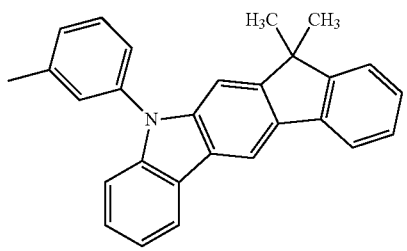
formula (146)
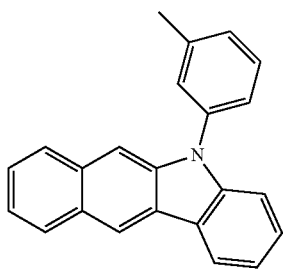
formula (147)
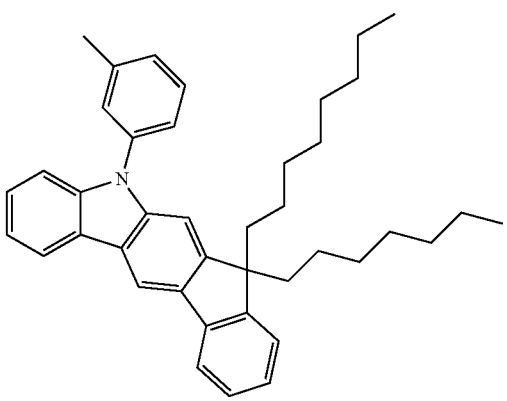
formula (148)
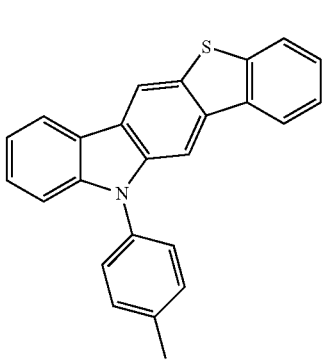
formula (149)
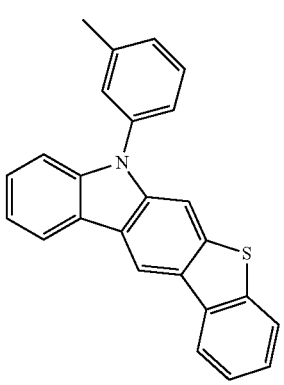
formula (150)
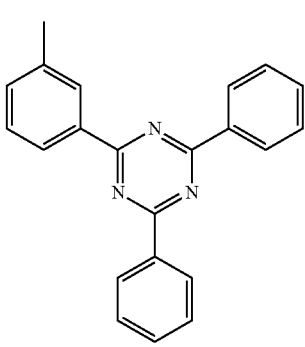

formula (151)
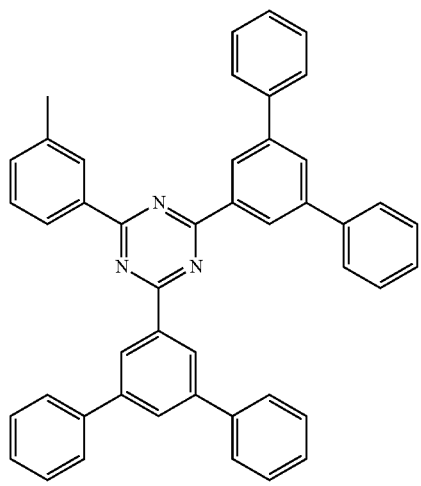
formula (152)
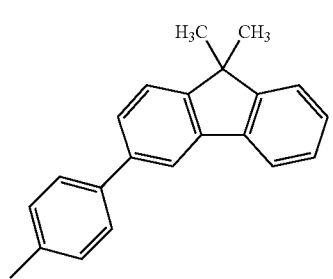
formula (153)
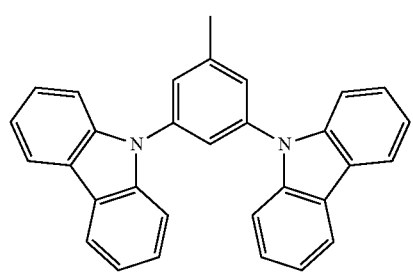
formula (154)
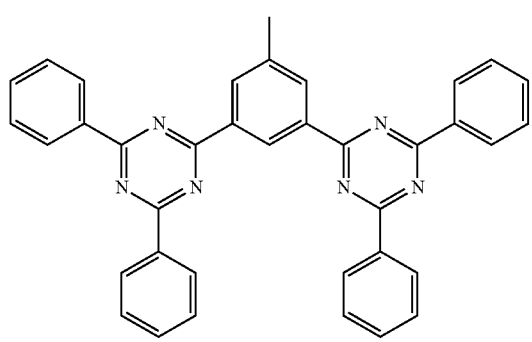
formula (155)
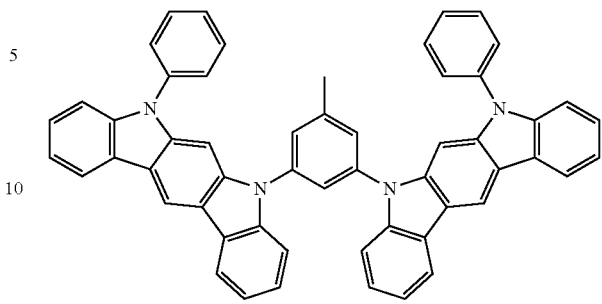
formula (156)
formula (157)
formula (158)
formula (159)
formula (160)
formula (161)
formula (162)
formula (163)
formula (164)
formula (165)

-continued
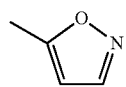
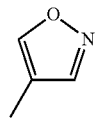
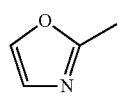
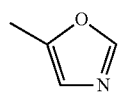
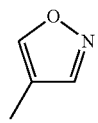
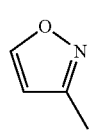
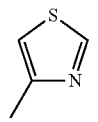
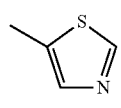
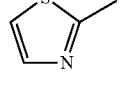
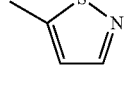
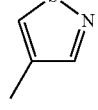
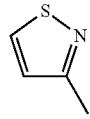
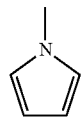
-continued
formula (166)
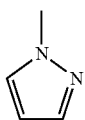
formula (167)
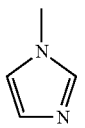
formula (168)
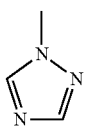
formula (169)
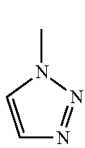
formula (170)
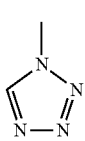
formula (171)
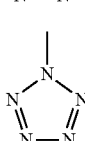
formula (172)
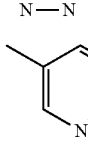
formula (173)
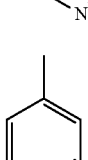
formula (174)
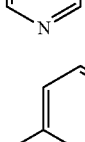
formula (175)
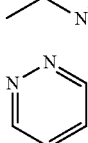
formula (176)
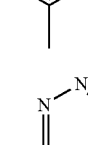
formula (177)
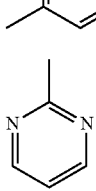
formula (178)
formula (179)
formula (180)
formula (181)
formula (182)
formula (183)
formula (184)
formula (185)
formula (186)
formula (187)
formula (188)
formula (189)
formula (190)

formula (191)
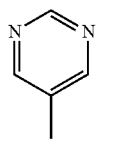
formula (192)
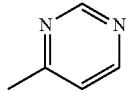
formula (193)
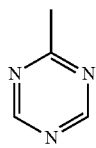
formula (194)
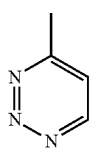
formula (195)
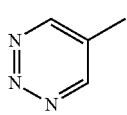
formula (196)
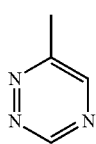
formula (197)
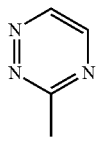
formula (198)
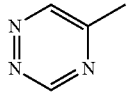
formula (199)
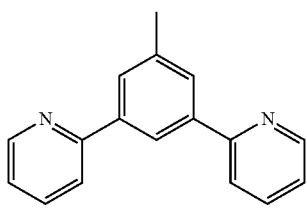
formula (200)
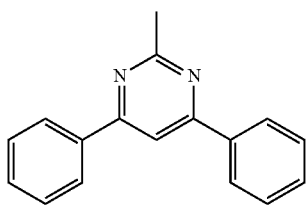
formula (201)
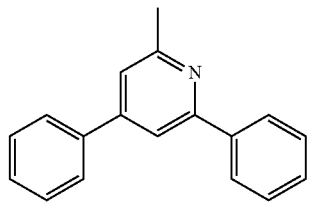
formula (202)
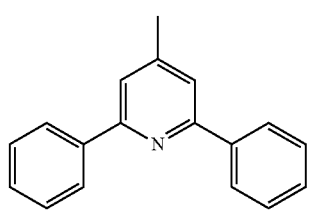
formula (203)
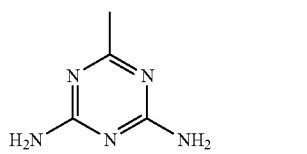
formula (204)
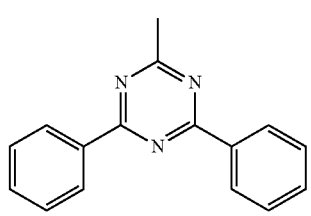
formula (205)
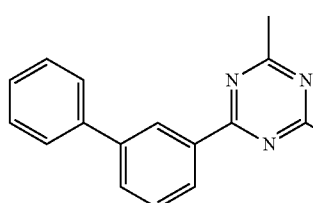
formula (206)
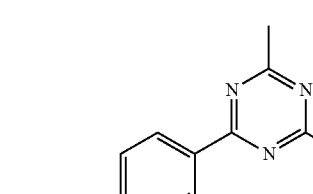

formula (207)
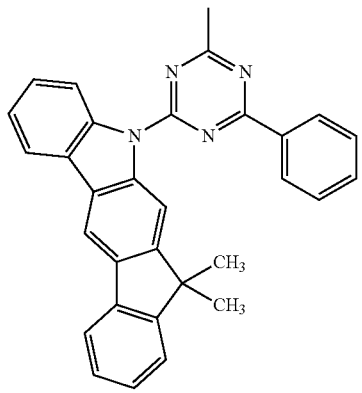
formula (208)
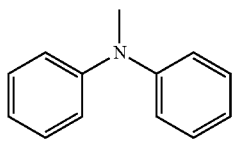
formula (209)
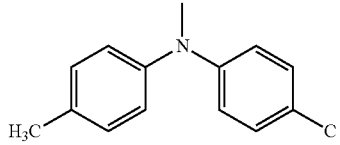
formula (210)
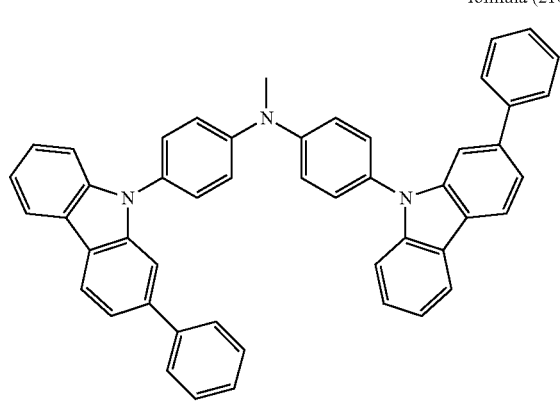
formula (211)
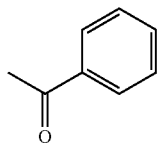
formula (212)
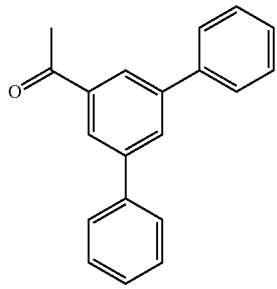
formula (213)
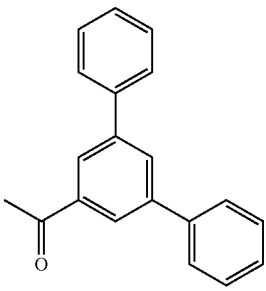
formula (214)
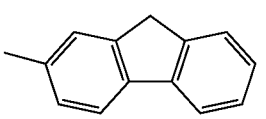
formula (215)
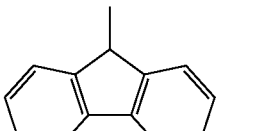
formula (216)
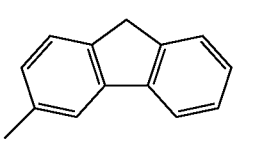
formula (217)
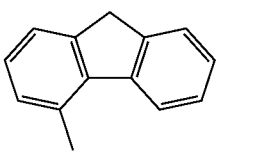
formula (218)
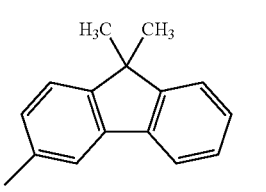
formula (219)
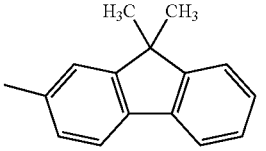
formula (220)
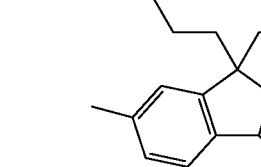

formula (221)
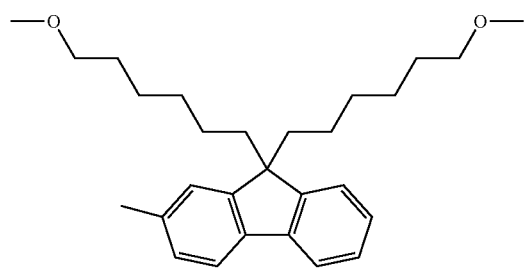
formula (222)
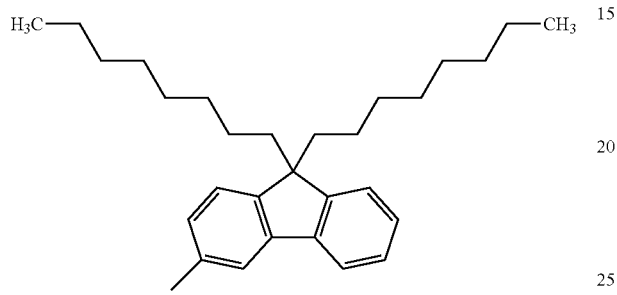
formula (223)
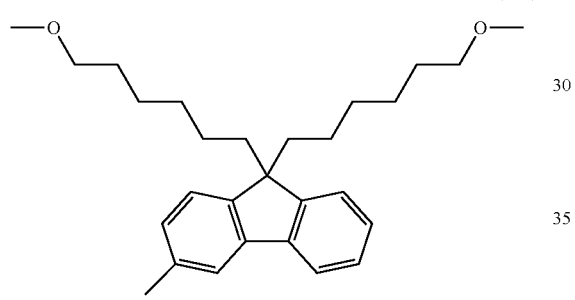
formula (224)
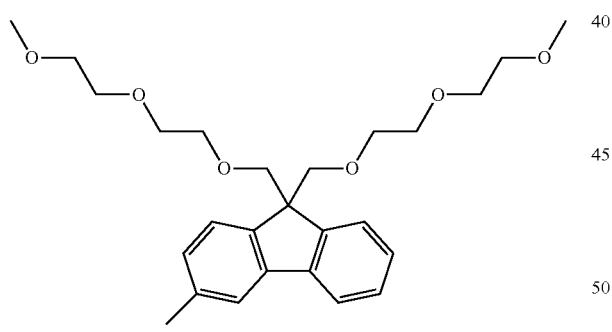
formula (225)
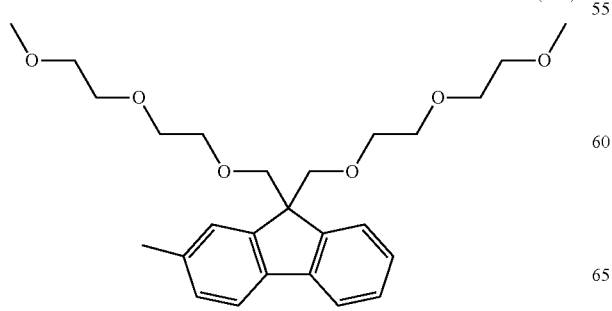
formula (226)
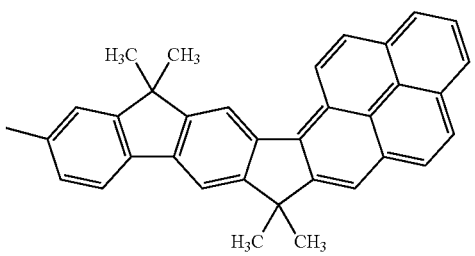
formula (227)
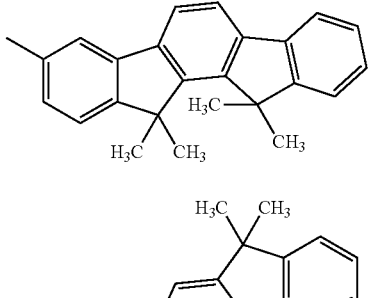
formula (228)
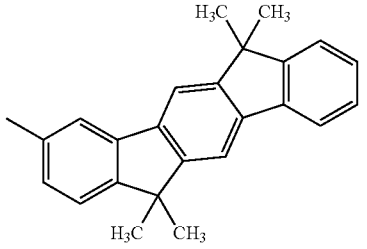
formula (229)
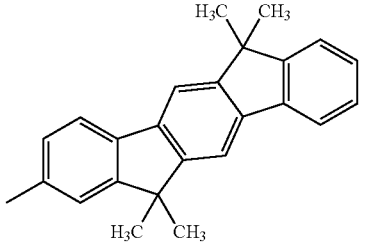
formula (230)
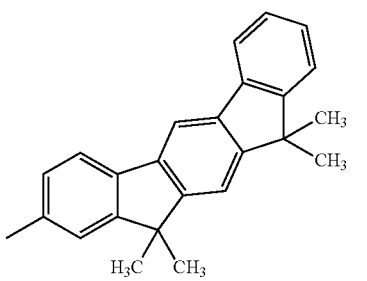
formula (231)
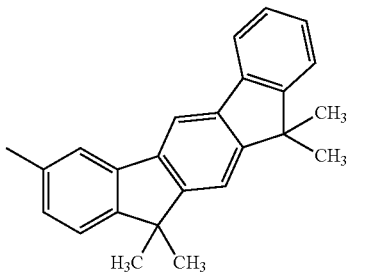

formula (232)
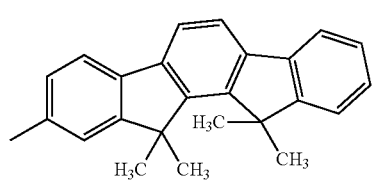
formula (233)
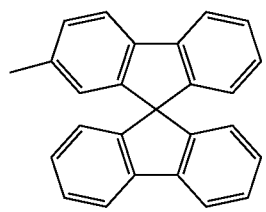
formula (234)
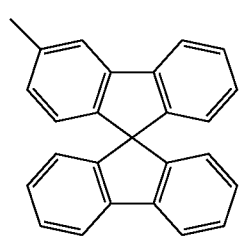
formula (235)
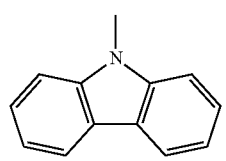
formula (236)
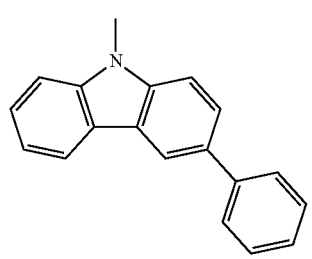
formula (237)
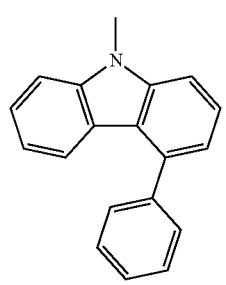
formula (238)
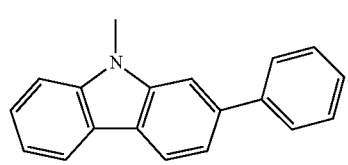
formula (239)
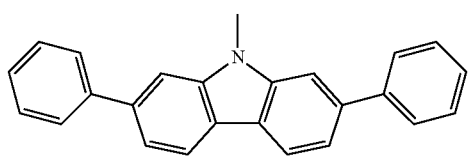
formula (240)
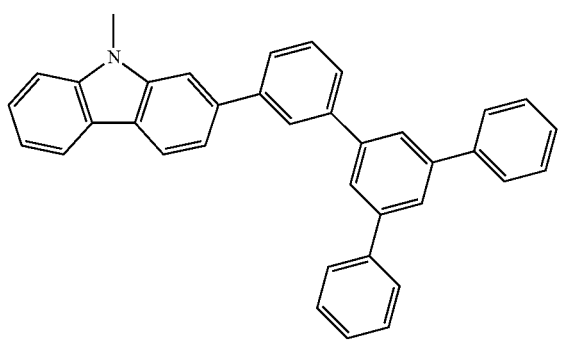
formula (241)
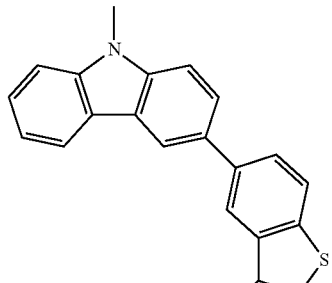
formula (242)
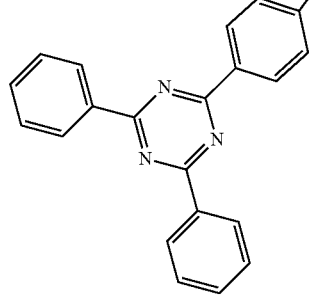
formula (243)
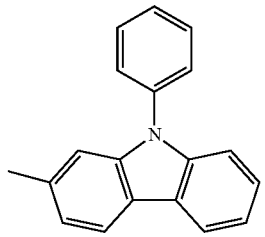

formula (244)
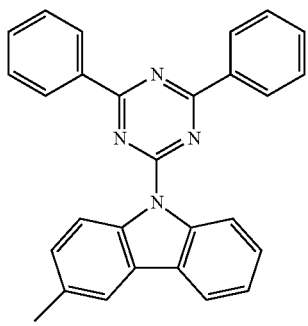
formula (245)
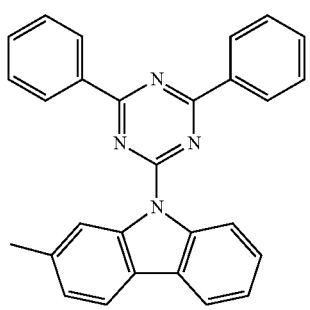
formula (246)
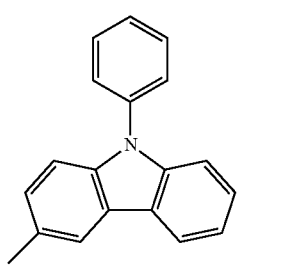
formula (247)
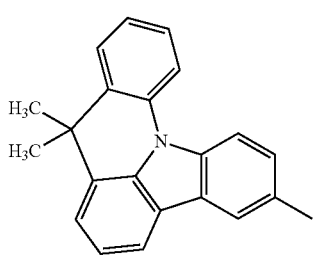
formula (248)
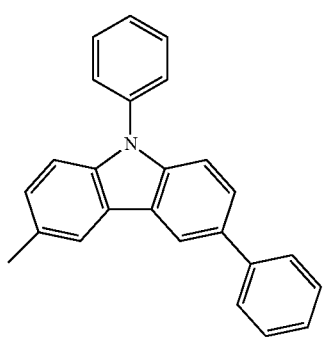
formula (249)
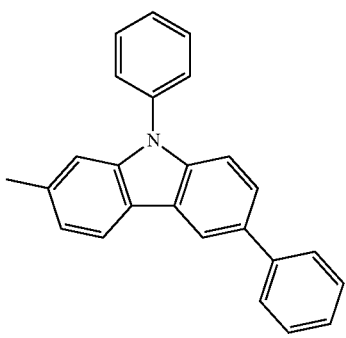
formula (250)
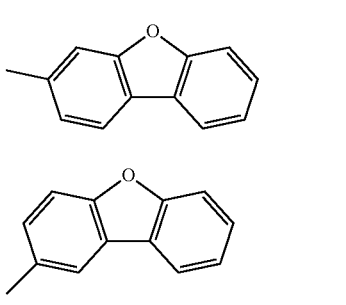
formula (251)
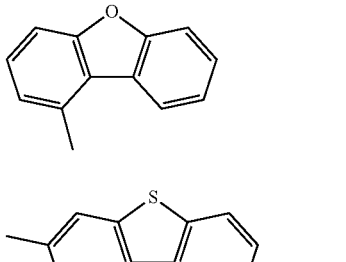
formula (252)
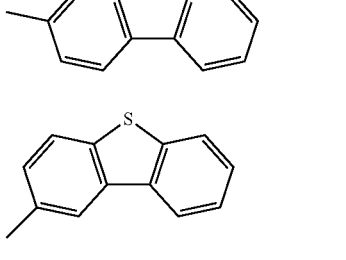
formula (253)
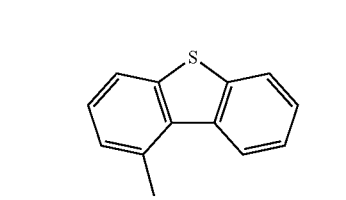
formula (254)
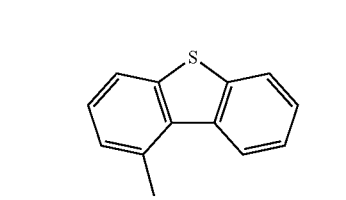
formula (255)
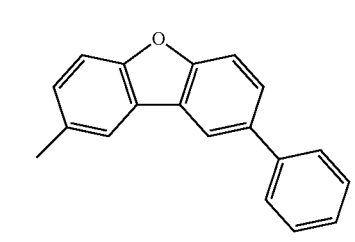
formula (256)
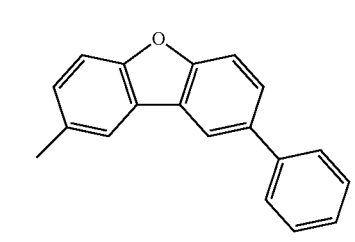

formula (257)
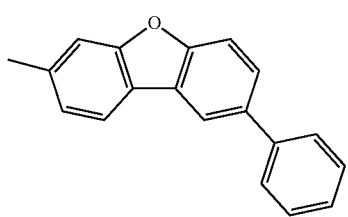
formula (258)
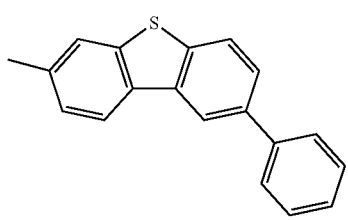
formula (259)
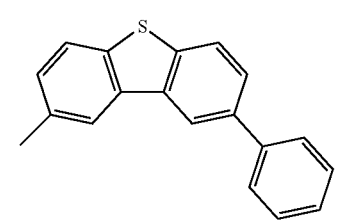
formula (260)
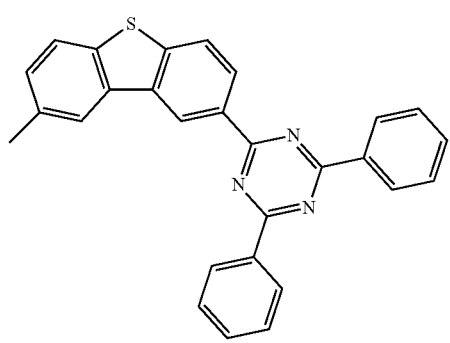
formula (261)
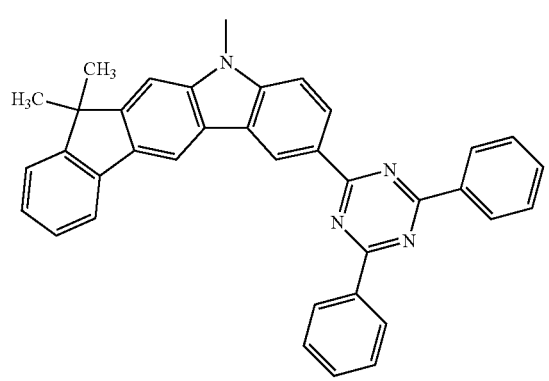
formula (262)
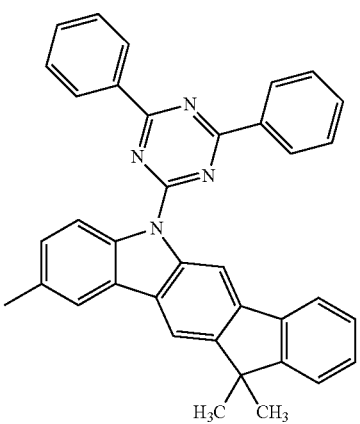
formula (263)
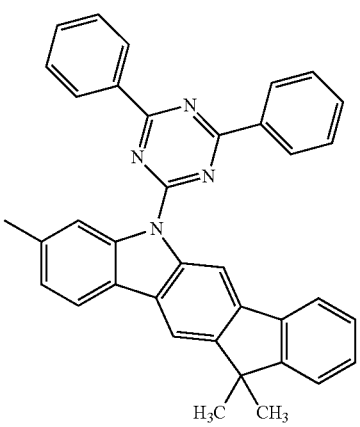
formula (264)
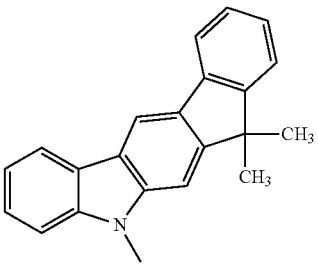
formula (265)
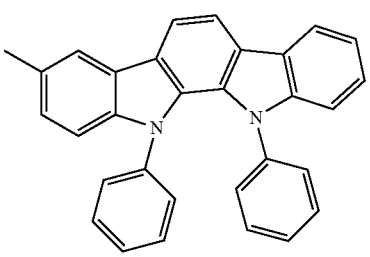
formula (266)
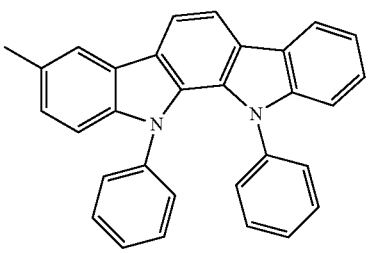

formula (267)
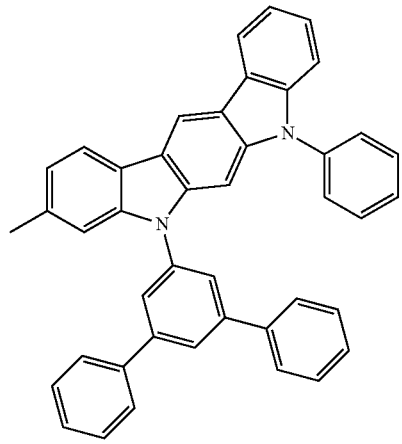
formula (268)
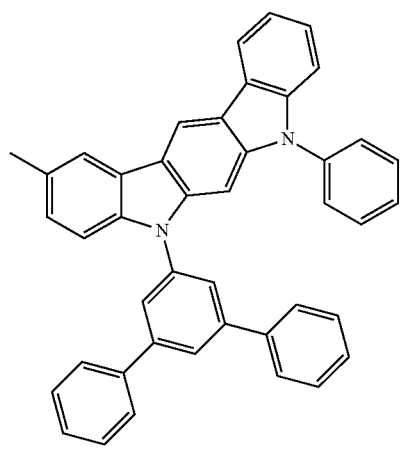
formula (269)
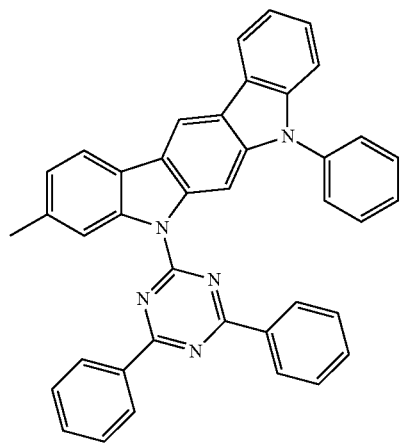
formula (270)
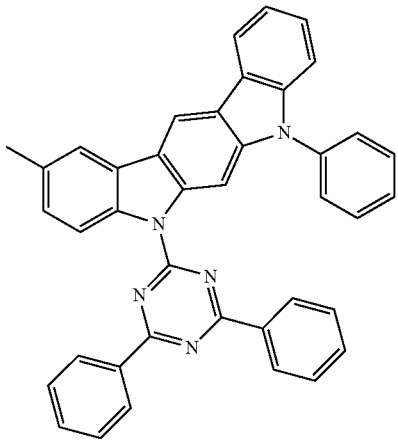
formula (271)
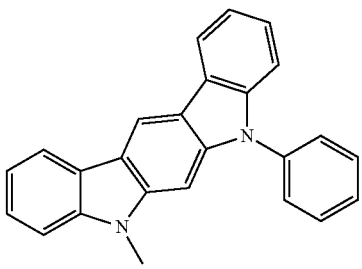
formula (272)
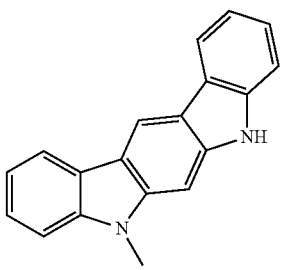
formula (273)
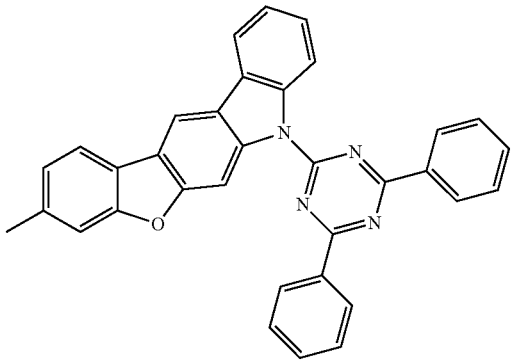

formula (274)
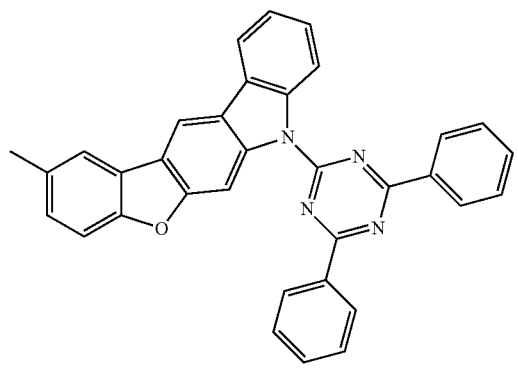
formula (275)
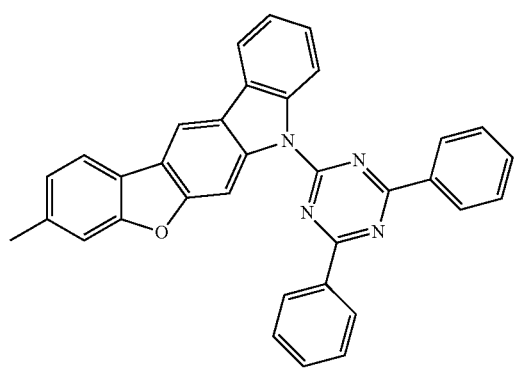
formula (276)
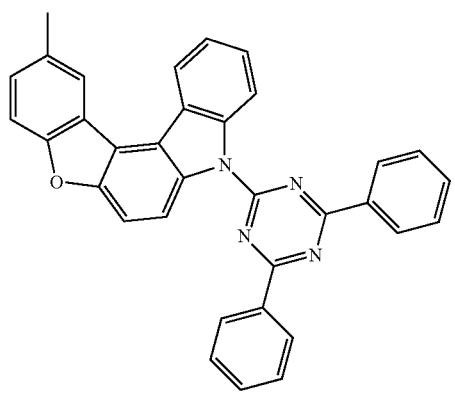
formula (277)
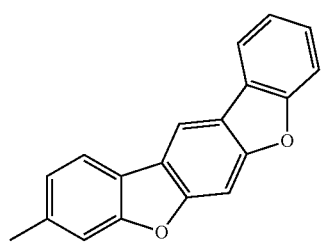
formula (278)
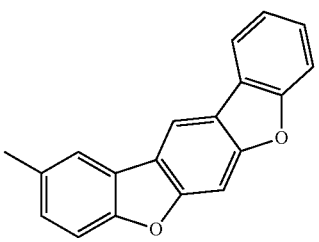
formula (279)
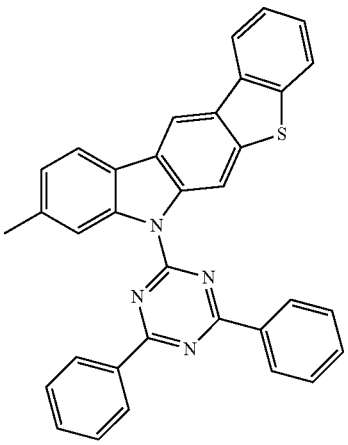
formula (280)
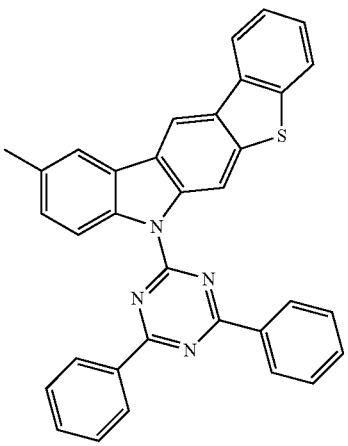
formula (281)
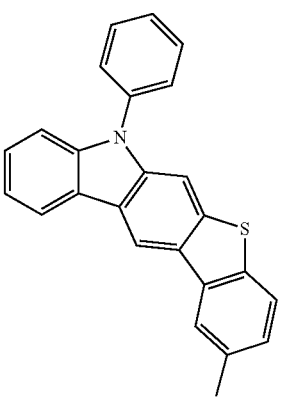

-continued formula (282)
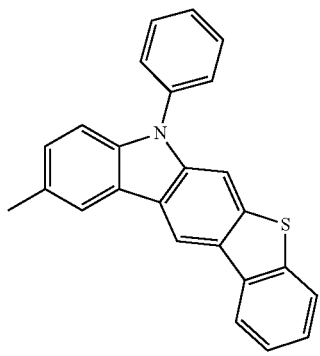

formula (283)
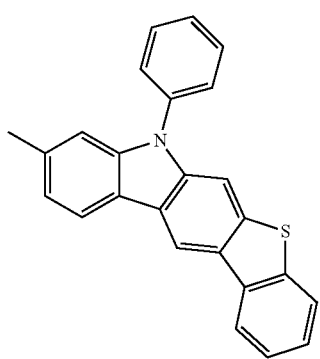

formula (284)
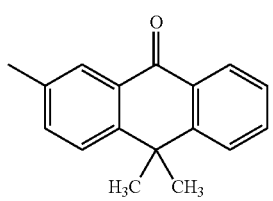

formula (285)
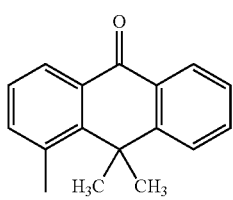

formula (286)
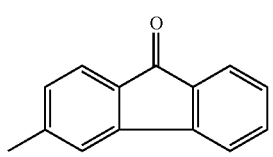

formula (287)
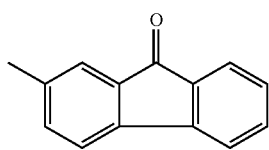

formula (288)
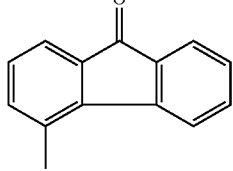

-continued formula (289)
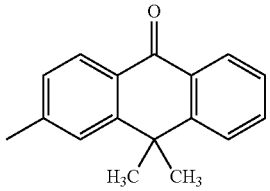

where the dash denotes the position of the linking of the radical Z.

The compounds of the formula (1) can also be used as monomers of the general formula (290) for the preparation of oligomers, dendrimers and polymers. In this case, the polymer containing the compound of the formula (1) can be both a homopolymer and also a copolymer.

The present invention accordingly also relates to monomers of the general formula (290)

formula (290)
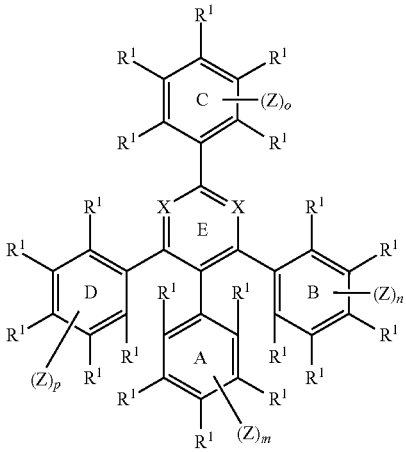

where the above definitions apply to the symbols and indices used (see formula (1))
and at least one of the rings A, B, C or D must be substituted by a substituent Z in the meta position
and with the proviso that at least one of the radicals Z must be an aromatic or heteroaromatic group having 5 to 60 aromatic ring atoms
and where the substituent or substituents Z in each case replace the radicals $R^1$ and
two or more of the radicals $R^1$ are identically or differently functional groups which polymerise under conditions of the C—C or C—N linking reactions.

The functional groups are preferably selected from Cl, Br, I, O-tosylate, O-triflate, O—SO$_2$R$^2$, B(OR$^2$)$_2$ and Sn(R$^2$)$_3$, particularly preferably from Br, I and B(OR$^2$)$_2$, where R$^2$ is on each occurrence, identically or differently, H, an aliphatic or aromatic hydrocarbon radical having 1 to 20 C atoms, and where two or more radicals R$^2$ may also form a ring system with one another.

The monomers may furthermore, as described above, contain crosslinkable groups Q, so that the polymers containing the monomers of the formula (290) can be crosslinked.

The compounds of the formula (1) according to the invention where X=CH are synthesised by palladium-catalysed cross-couplings on the correspondingly halogenated basic structures having the general formula (291).

formula (291)
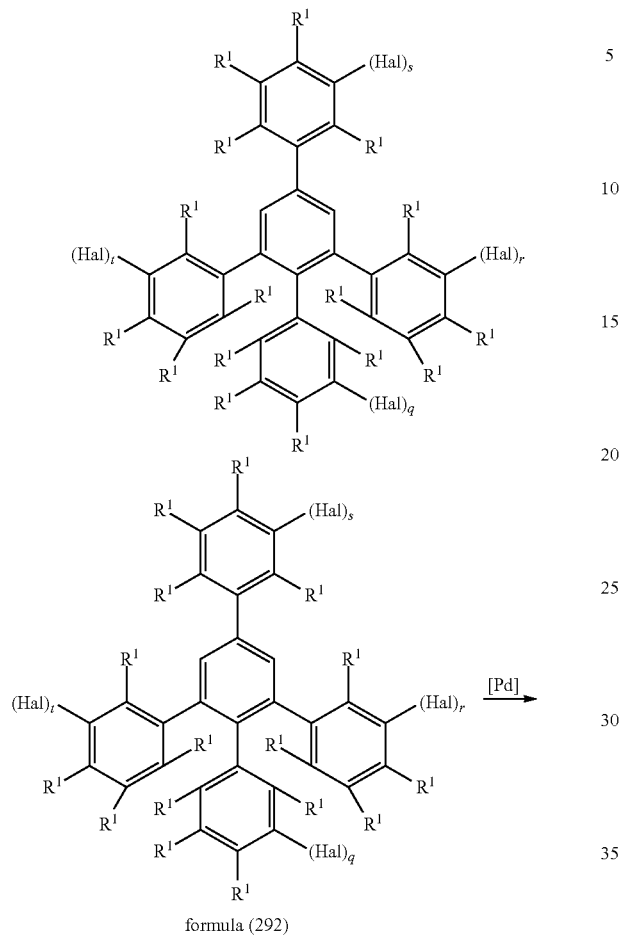
formula (292)
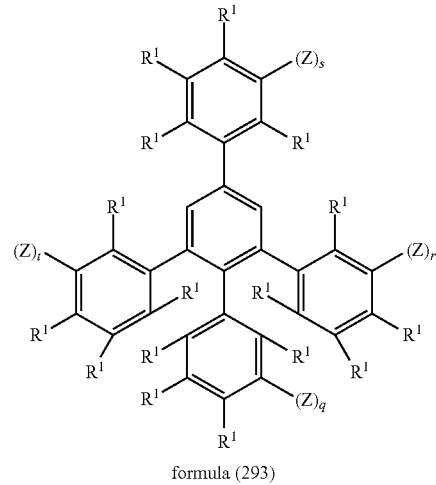
formula (293)
where the above definitions apply to the symbols and indices used. The basic structures can be prepared from pyrylium salts by general processes correspondingly to the following scheme (Journal f. Prakt. Chemie 1987, 329, 6, 975-984).
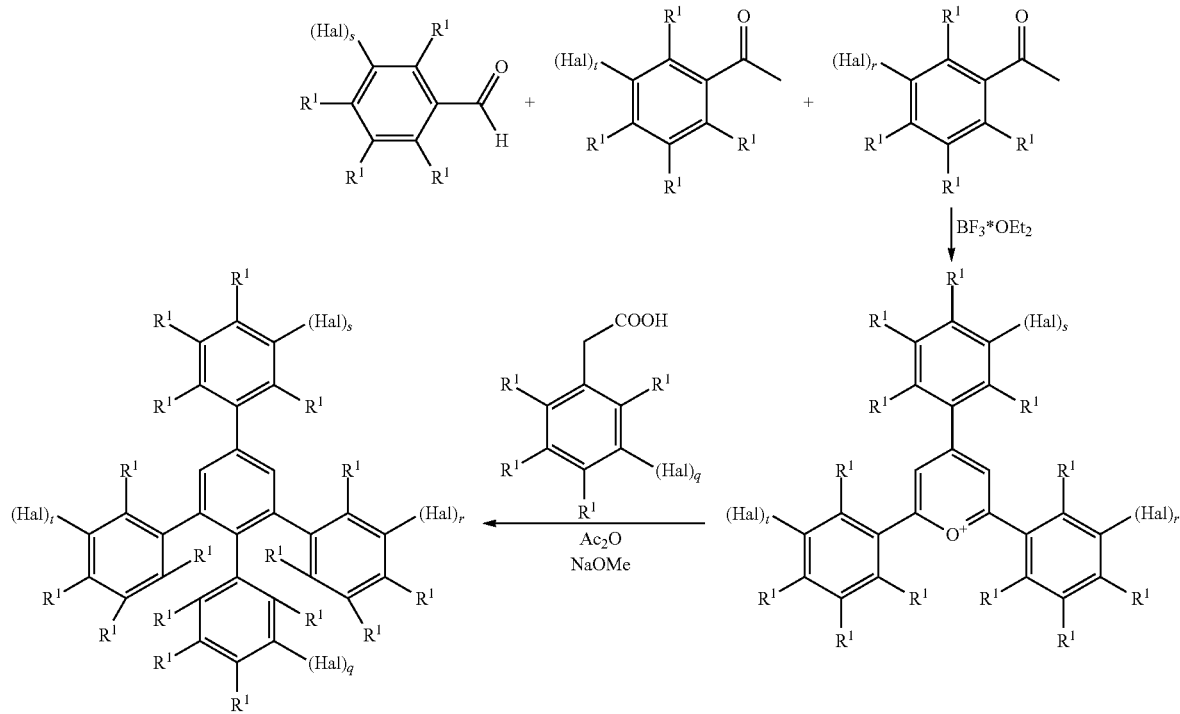

Symmetrically substituted compounds of the formula (1) according to the invention where X=N are synthesised by palladium-catalysed Suzuki-Miyaura couplings on commercially available 2,4,5,6-tetrachloropyrimidine (Adv. Synth. Catal. 2010, 352, 1429-1433).

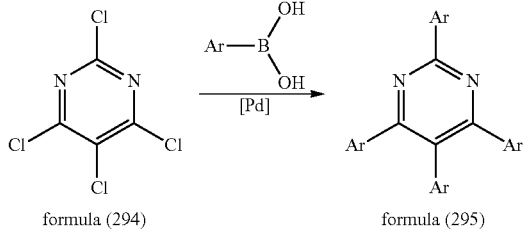

Asymmetrically substituted compounds of the formula (1) according to the invention where X=N are preferably synthesised by boron trifluoride-catalysed [2+2'+2']cycloaddition of alkynes and nitriles (Synthesis 1983, 9, 717-718) in accordance with the following scheme:

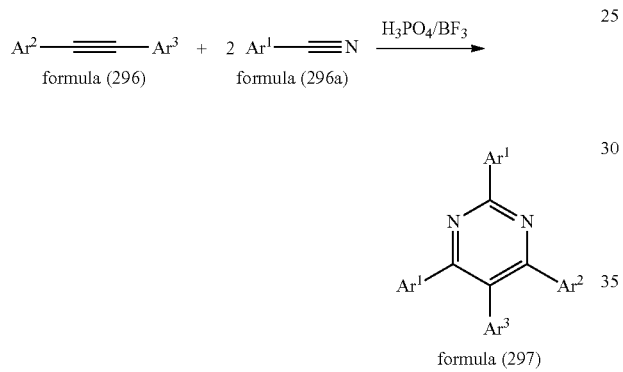

A further possibility for the preparation of asymmetrically substituted compounds of the formula (1) according to the invention where X=N is the preparation process described in Tetrahedron Letters 2005, 46, 1663-1665 and outlined in the following scheme.

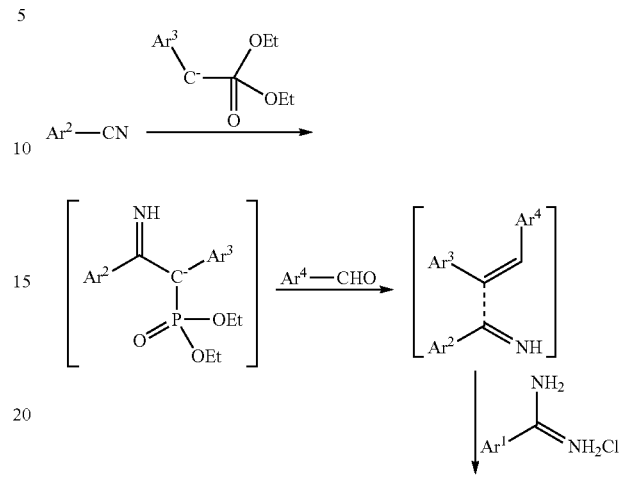

where the radicals Ar, $Ar^1$, $Ar^2$, $Ar^3$ and $Ar^4$ stand for the substituted or unsubstituted aromatic radicals A, B, C and D of the compounds of the formulae (1) to (15).

The present invention therefore also relates to the preparation of the compounds according to the invention by one of the above processes.

Examples of compounds in accordance with the embodiments mentioned above, as can preferably be employed in organic electronic devices, are the compounds of the following structures (298) to (425).

-continued
formula (300)
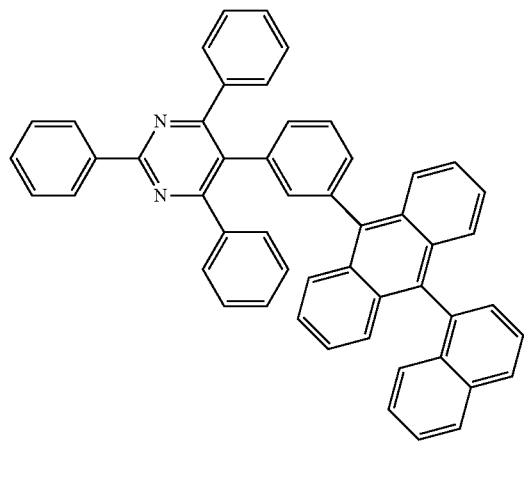
formula (301)
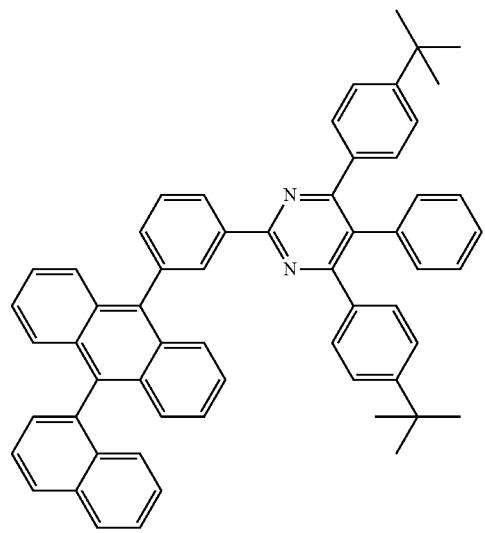
formula (302)
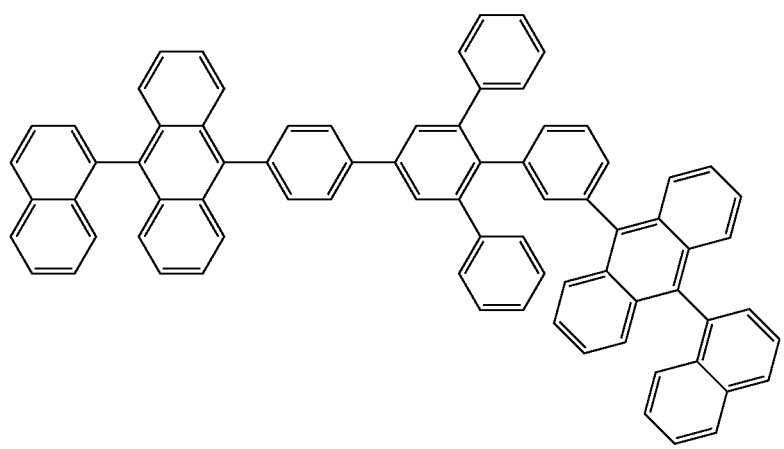
formula (303)
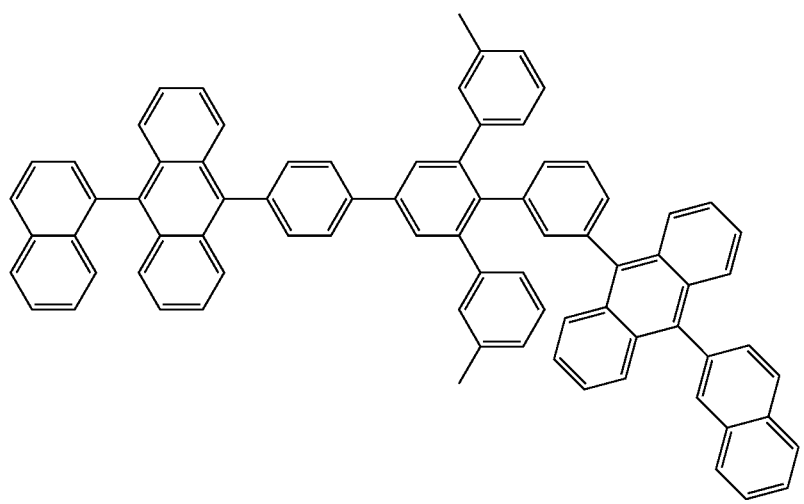

-continued
formula (304)
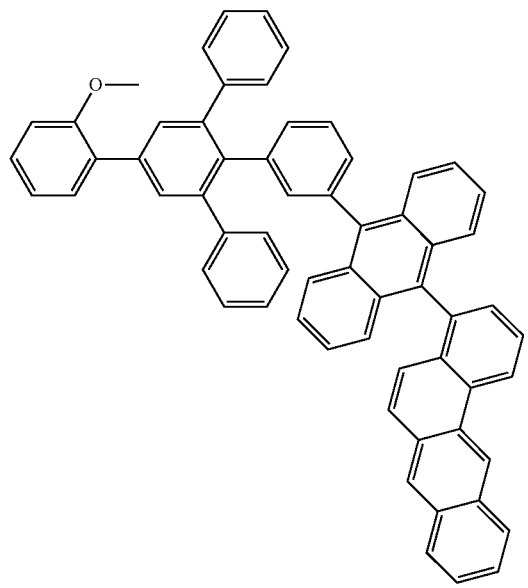
formula (305)
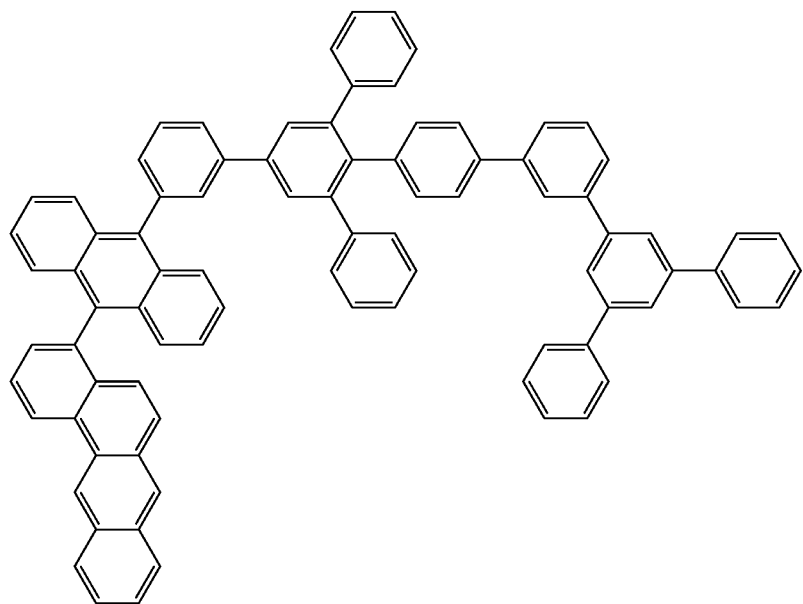

-continued
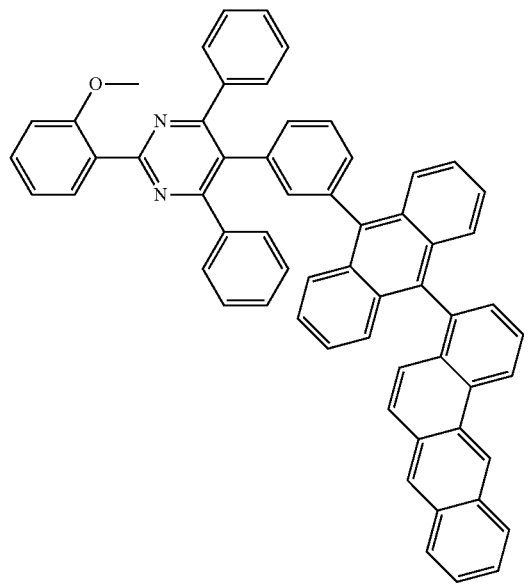
formula (306)
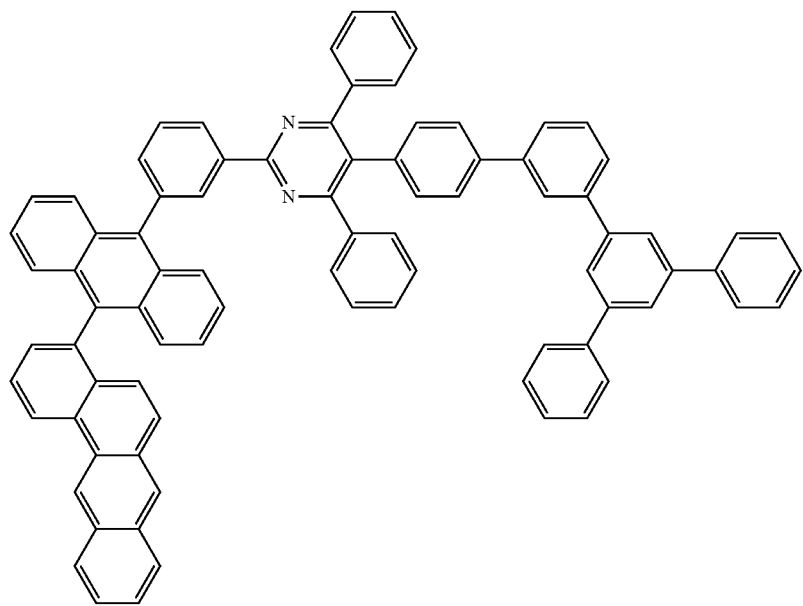
formula (307)

formula (308)
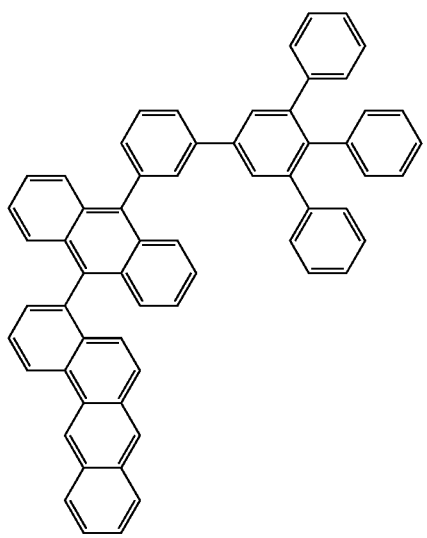
formula (309)
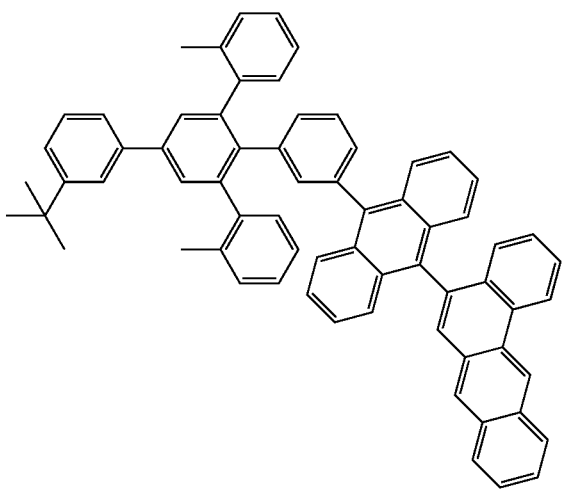
formula (310)
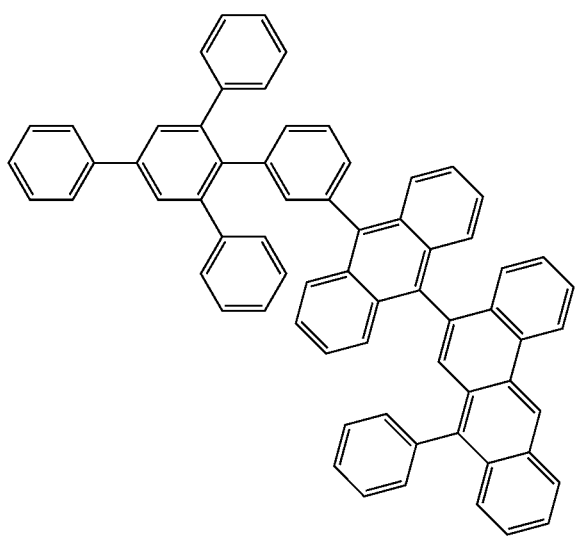
formula (311)
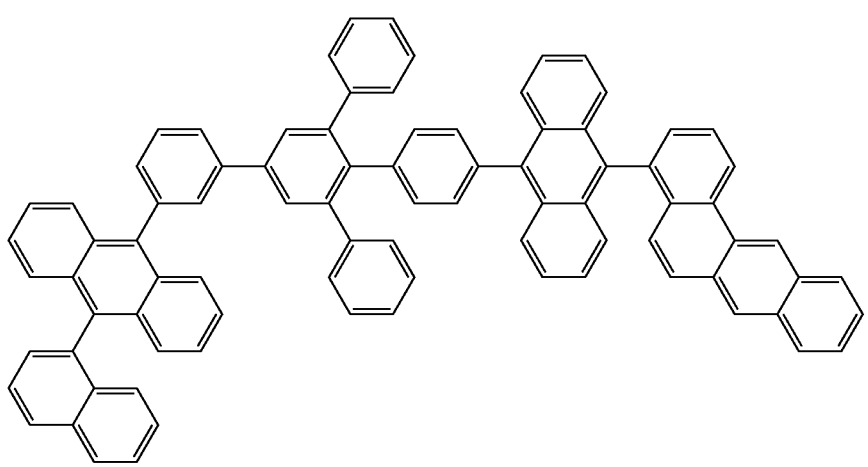

-continued
formula (312)
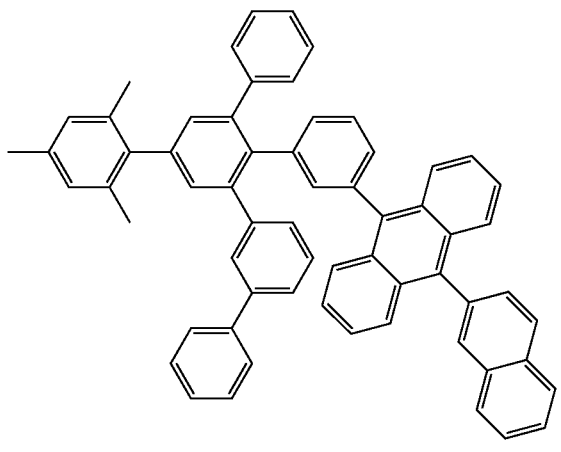
formula (313)
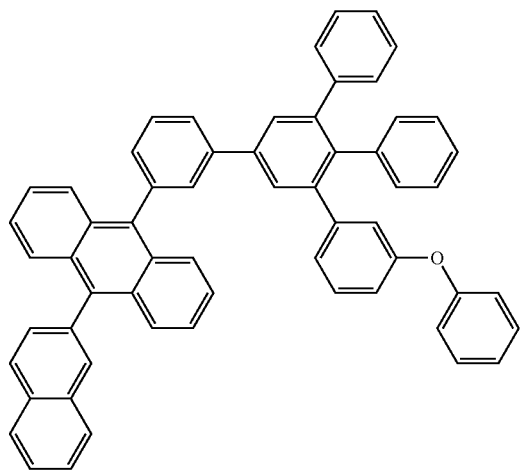
formula (314)
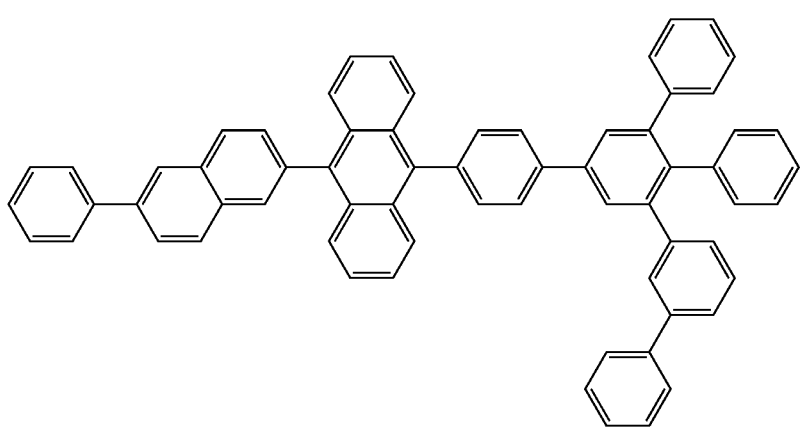
formula (315)
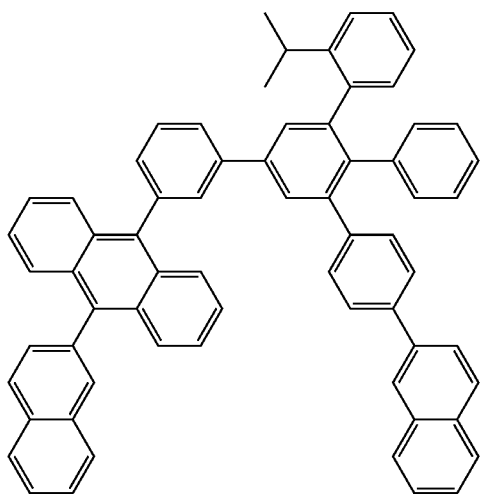
formula (316)
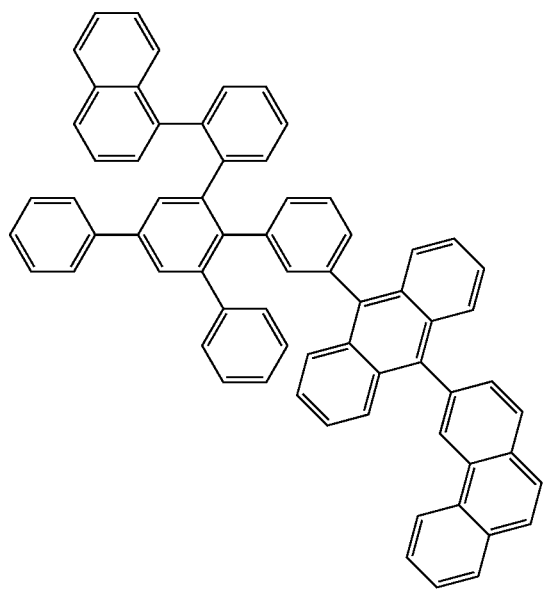

-continued
formula (317)
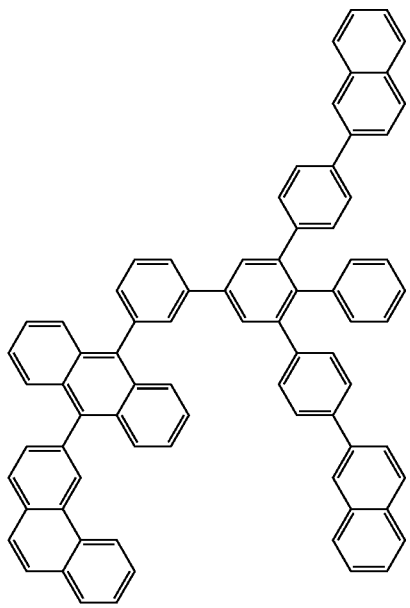
formula (318)
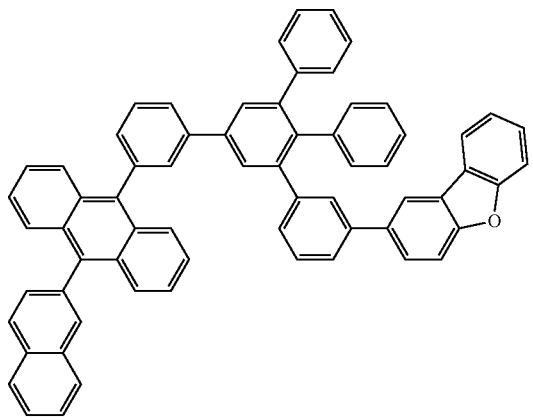
formula (319)
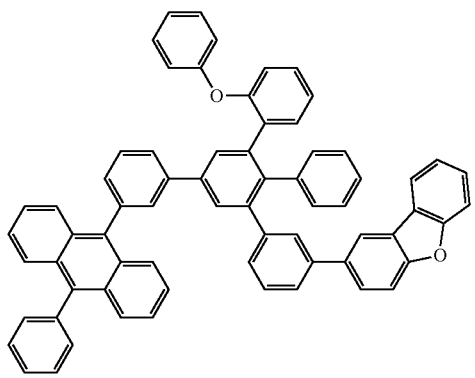
formula (320)
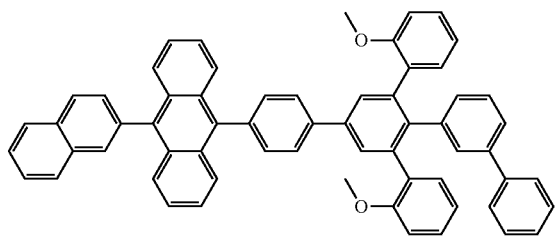
formula (321)
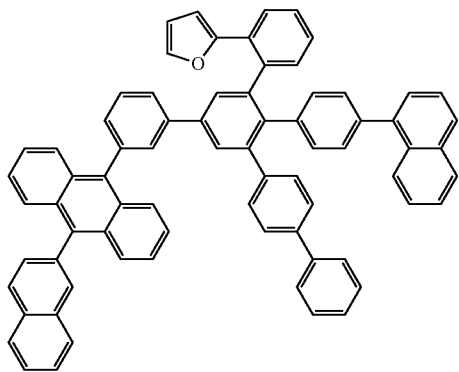
formula (322)
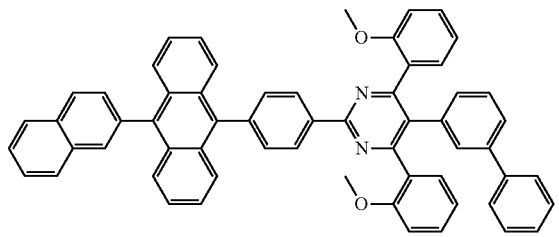

formula (323)
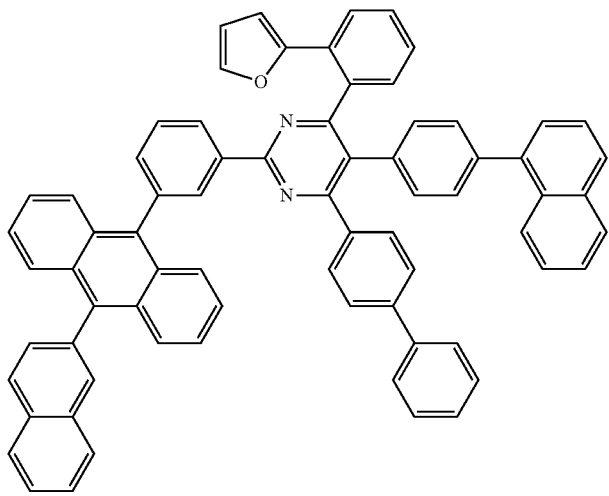
formula (324)
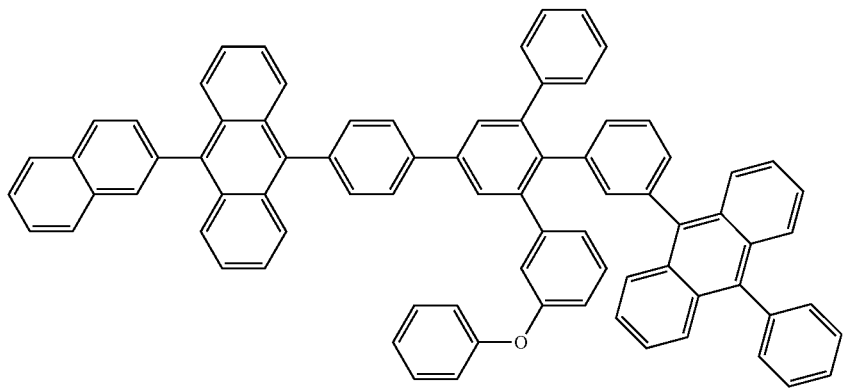
formula (325)
formula (326)
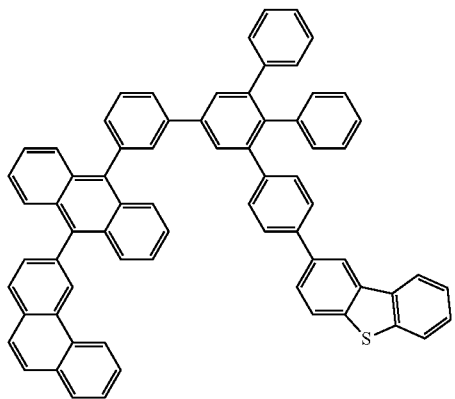

-continued
formula (327)
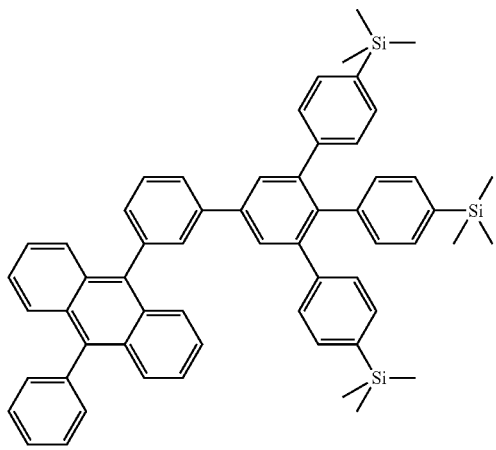
formula (328)
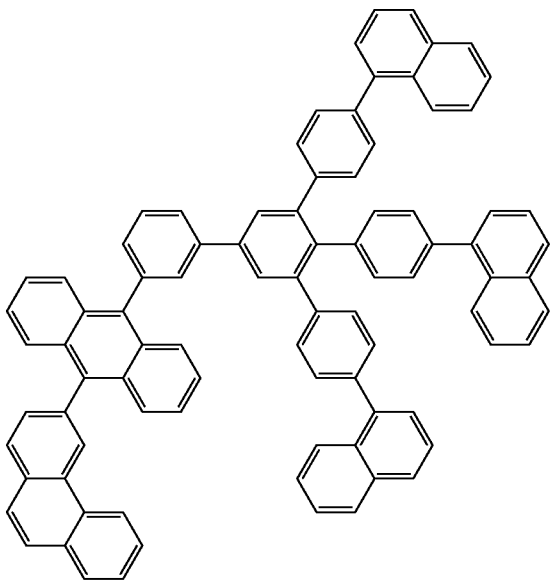
formula (329)
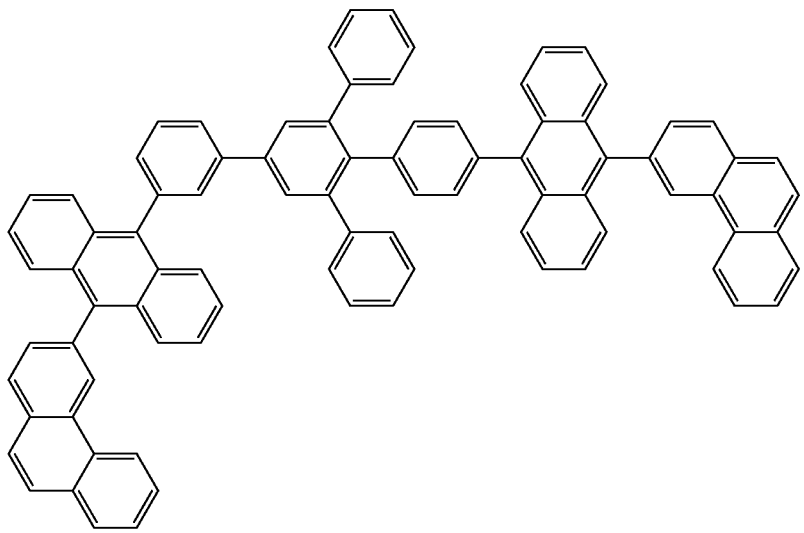
formula (330)
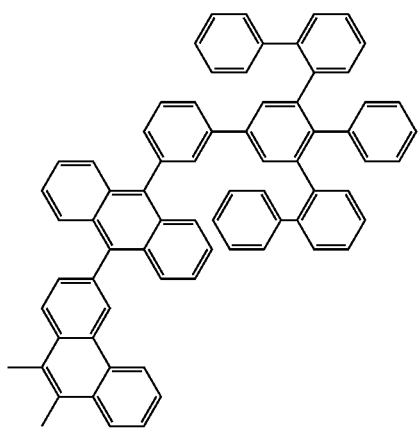
formula (331)
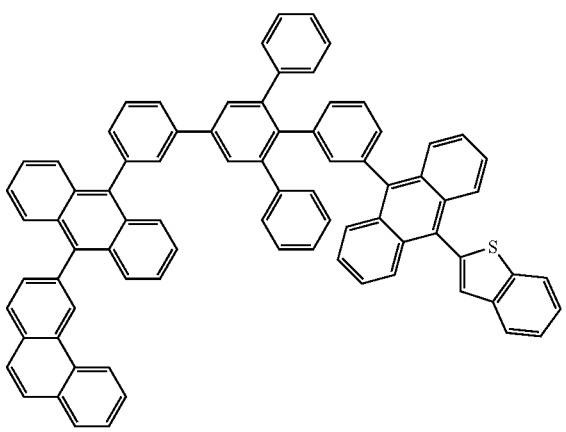

-continued
formula (332)
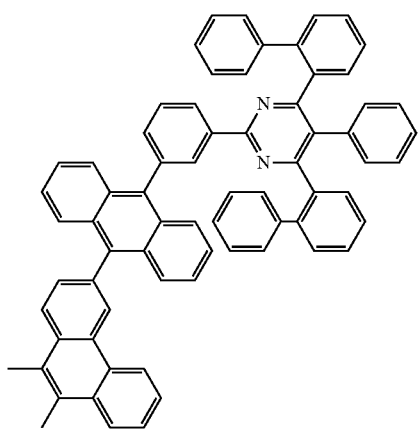
formula (333)
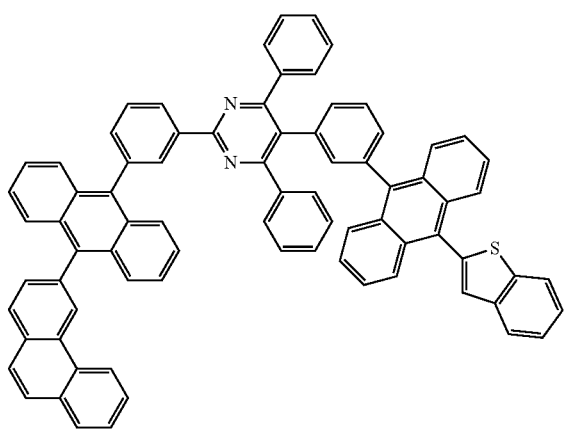
formula (334)
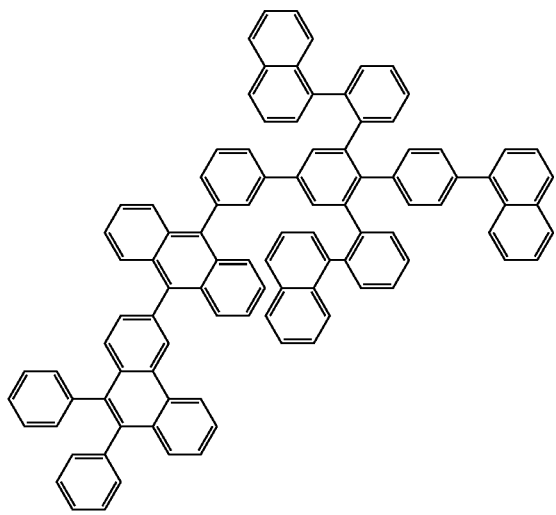
formula (335)
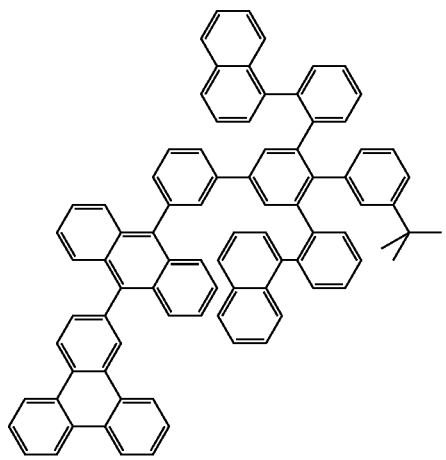
formula (336)
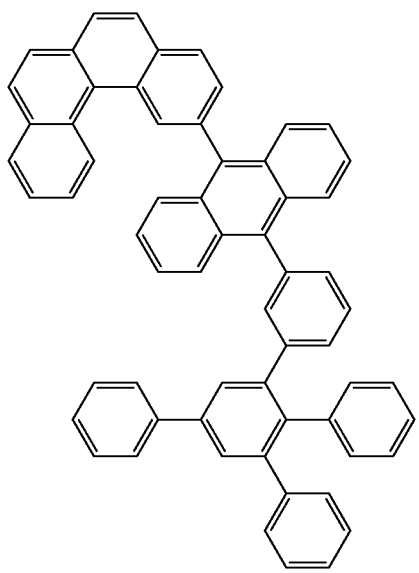

-continued
formula (337)
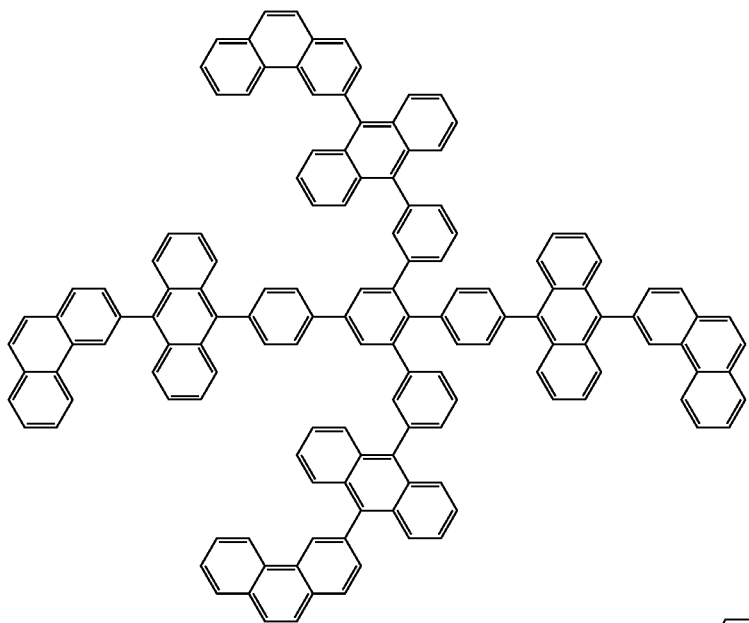
formula (338)
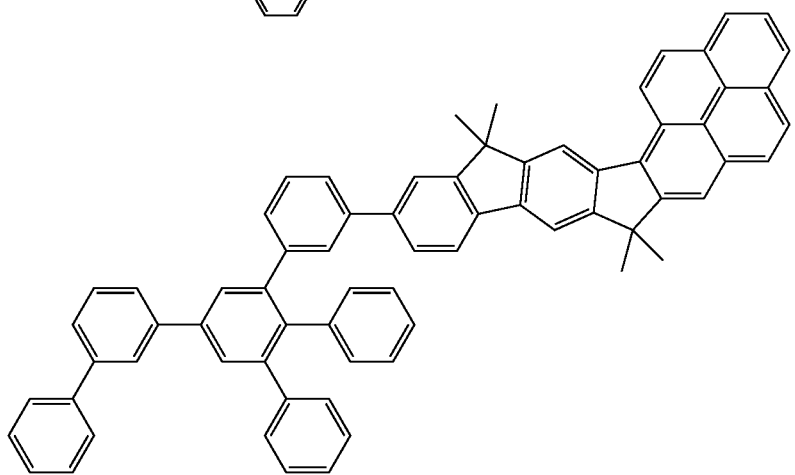
formula (339)
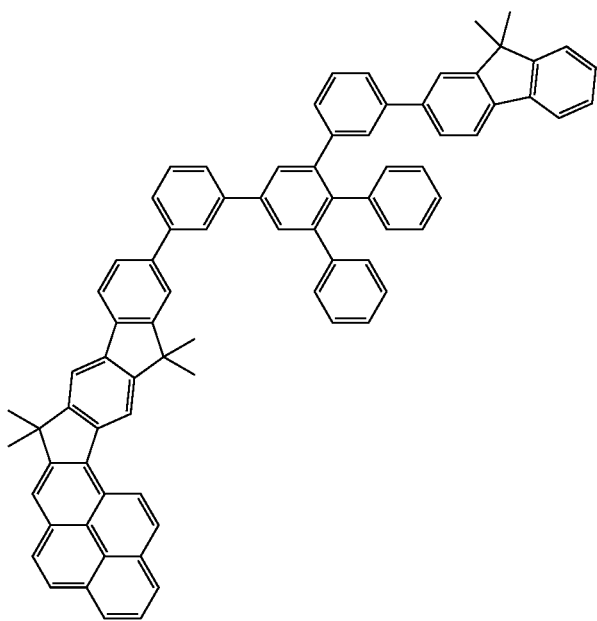

-continued
formula (340)
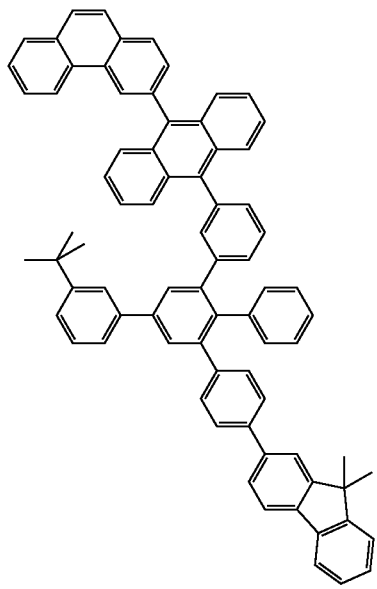
formula (341)
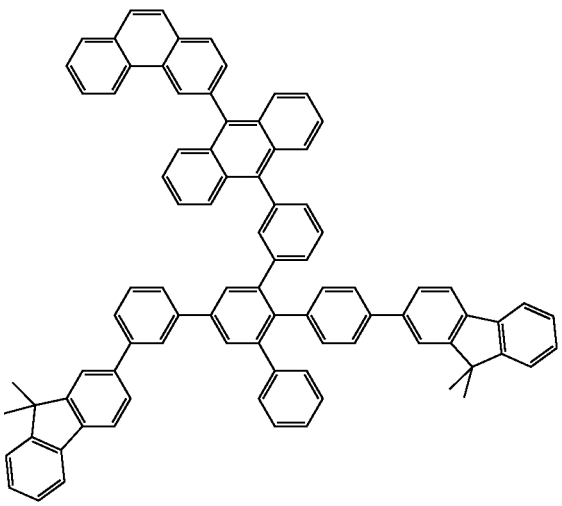
formula (342)
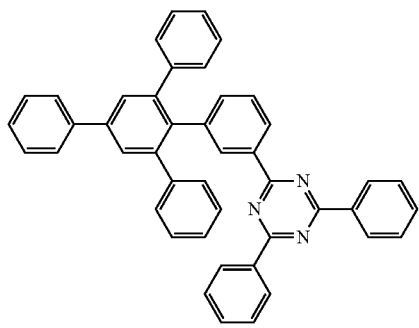
formula (343)
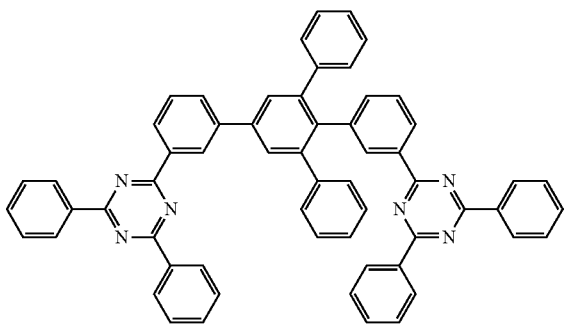
formula (344)
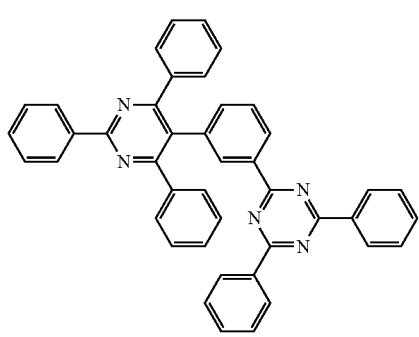
formula (345)
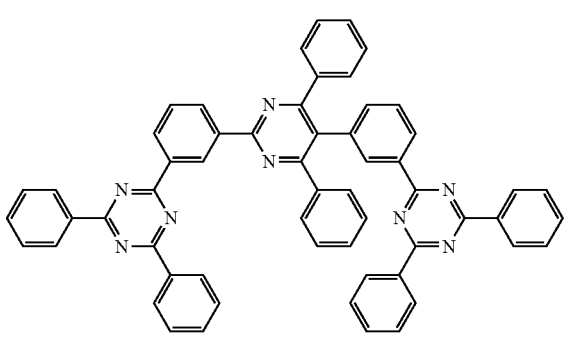
formula (346)
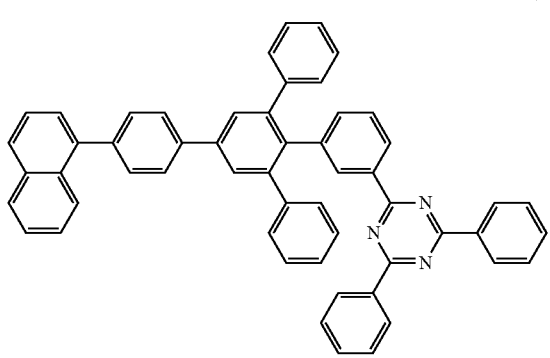
formula (347)
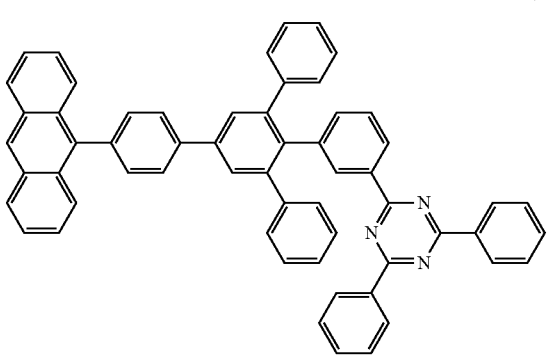

-continued
formula (348)
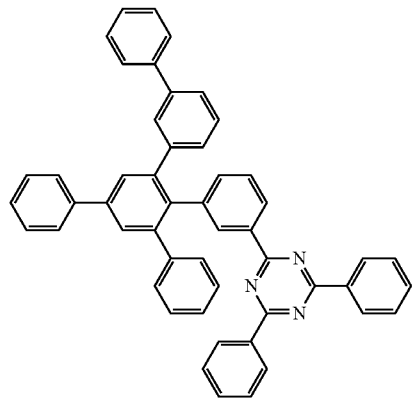
formula (349)
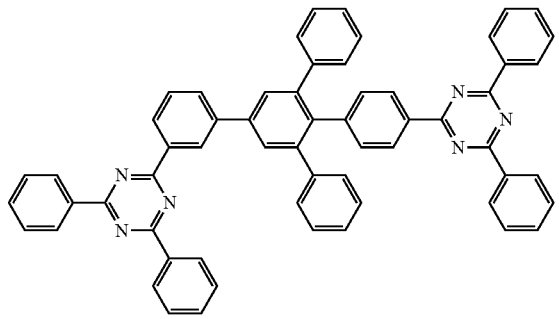
formula (350)
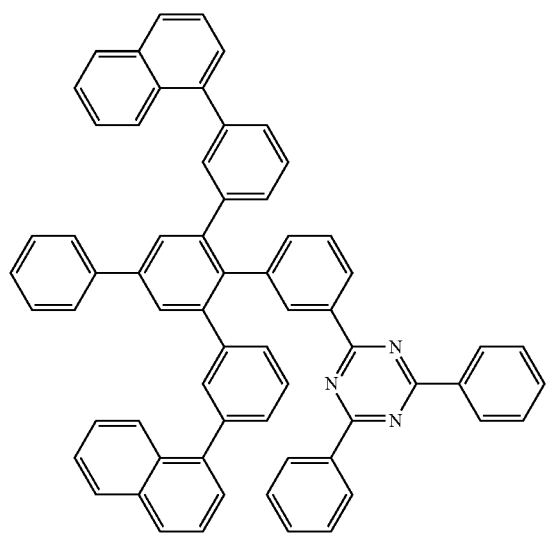
formula (351)
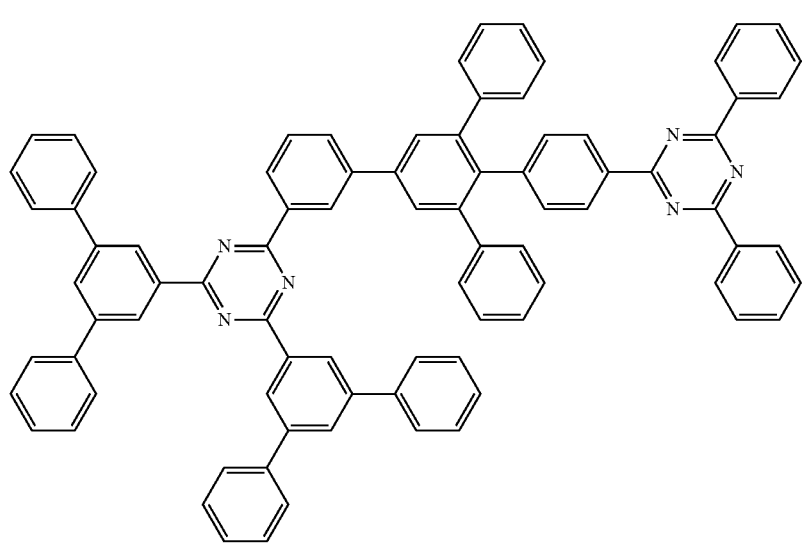

-continued
formula (352)
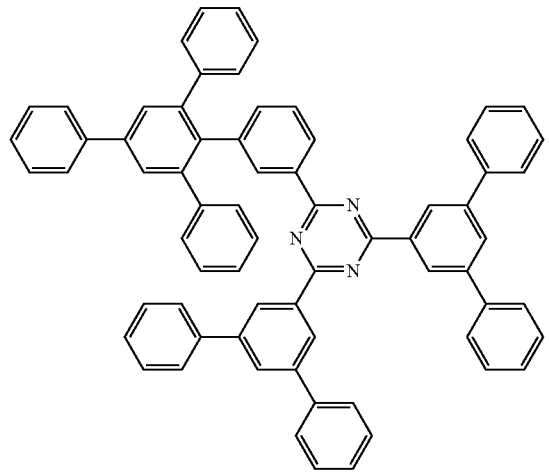
formula (353)
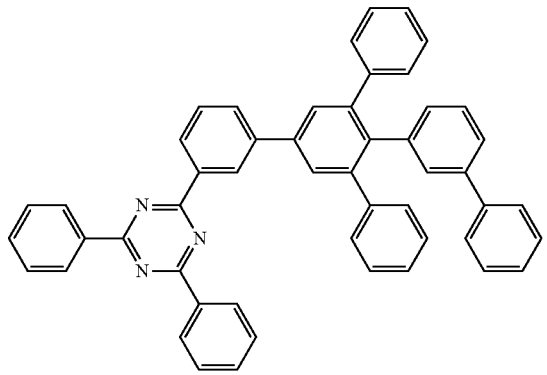
formula (354)
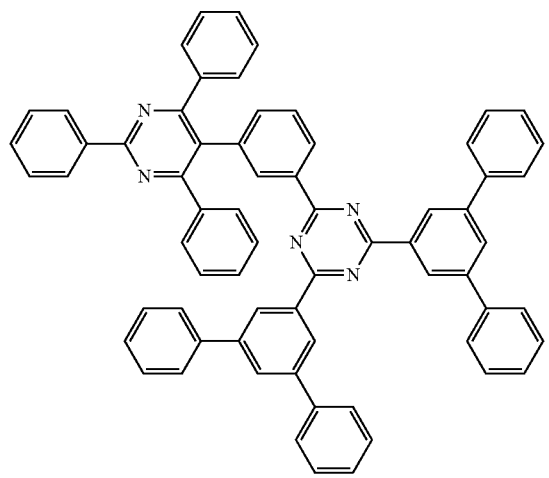
formula (355)
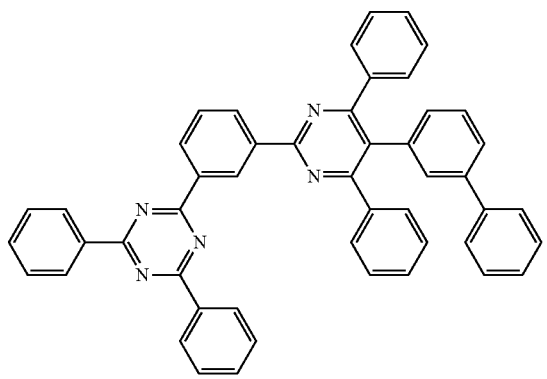
formula (356)
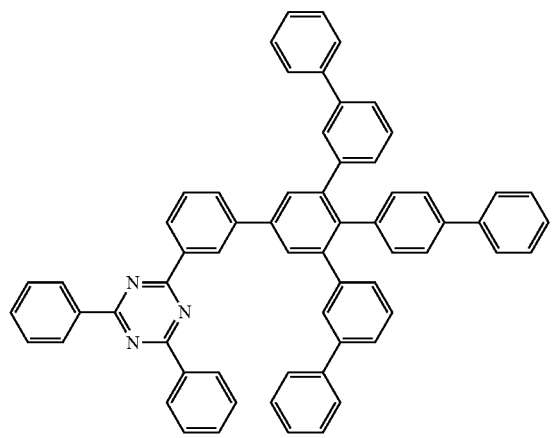
formula (357)
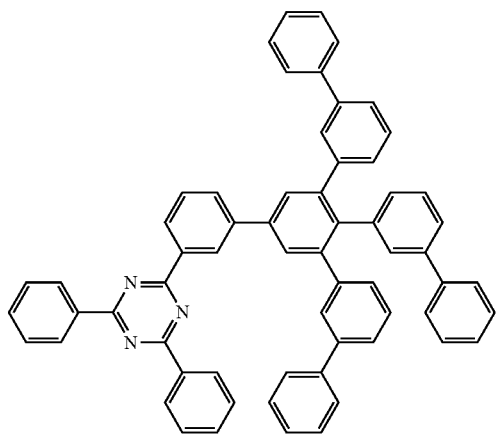

formula (358)
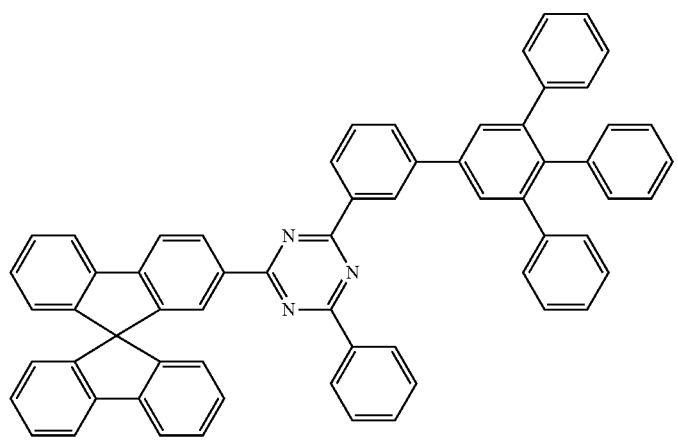
formula (359)
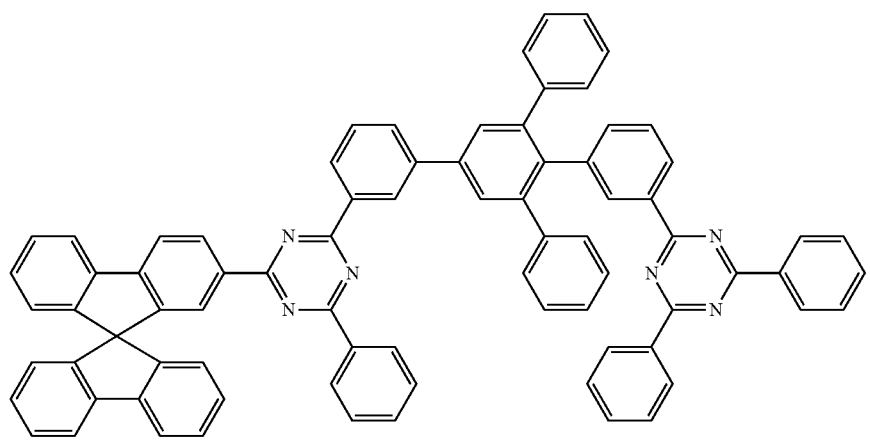
formula (360)
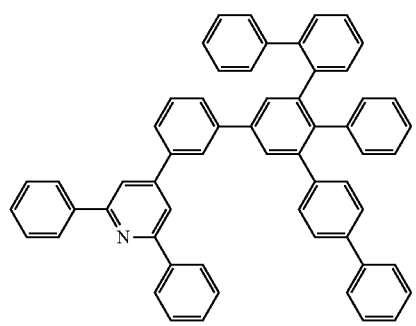
formula (361)
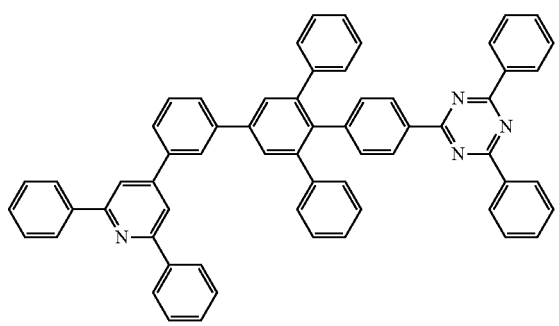
formula (362)
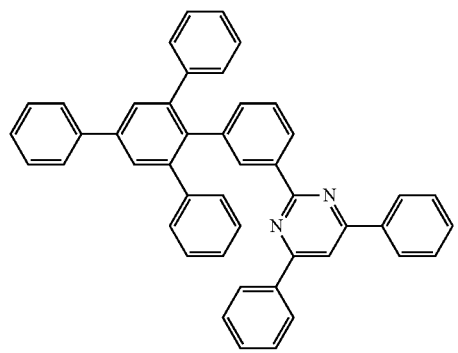
formula (363)
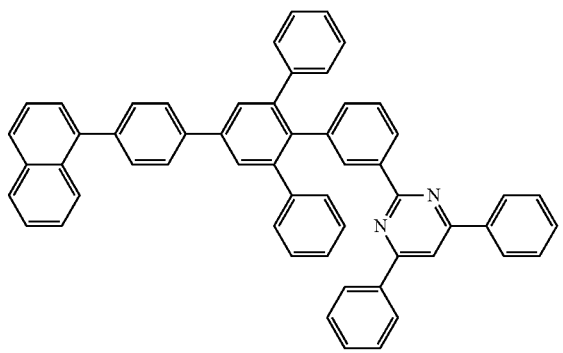

-continued
formula (364)
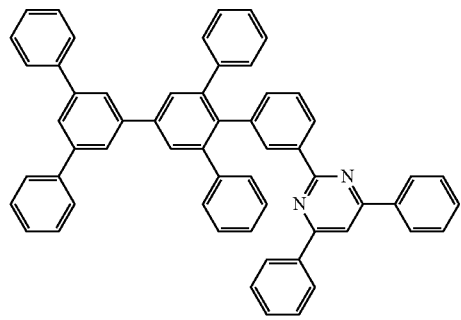
formula (365)
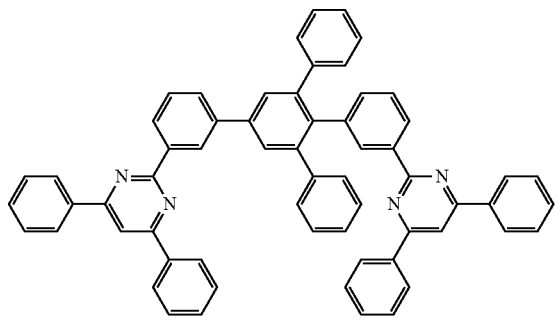
formula (366)
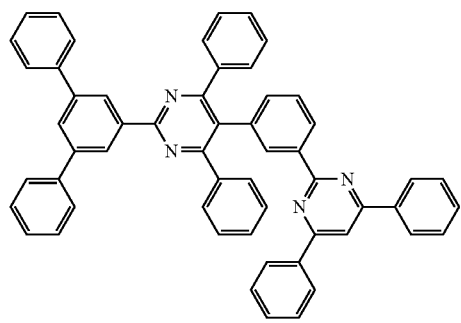
formula (367)
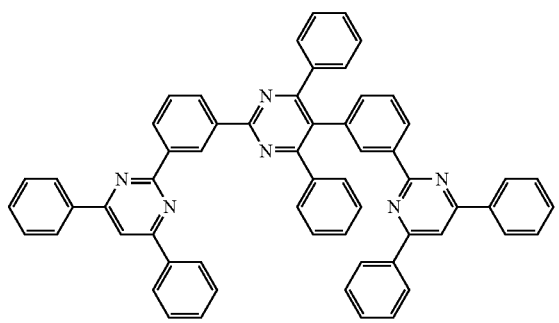
formula (368)
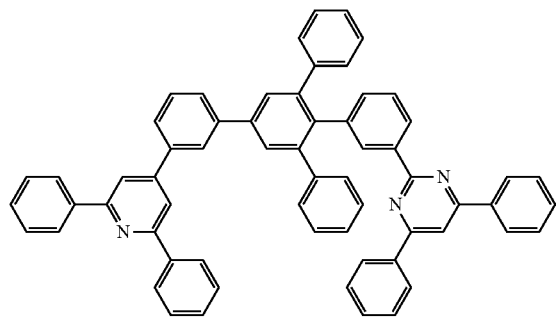
formula (369)
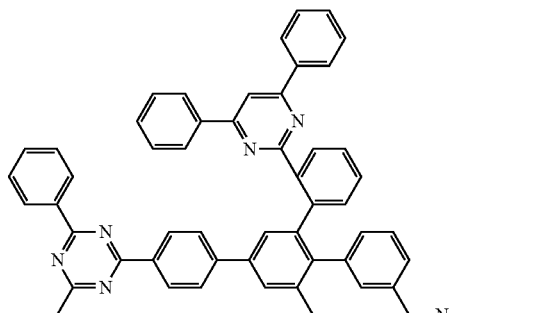
formula (370)
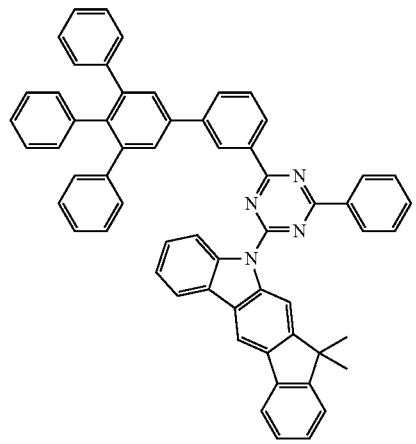
formula (371)
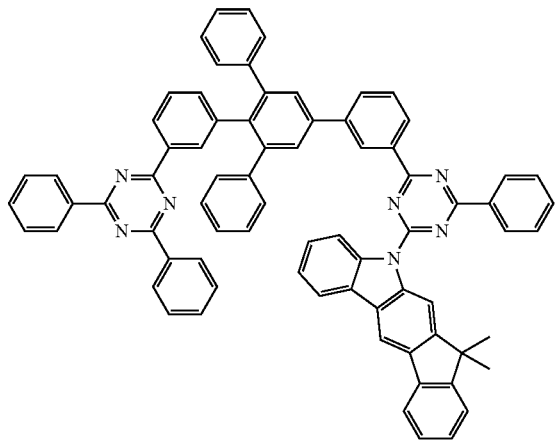

-continued
formula (372)
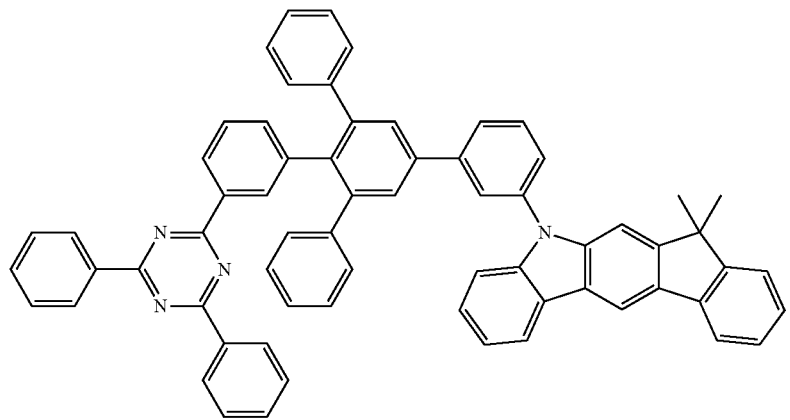
formula (373)
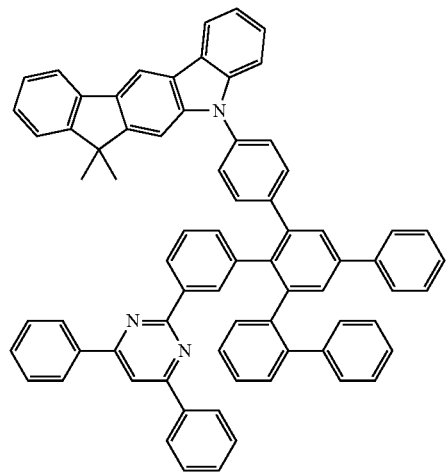
formula (374)
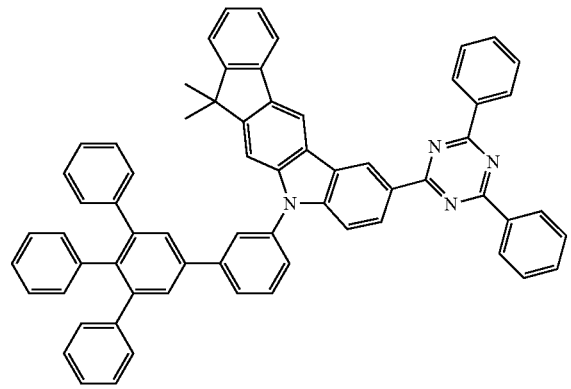
formula (375)
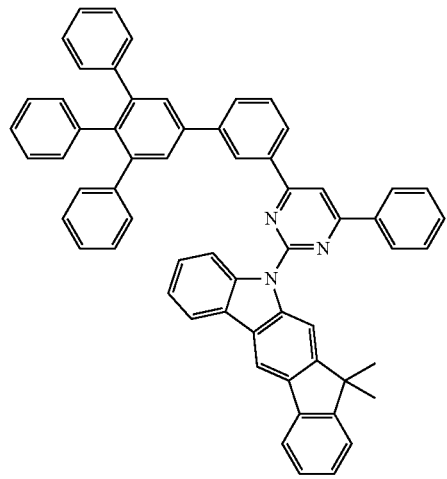
formula (376)
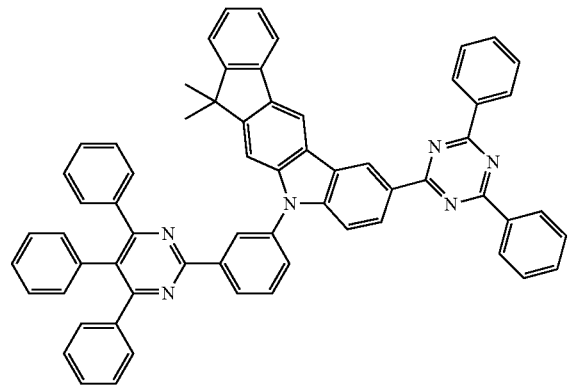

formula (377)
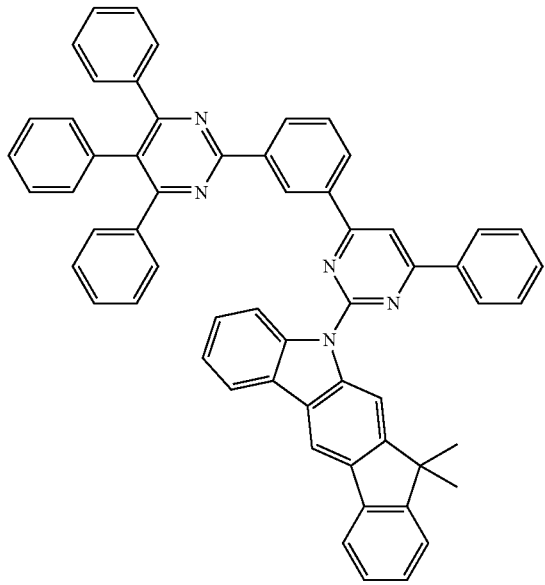
formula (378)
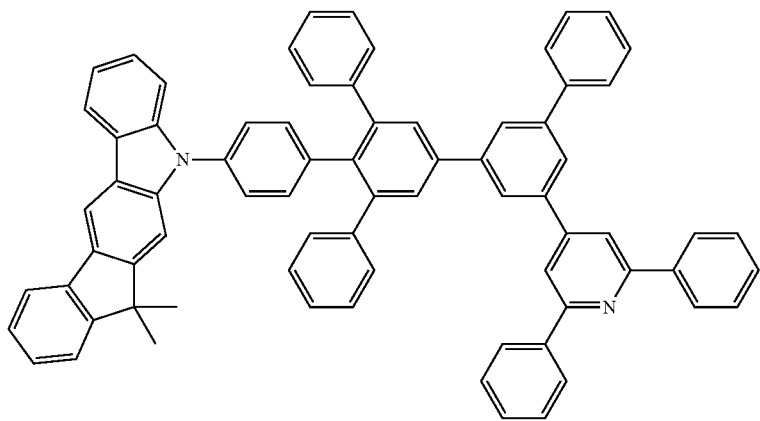
formula (379)
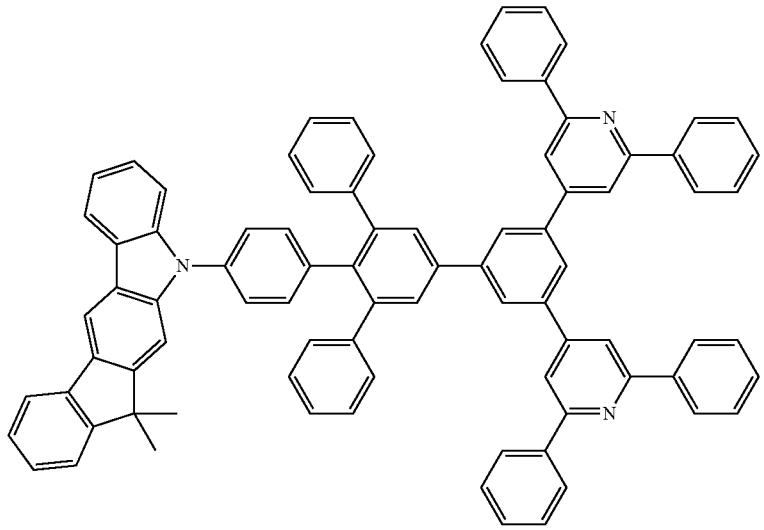

-continued
formula (380)
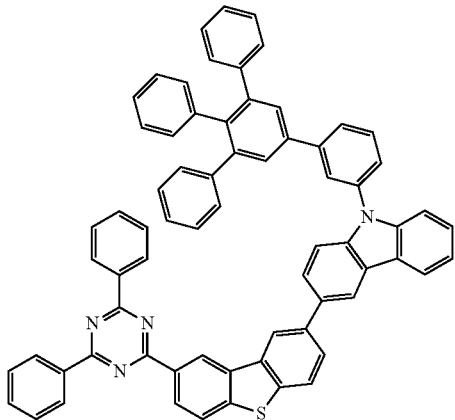
formula (381)
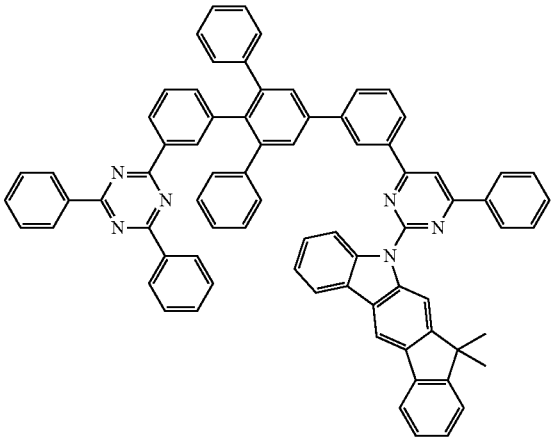
formula (382)
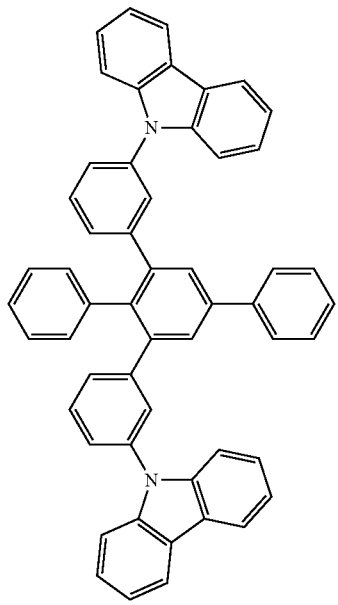
formula (383)
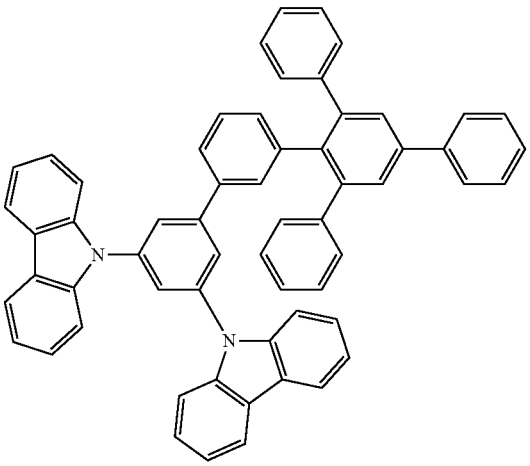
formula (384)
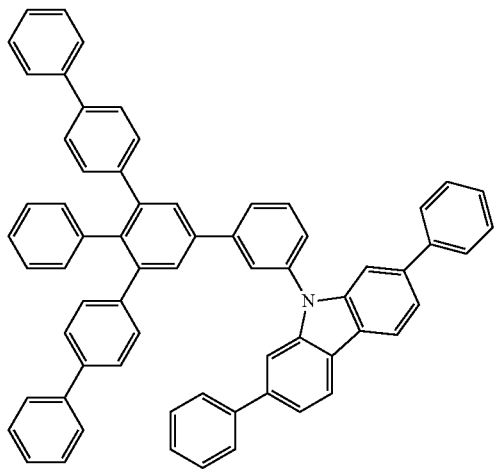
formula (385)
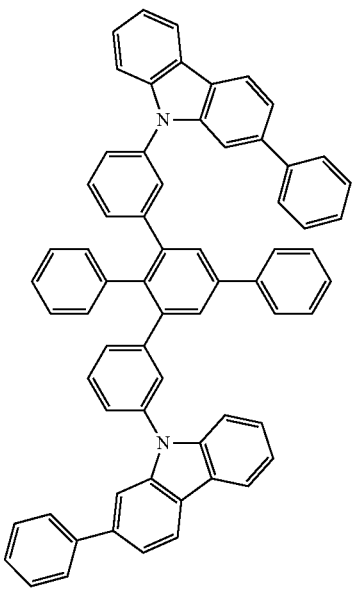

-continued
formula (386)
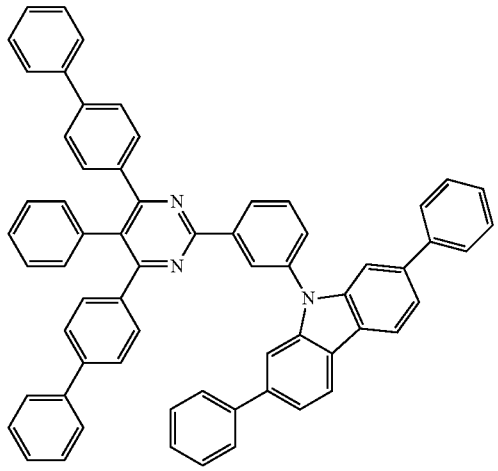
formula (387)
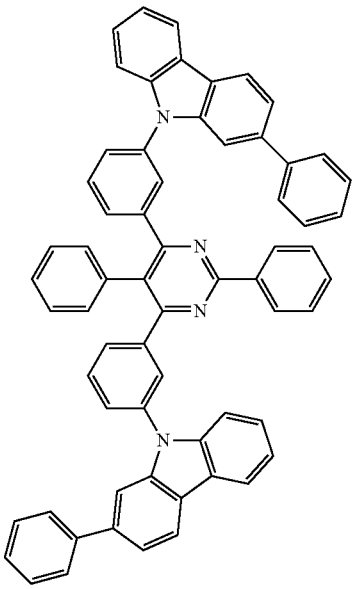
formula (388)
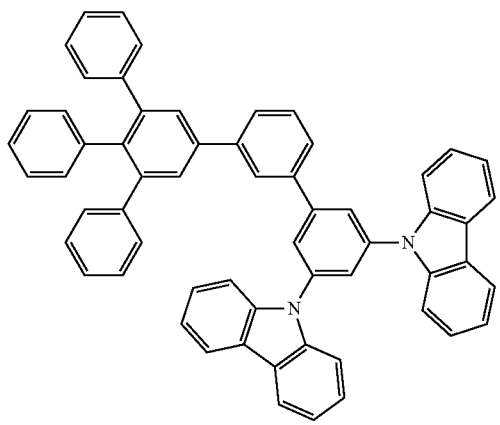
formula (389)
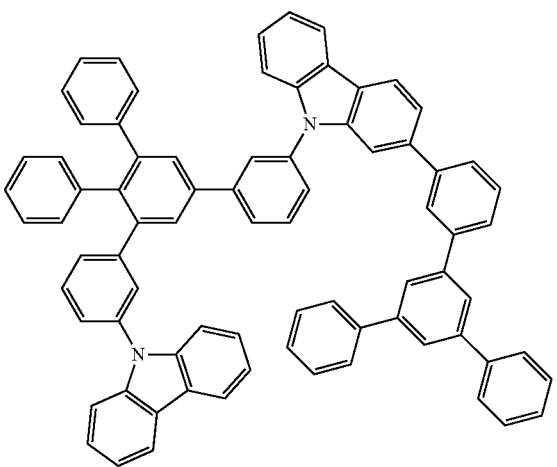
formula (390)
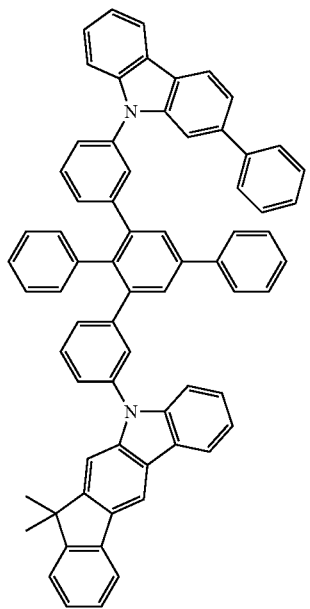
formula (391)
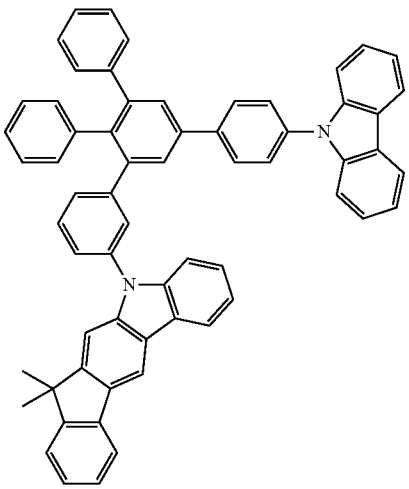

formula (392)
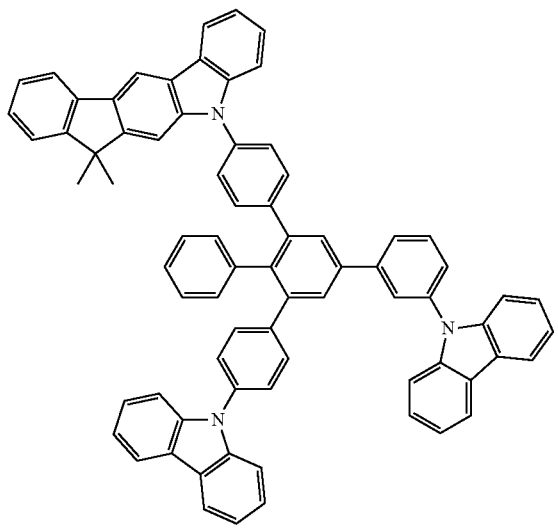
formula (393)
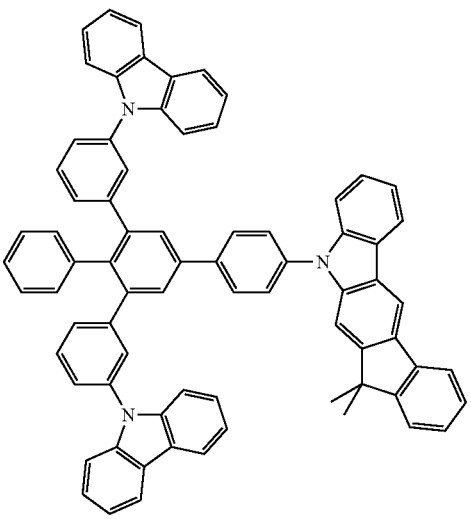
formula (394)
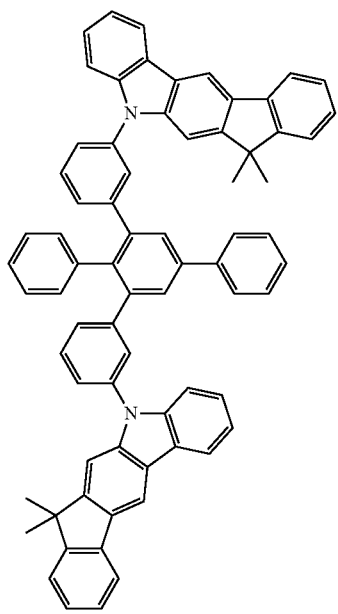
formula (395)
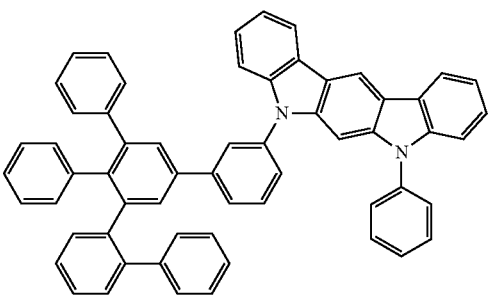
formula (396)
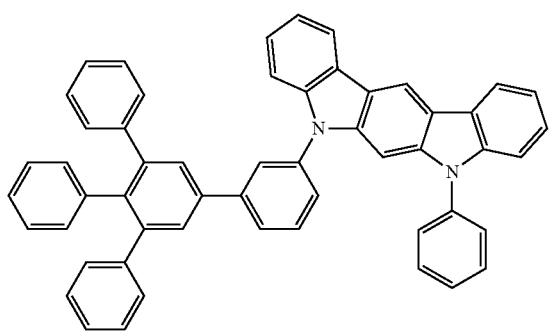
formula (397)
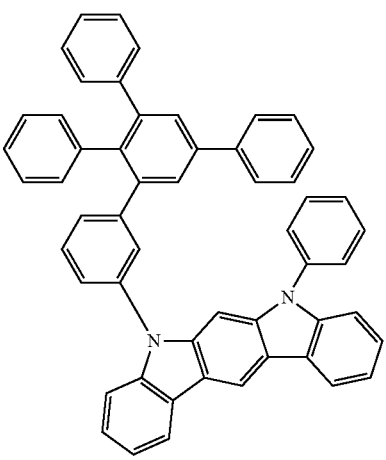

-continued
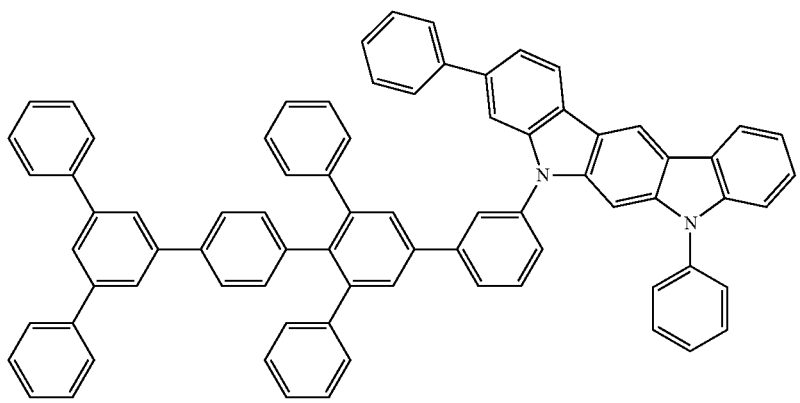
formula (398)
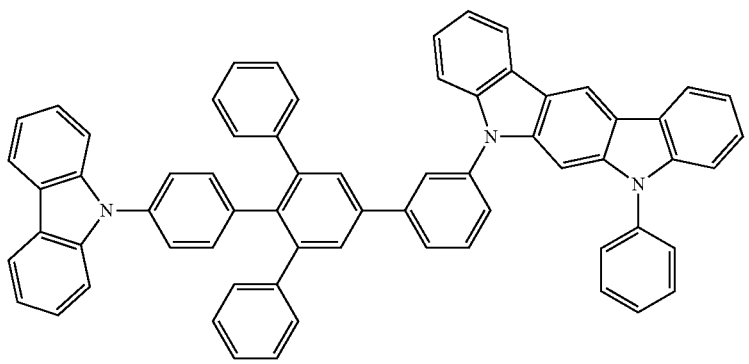
formula (399)
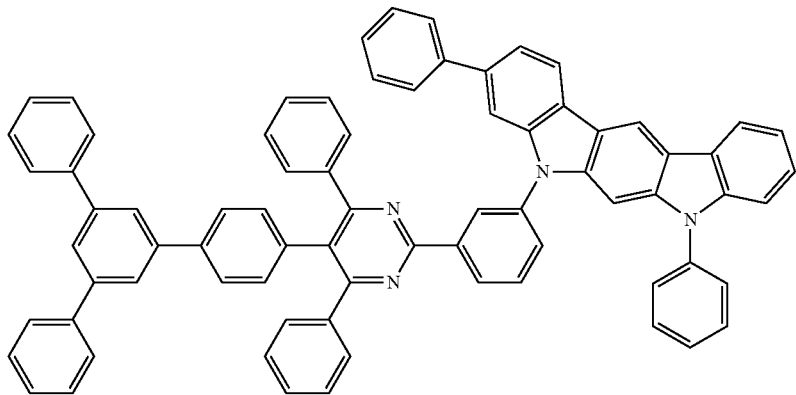
formula (400)
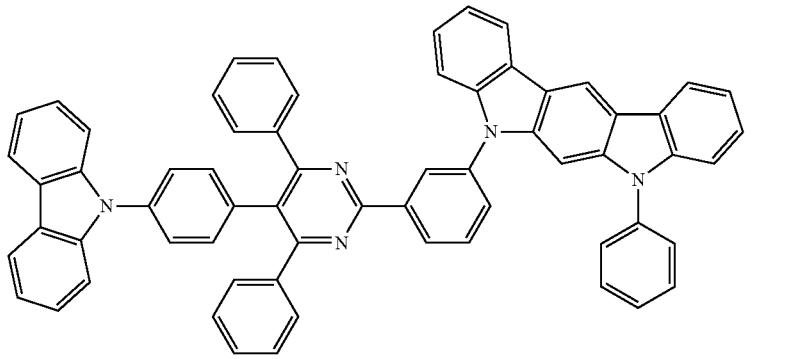
formula (401)

-continued
formula (402)
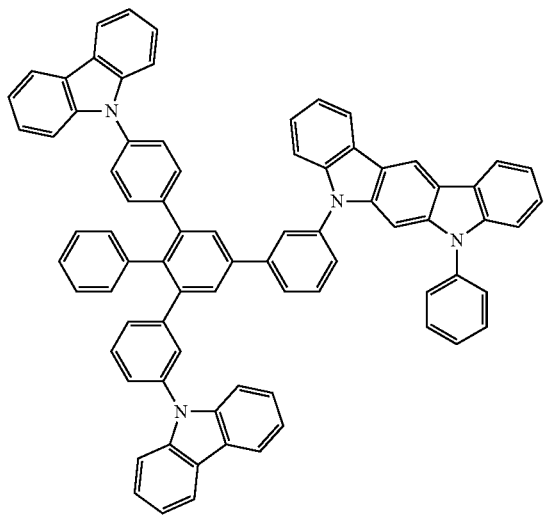
formula (403)
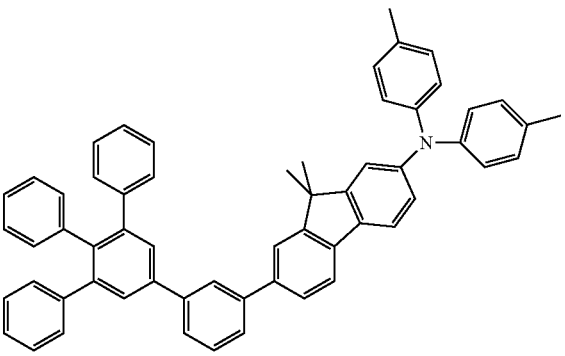
formula (404)
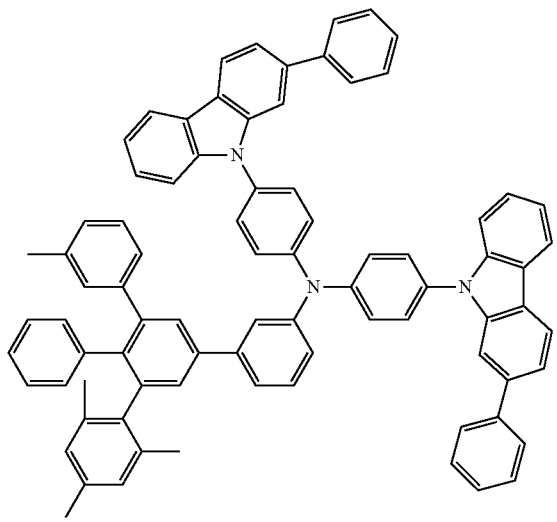
formula (405)
formula (406)
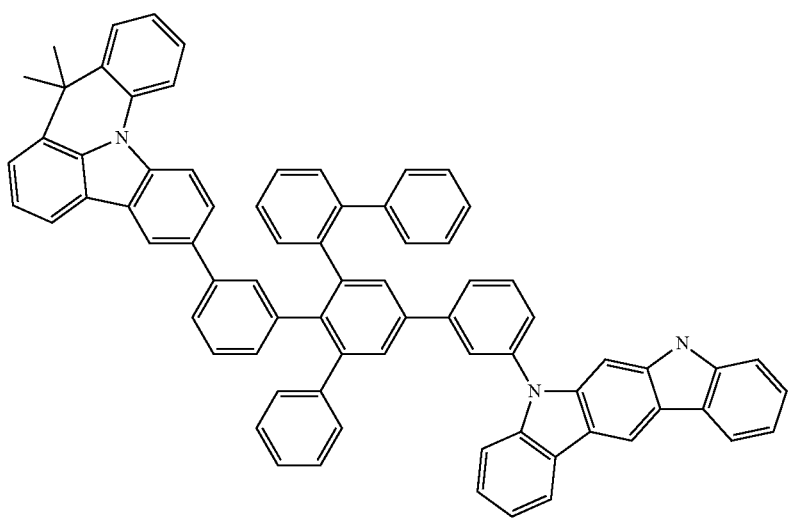

-continued
formula (407)
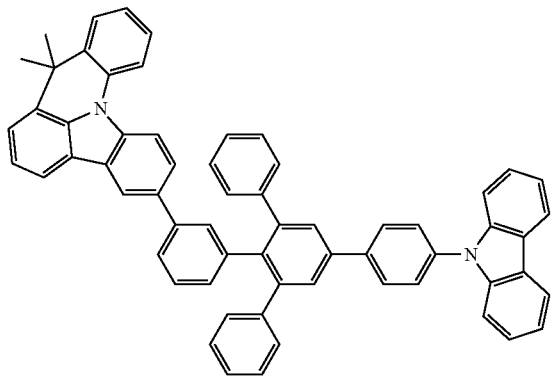
formula (408)
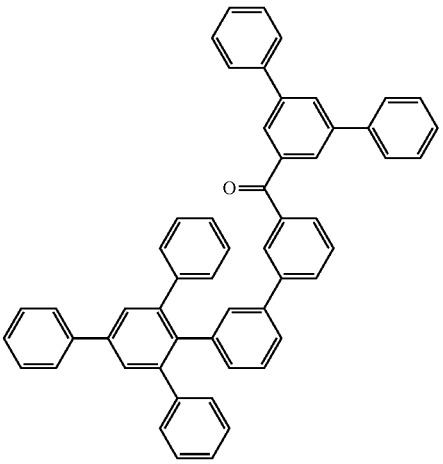
formula (409)
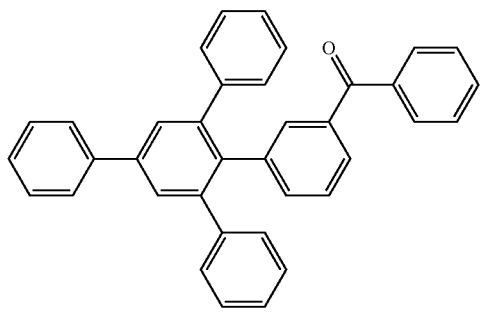
formula (410)
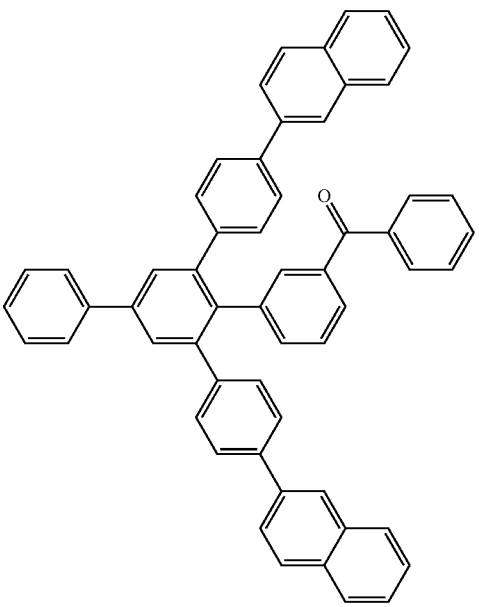
formula (411)
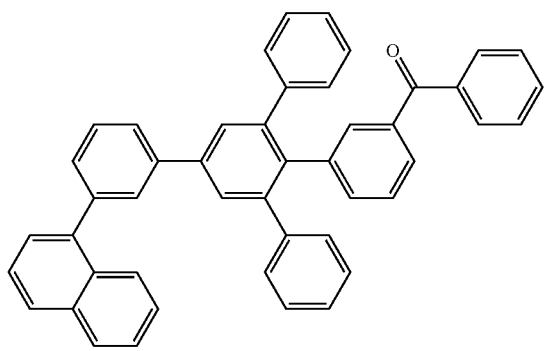
formula (412)
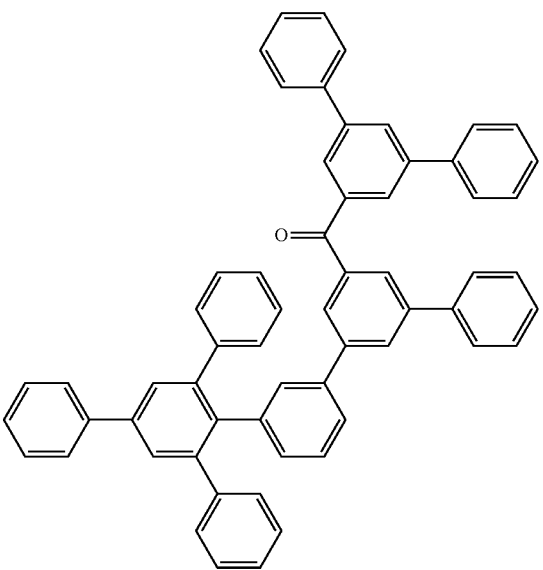

-continued
formula (413)
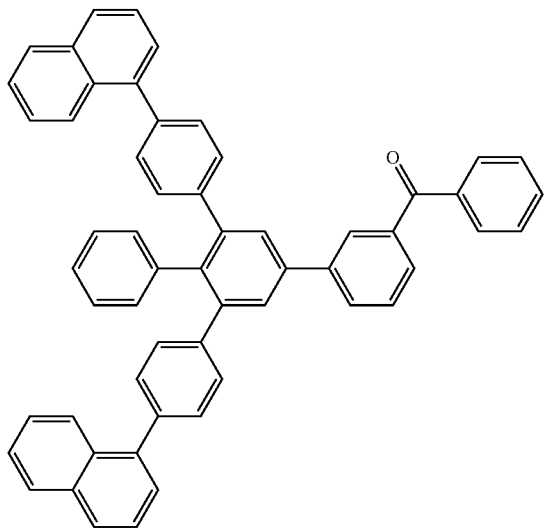
formula (414)
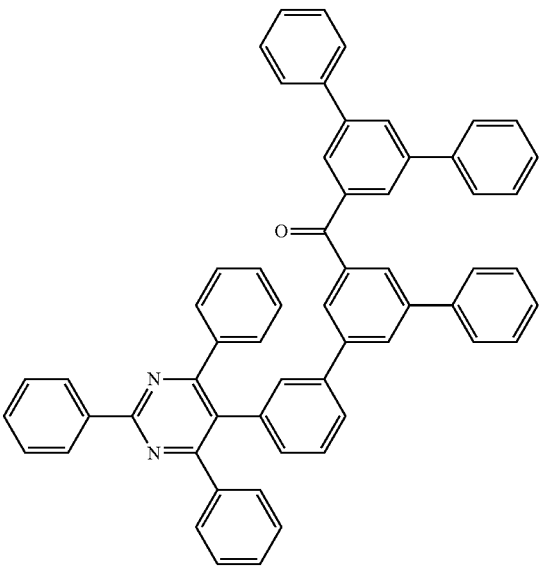
formula (415)
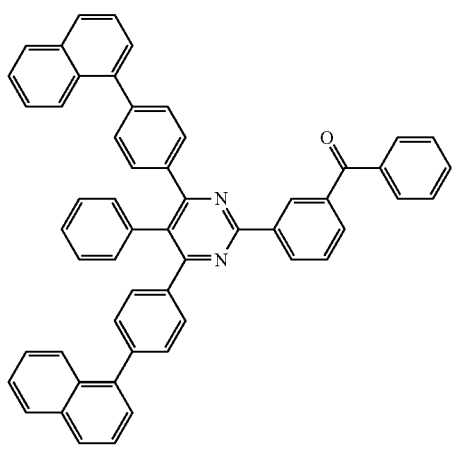
formula (416)
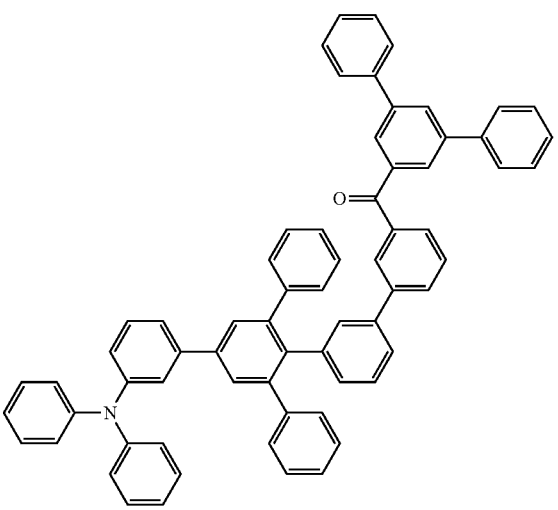
formula (417)
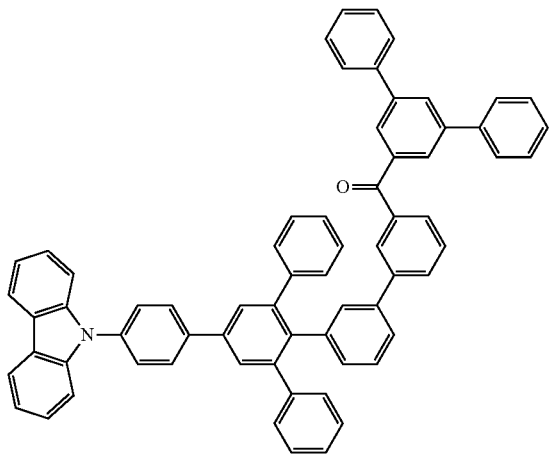
formula (418)
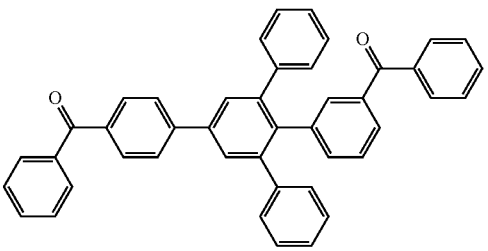

formula (419)
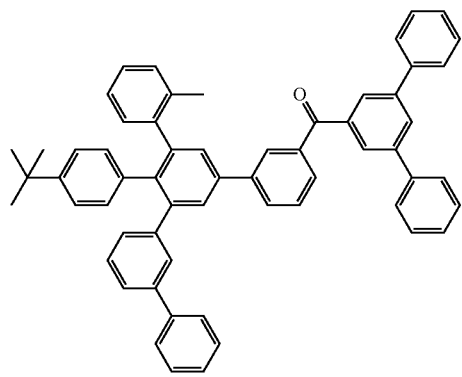
formula (420)
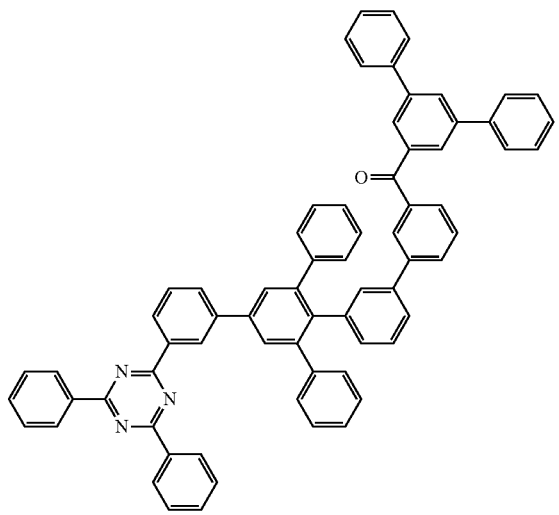
formula (421)
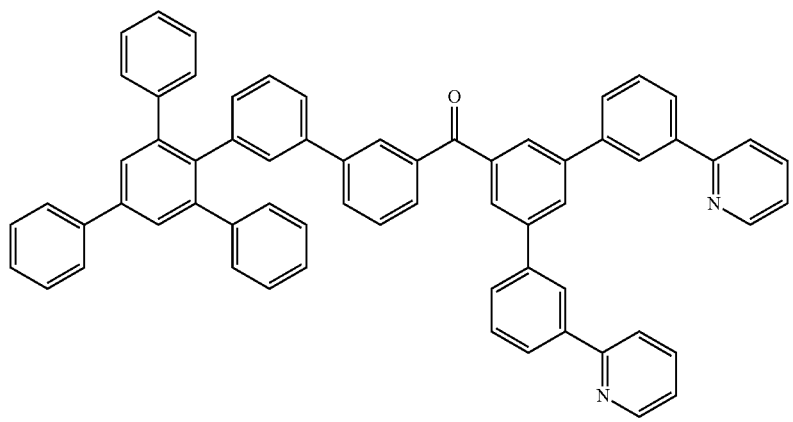
formula (422)
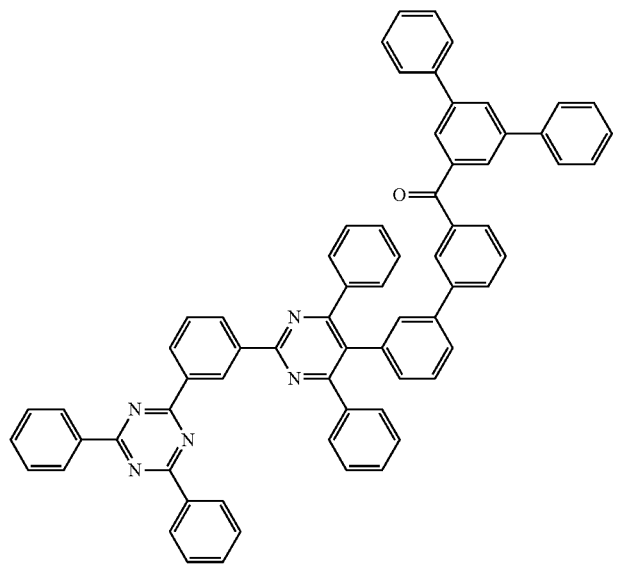

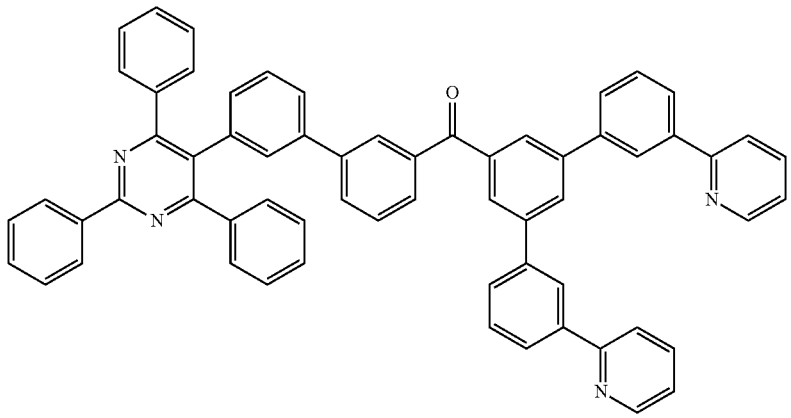

formula (423)

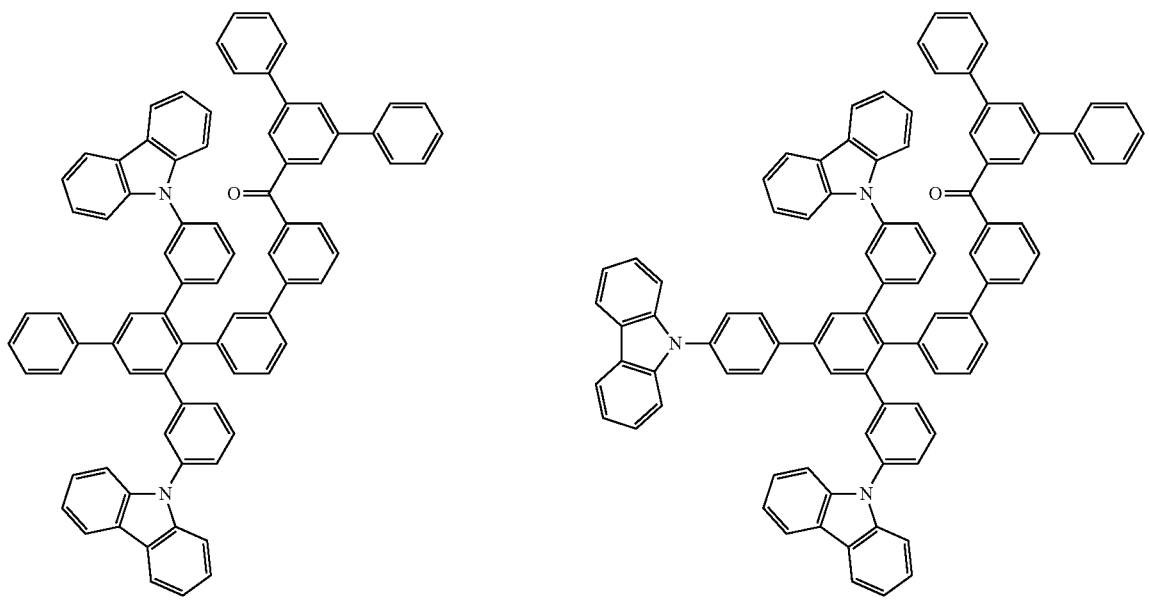

formula (424)

formula (425)

The compounds of the formula (1) can be used in an electronic device. An electronic device here is taken to mean a device which comprises at least one layer which comprises at least one organic compound. However, the component here may also comprise inorganic materials or also layers built up entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers), "organic plasmon emitting devices" (D. M. Koller et al., Nature Photonics 2008, 1-4) and electrophotography devices, preferably organic electroluminescent devices (OLEDs), particularly preferably phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers and/or charge-generation layers. It is likewise possible for interlayers, which have, for example, an exciton-blocking function, to be introduced between two emitting layers. However, it should be pointed out that each of these layers does not necessarily have to be present. A possible layer structure is, for example, the following: cathode/EML/interlayer/buffer layer/anode, where EML represents the emitting layer. The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013). Furthermore, an optical coupling-out layer may be applied to one or both of the electrodes.

The compound in accordance with the above-mentioned embodiments can be employed in various layers, depending on the precise structure. Preference is given to an organic electroluminescent device comprising one of the compounds of the formula (1) as host or matrix for fluorescent or phosphorescent emitters, in particular for phosphorescent emitters, and/or in a hole-blocking layer and/or in an electron-transport layer and/or in an electron-blocking or exciton-blocking layer and/or in a hole-transport layer and/or in an optical coupling-out layer. The above-mentioned preferred embodiments also apply to the use of the materials in organic electronic devices.

In a preferred embodiment of the invention, the compound of the formula (1) as host or matrix material for a fluorescent or phosphorescent compound in an emitting layer. The organic electroluminescent device here may comprise one emitting layer or a plurality of emitting layers, where at least one emitting layer comprises at least one compound according to the invention as host or matrix material.

If the compound of the formula (1) is employed as matrix material for an emitting compound in an emitting layer, it is preferably employed in combination with one or more phosphorescent materials (triplet emitters). Phosphorescence in the sense of this invention is taken to mean the luminescence from an excited state of relatively high spin multiplicity, i.e. a spin state>1, very preferably from an excited triplet and/or quintet state and very particularly preferably from a triplet state. For the purposes of this application, all luminescent complexes containing metals from the second and third transition-metal series, in particular all iridium and platinum complexes, and all luminescent copper complexes are to be regarded as phosphorescent compounds.

A further preferred embodiment of the present invention is the use of the compound of the formula (1) as matrix material for a phosphorescent emitter in combination with a further matrix material. Particularly suitable matrix materials which can be employed in combination with the compounds of the formula (1) according to the invention are aromatic ketones, aromatic phosphine oxides or aromatic sulfoxides or sulfones, for example in accordance with WO 2004/013080, WO 2004/093207, WO 2006/005627 or WO 2010/006680, triarylamines, carbazole derivatives, for example CBP (N,N-bis-carbazolylbiphenyl) or the carbazole derivatives disclosed in WO 2005/039246, US 2005/0069729, JP 2004/288381, EP 1205527 or WO 2008/086851, indolocarbazole derivatives, for example in accordance with WO 2007/063754 or WO 2008/056746, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, diazasilole or tetraazasilole derivatives, for example in accordance with the unpublished application DE 102008056688.8, diazaphosphole derivatives, for example in accordance with the unpublished application DE 102009022858.6, or indenocarbazole derivatives, for example in accordance with the unpublished applications DE 102009023155.2 and DE 102009031021.5.

Preference is furthermore given for the purposes of the present invention to mixtures consisting of more than two matrix materials, where at least one of the matrix materials is one of the compounds according to the invention. Further matrix materials which can be employed in combination with the compounds according to the invention are in principle all matrix materials, where preferred matrix materials are those mentioned above.

Finally, mixtures comprising two or more of the compounds according to the invention as matrix material are very particularly preferred.

Suitable phosphorescent compounds (triplet emitters) are, in particular, compounds which emit light o radiation, for example in the visible region and/or ultraviolet region and/or in the infrared region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

The matrix materials according to the invention or the mixtures described above comprising one or more of the matrix materials according to the invention can be employed as matrix material for individual emitters or for mixtures of emitters.

In general, all phosphorescent complexes as are used in accordance with the prior art for phosphorescent OLEDs and as are known to the person skilled in the art in the area of organic electroluminescence are suitable, and the person skilled in the art will be able to use further fluorescent compounds without inventive step.

Phosphorescent metal complexes preferably contain Ir, Ru, Pd, Pt, Os or Re. Preferred ligands for phosphorescent metal complexes are 2-phenylpyridine derivatives, 7,8-benzoquinoline derivatives, 2-(2-thienyl)pyridine derivatives, 2-(1-naphthyl)pyridine derivatives or 2-phenylquinoline derivatives. All these compounds may be substituted, for example by fluoro, cyano and/or trifluoromethyl substituents for blue. Auxiliary ligands are preferably acetylacetonate or picolinic acid.

Particularly suitable are complexes of Pt or Pd with tetradentate ligands, (US 2007/0087219), Pt-porphyrin complexes having an enlarged ring system (US2009/0061681 A1) and Ir complexes, for example 2,3,7,8,12,13,17,18-octaethyl-21H,23H-porphyrin-Pt(II), tetraphenyl-Pt(II) tetrabenzoporphyrin (US 2009/0061681), cis-bis(2-phenylpyridinato-N, $C^{2'}$)Pt(II), cis-bis(2-(2'-thienyl)pyridinato-N,$C^{3'}$)Pt(II), cis-bis(2-(2'-thienyl)quinolinato-N,$C^{5'}$)Pt(II), (2-(4,6-difluorophenyl)pyridinato-N,$C^{2'}$)Pt(II) (acetylacetonate), or tris(2-phenylpyridinato-N,$C^{2'}$)Ir(III) (=Ir(ppy)$_3$, green), bis(2-phenylpyridinato-N,$C^{2'}$)Ir(III) (acetylacetonate) (=Ir(ppy)$_2$ acetylacetonate, green, US 2001/0053462 A1, Baldo, Thompson et al. *Nature* 403, (2000), 750-753), bis(1-phenylisoquinolinato-N,$C^{2'}$)(2-phenylpyridinato-N,$C^{2'}$)iridium (III), bis(2-phenylpyridinato-N,$C^{2'}$)(1-phenylisoquinolinato-N,$C^{2'}$)iridium(II), bis(2-(2'-benzothienyl)pyridinato-N,$C^{3'}$)iridium(III) (acetylacetonate), bis(2-(4',6'-difluorophenyl)pyridinato-N,$C^{2'}$)iridium(III) (piccolinate) (FIrpic, blue), bis(2-(4',6'-difluorophenyl)pyridinato-N,$C^{2'}$)Ir(III) (tetrakis(1-pyrazolyl)borate), tris(2-(biphenyl-3-yl)-4-tert-butylpyridine)iridium(III), (ppz)$_2$Ir(5phdpym) (US 2009/0061681 A1), (45ooppz)$_2$Ir(5phdpym) (US 2009/

0061681 A1), derivatives of 2-phenylpyridine-Ir complexes, such as, for example, PQIr (=iridium(III) bis(2-phenylquinolyl-N,C$^{2'}$)acetylacetonate), tris(2-phenylisoquinolinato-N,C)Ir(III) (red), bis(2-(2'-benzo[4,5-a]thienyl)pyridinato-N,C$^3$)Ir (acetylacetonate) ([Btp$_2$Ir(acac)], red, Adachi et al. *Appl. Phys. Lett.* 78 (2001), 1622-1624).

Likewise suitable are complexes of trivalent lanthanides, such as, for example, Tb$^{3+}$ and Eu$^{3+}$ (J. Kido et al. *Appl. Phys. Lett.* 65 (1994), 2124, Kido et al. Chem. Lett. 657, 1990, US 2007/0252517 A1) or phosphorescent complexes of Pt(II), Ir(I), Rh(I) with maleonitriledithiolate (Johnson et al., *JACS* 105, 1983, 1795), Re(I) tricarbonyl-diimine complexes (Wrighton, *JACS* 96, 1974, 998, inter alia), Os(II) complexes with cyano ligands and bipyridyl or phenanthroline ligands (Ma et al., *Synth. Metals* 94, 1998, 245).

Further phosphorescent emitters having tridentate ligands are described in U.S. Pat. No. 6,824,895 and U.S. Ser. No. 10/729,238. Red-emitting phosphorescent complexes are found in U.S. Pat. No. 6,835,469 and U.S. Pat. No. 6,830,828.

If the compound of the formula (1) according to the invention is employed as host material for an emitting compound in an emitting layer, it is preferably employed in combination with one or more fluorescent materials (singlet emitters). Fluorescence in the sense of this invention is taken to mean the luminescence from an excited state having low spin multiplicity, i.e. from a spin state S=1.

A further preferred embodiment of the present invention is the use of the compounds of the formula (1) according to the invention as host material for a fluorescent emitter in combination with a further host material. Particularly suitable host materials which can be employed in combination with the compounds of the formula (1) are selected from the classes of the oligoarylenes (for example 2,2',7,7-tetraphenylspirobifluorene in accordance with EP 676461 or dinaphthylanthracene), in particular the oligoarylenes containing condensed aromatic groups, such as, for example, anthracene, benzanthracene, benzophenanthrene (DE 102009005746.3, WO 2009/069566), phenanthrene, tetracene, coronene, chrysene, fluorene, spirofluorene, perylene, phthaloperylene, naphthaloperylene, decacyclene, rubrene, the oligoarylenevinylenes (for example DPVBi=4,4'-bis(2,2-diphenylethenyl)-1,1'-biphenyl) or spiro-DPVBi in accordance with EP 676461), the polypodal metal complexes (for example in accordance with WO 2004/081017), in particular metal complexes of 8-hydroxyquinoline, for example Alq$_3$ (=aluminium(III) tris(8-hydroxyquinoline)) or bis(2-methyl-8-quinolinolato)-4-(phenylphenolinolato)aluminium, also with imidazole chelate (US 2007/0092753 A1) and the quinoline/metal complexes, aminoquinoline/metal complexes, benzoquinoline/metal complexes, the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with DE 102007024850, WO 2008/145239).

Particularly preferred host materials are selected from the classes of the oligoarylenes, comprising naphthalene, anthracene, benzanthracene and/or pyrene or atropisomers of these compounds, the ketones, the phosphine oxides and the sulfoxides. Very particularly preferred host materials are selected from the classes of the oligoarylenes, comprising anthracene, benzanthracene and/or pyrene or atropisomers of these compounds. An oligoarylene in the sense of this invention is intended to be taken to mean a compound in which at least three aryl or arylene groups are bonded to one another.

Preference is furthermore given for the purposes of the present invention to mixtures consisting of more than two host materials, where at least one of the host materials is one of the compounds according to the invention. Further host materials which can be employed in combination with the compounds according to the invention are in principle all host materials, where preferred host materials are those mentioned above.

Finally, mixtures comprising two or more of the compounds according to the invention as host material are very particularly preferred.

Suitable fluorescent compounds (singlet emitters) are, in particular, compounds which emit light or radiation on suitable excitation, for example in the visible region and/or ultraviolet region and/or in the infrared region.

Preferred dopants (emitters) are selected from the class of the monostyrylamines, the distyrylamines, the tristyrylamines, the tetrastyrylamines, the styrylphosphines, the styryl ethers and the arylamines.

A monostyrylamine is taken to mean a compound which contains one substituted or unsubstituted styryl group and at least one, preferably aromatic, amine. A distyrylamine is taken to mean a compound which contains two substituted or unsubstituted styryl groups and at least one, preferably aromatic, amine. A tristyrylamine is taken to mean a compound which contains three substituted or unsubstituted styryl groups and at least one, preferably aromatic, amine. A tetrastyrylamine is taken to mean a compound which contains four substituted or unsubstituted styryl groups and at least one, preferably aromatic, amine. The styryl groups are particularly preferably stilbenes, which may also be further substituted. Corresponding phosphines and ethers are defined analogously to the amines. An arylamine or an aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 2,6- or 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Further preferred dopants are selected from indenofluorenamines or indenofluorenediamines, for example in accordance with WO 2006/122630, benzoindenofluorenamines or benzoindenofluorenediamines, for example in accordance with WO 08/006,449, and dibenzoindenofluorenamines or dibenzoindenofluorenediamines, for example in accordance with WO 07/140,847.

Examples of dopants from the class of the styrylamines are substituted or unsubstituted tristilbenamines or the dopants described in WO 2006/000388, WO 2006/058737, WO 2006/000389, WO 2007/065549 and WO 2007/115610. Distyrylbenzene and distyrylbiphenyl derivatives are described in U.S. Pat. No. 5,121,029. Further styrylamines can be found in US 2007/0122656 A1.

Further preferred dopants are selected from derivatives of naphthalene, anthracene, tetracene, benzanthracene, benzophenanthrene (DE 102009 005746.3), fluorene, fluoranthene, periflanthene, indenoperylene, phenanthrene, perylene (US 2007/0252517), pyrene, chrysene, decacyclene, coronene, tetraphenylcyclopentadiene, pentaphenylcyclopentadiene, fluorene, spirofluorene, rubrene, coumarine (U.S. Pat. No. 4,769,292, U.S. Pat. No. 6,020,078, US 2007/0252517), pyran, oxazole, benzoxazole, benzothiazole, benzimidazole, pyrazine, cinnamic acid esters, diketopyrrolopyrrole, acridone and quinacridone (US 2007/0252517).

Of the anthracene compounds, particular preference is given to 9,10-substituted anthracenes, such as, for example, 9,10-diphenylanthracene and 9,10-bis(phenylethynyl)anthracene. 1,4-Bis(9'-ethynylanthracenyl)benzene is also a preferred dopant.

Preference is likewise given to derivatives of rubrene, coumarine, rhodamine, quinacridone, such as, for example, DMQA (=N,N'-dimethylquinacridone), dicyanomethylenepyran, such as, for example, DCM (=4-(dicyanoethylene)-6-(4-dimethylaminostyryl-2-methyl)-4H-pyran), thiopyran, polymethine, pyrylium and thiapyrylium salts, periflanthene and indenoperylene.

Blue fluorescent emitters are preferably polyaromatic compounds, such as, for example, 9,10-di(2-naphthylanthracene) and other anthracene derivatives, derivatives of tetracene, xanthene, perylene, such as, for example, 2,5,8,11-tetra-t-butylperylene, phenylene, for example 4,4'-bis(9-ethyl-3-carbazovinylene)-1,1'-biphenyl, fluorene, fluoranthene, arylpyrenes (U.S. Ser. No. 11/097,352), arylenevinylenes (U.S. Pat. No. 5,121,029, U.S. Pat. No. 5,130,603), derivatives of rubrene, coumarine, rhodamine, quinacridone, such as, for example, DMQA, dicyanomethylenepyran, such as, for example, DCM, thiopyrans, polymethine, pyrylium and thiapyrylium salts, periflanthene, indenoperylene, bis(azinyl)imine-boron compounds (US 2007/0092753 A1), bis(azinyl)methene compounds and carbostyryl compounds.

Further preferred blue fluorescent emitters are described in C. H. Chen et al.: "Recent developments in organic electroluminescent materials" Macromol. Symp. 125, (1997) 1-48 and "Recent progress of molecular organic electroluminescent materials and devices" Mat. Sci. and Eng. R, 39 (2002), 143-222.

Further preferred blue-fluorescent emitters are the hydrocarbons disclosed in the application DE 102008035413.

The host materials according to the invention or the mixtures described above comprising one or more of the host materials according to the invention can be employed as host material for individual emitters or for mixtures of emitters.

The mixture of the compound(s) according to the invention and the emitting (fluorescent and/or phosphorescent) compound comprises between 99 and 1% by weight, preferably between 98 and 10% by weight, particularly preferably between 97 and 60% by weight, in particular between 95 and 80% by weight, of the compound of the formula (1), based on the entire mixture comprising emitter and matrix or host material. Correspondingly, the mixture comprises between 1 and 99% by weight, preferably between 2 and 90% by weight, particularly preferably between 3 and 40% by weight, in particular between 5 and 20% by weight, of the emitter, based on the entire mixture comprising emitter and matrix or host material.

In a further embodiment of the invention, the organic electroluminescent device according to the invention does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer directly adjacent to the emitting layer as hole-transport or hole-injection material, as described, for example, in WO 2009/030981.

In a further preferred embodiment of the invention, the compound of the formula (1) is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, Liq (lithium hydroxyquinolinate), or with alkali-metal salts, such as, for example, LiF.

In still a further preferred embodiment of the invention, the compounds of the formula (1) according to the invention are employed in a hole-blocking layer. A hole-blocking layer is taken to mean a layer which is directly adjacent to an emitting layer on the cathode side.

In still a further embodiment of the invention, the compounds of the formula (1) are employed in a hole-transport layer or in an electron-blocking layer or exciton-blocking layer.

It is furthermore possible to use the compounds of the formula (1) both in a hole-blocking layer or electron-transport layer and also as matrix in an emitting layer or both in a hole-transport layer or exciton-blocking layer and also as matrix in an emitting layer.

In the further layers of the organic electroluminescent device according to the invention, all materials as are usually employed in accordance with the prior art can be used. The person skilled in the art will therefore be able to employ, without inventive step, all materials known for organic electroluminescent devices in combination with the compounds of the formula (1) according to the invention.

The present invention therefore also relates to compositions comprising at least one of the compounds according to the invention and a further organically functional material selected from the group of the emitters, host materials, matrix materials, electron-transport materials (ETM), electron-injection materials (EIM), hole-transport materials (HTM), hole-injection materials (HIM), electron-blocking materials (EBM), hole-blocking materials (HBM), exciton-blocking materials (ExBM), particularly preferably emitters and very particularly preferably fluorescent and/or phosphorescent emitters.

Preference is furthermore given to an organic electroluminescent device, characterised in that one or more layers are coated by means of a sublimation process, in which the materials are vapour-deposited in vacuum sublimation units at an initial pressure of less than $10^{-5}$ mbar, preferably less than $10^{-6}$ bar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), ink-jet printing or nozzle printing. Soluble compounds, which are obtained, for example, by suitable substitution, are necessary for this purpose. These processes are also suitable, in particular, for oligomers, dendrimers and polymers.

A further embodiment of the present invention relates to formulations comprising one or more of the compounds according to the invention and one or more solvents. The formulation is highly suitable for the production of layers from solution.

Suitable and preferred solvents are, for example, toluene, anisole, xylenes, methyl benzoate, dimethylanisoles, trimethylbenzenes, tetralin, veratrols, tetrahydrofuran, chlorobenzene or dichlorobenzenes and mixtures thereof.

Likewise possible are hybrid processes, in which, for example, one or more layers are applied from solution and one or more other layers are applied by vacuum vapour deposition.

These processes are generally known to the person skilled in the art and can be applied by him without inventive step to organic electroluminescent devices comprising the compounds according to the invention.

The organic electroluminescent device according to the invention can be used, for example, in displays or for lighting purposes, but also for medical or cosmetic applications.

The invention therefore furthermore relates to the use of the compounds according to the invention in an electronic device.

The compounds according to the invention are suitable for use in light-emitting devices. These compounds can thus be employed in a very versatile manner. Some of the main areas of application here are display or lighting technologies. It is furthermore particularly advantageous to employ the compounds and devices comprising these compounds in the area of phototherapy.

The present invention therefore furthermore relates to the use of the compounds according to the invention and devices comprising the compounds for the treatment, prophylaxis and diagnosis of diseases. The present invention still furthermore relates to the use, of the compounds according to the invention and devices comprising the compounds for the treatment and prophylaxis of cosmetic conditions.

The present invention furthermore relates to the compounds according to the invention for the production of devices for the therapy, prophylaxis and/or diagnosis of therapeutic diseases.

Many diseases are associated with cosmetic aspects. Thus, a patient with severe acne on the face suffers not only from the medical causes and consequences of the disease, but also from the cosmetic accompanying circumstances.

Phototherapy or light therapy is used in many medical and/or cosmetic areas. The compounds according to the invention and the devices comprising these compounds can therefore be employed for the therapy and/or prophylaxis and/or diagnosis of all diseases and/or in cosmetic applications for which the person skilled in the art considers the use of phototherapy. Besides irradiation, the term phototherapy also includes photodynamic therapy (PDT) as well as disinfection and sterilisation in general. It is not only humans or animals that can be treated by means of phototherapy or light therapy, but also any other type of living or non-living materials. These include, for example, fungi, bacteria, microbes, viruses, eukaryotes, pro-karyonts, foods, drinks, water and drinking water.

The term phototherapy also includes any type of combination of light therapy and other types of therapy, such as, for example, treatment with active compounds. Many light therapies have the aim of irradiating or treating exterior parts of an object, such as the skin of humans and animals, wounds, mucous membranes, the eye, hair, nails, the nail bed, gums and the tongue. In addition, the treatment or irradiation according to the invention can also be carried out inside an object in order, for example, to treat internal organs (heart, lung, etc.) or blood vessels or the breast.

The therapeutic and/or cosmetic areas of application according to the invention are preferably selected from the group of skin diseases and skin-associated diseases or changes or conditions, such as, for example, psoriasis, skin ageing, skin wrinkling, skin rejuvenation, enlarged skin pores, cellulite, oily/greasy skin, folliculitis, actinic keratosis, precancerous actinic keratosis, skin lesions, sun-damaged and sun-stressed skin, crows' feet, skin ulcers, acne, acne rosacea, scars caused by acne, acne bacteria, photomodulation of greasy/oily sebaceous glands and their surrounding tissue, jaundice, jaundice of the newborn, vitiligo, skin cancer, skin tumours, Crigler-Najjar, dermatitis, atopic dermatitis, diabetic skin ulcers, and desensitisation of the skin.

Particular preference is given for the purposes of the invention to the treatment and/or prophylaxis of psoriasis, acne, cellulite, skin wrinkling, skin ageing, icterus and vitiligo.

Further areas of application according to the invention for the compositions and/or devices comprising the compositions according to the invention are selected from the group of inflammatory diseases, rheumatoid arthritis, pain therapy, treatment of wounds, neurological diseases and conditions, oedema, Paget's disease, primary and metastasising tumours, connective-tissue diseases or changes, changes in the collagen, fibroblasts and cell level originating from fibroblasts in tissues of mammals, irradiation of the retina, neovascular and hypertrophic diseases, allergic reactions, irradiation of the respiratory tract, sweating, ocular neovascular diseases, viral infections, particularly infections caused by herpes simplex or HPV (human papillomaviruses) for the treatment of warts and genital warts.

Particular preference is given for the purposes of the invention to the treatment and/or prophylaxis of rheumatoid arthritis, viral infections and pain.

Further areas of application according to the invention for the compounds and/or devices comprising the compounds according to the invention are selected from winter depression, sleeping sickness, irradiation for improving the mood, the reduction in pain particularly muscular pain caused by, for example, tension or joint pain, elimination of the stiffness of joints and the whitening of the teeth (bleaching).

Further areas of application according to the invention for the compounds and/or devices comprising the compounds according to the invention are selected from the group of disinfections. The compounds according to the invention and/or the devices according to the invention can be used for the treatment of any type of objects (non-living materials) or subjects (living materials such as, for example, humans and animals) for the purposes of disinfection, sterilisation or preservation. This includes, for example, the disinfection of wounds, the reduction in bacteria, the disinfection of surgical instruments or other articles, the disinfection or preservation of foods, of liquids, in particular water, drinking water and other drinks, the disinfection of mucous membranes and gums and teeth. Disinfection here is taken to mean the reduction in the living microbiological causative agents of undesired effects, such as bacteria and germs.

For the purposes of the phototherapy mentioned above, devices comprising the compounds according to the invention preferably emit light having a wavelength between 250 and 1250 nm, particularly preferably between 300 and 1000 nm and especially preferably between 400 and 850 nm.

In a particularly preferred embodiment of the present invention, the compounds according to the invention are employed in an organic light-emitting diode (OLED) or an organic light-emitting electrochemical cell (OLEC) for the purposes of phototherapy. Both the OLED and the OLEC can have a planar or fibre-like structure having any desired cross section (for example round, oval, polygonal, square) with a single- or multilayered structure. These OLECs and/or OLEDs can be installed in other devices which comprise further mechanical, adhesive and/or electronic elements (for example battery and/or control unit for adjustment of the irradiation times, intensities and wavelengths). These devices comprising the OLECs and/or OLEDs according to the invention are preferably selected from the group comprising plasters, pads, tapes, bandages, cuffs, blankets, caps, sleeping bags, textiles and stents.

The use of the said devices for the said therapeutic and/or cosmetic purpose is particularly advantageous compared with the prior art, since homogeneous irradiation of lower irradiation intensity is possible at virtually any site and at any time of day with the aid of the devices according to the invention using the OLEDs and/or OLECs. The irradiation can be carried out as an inpatient, as an outpatient and/or by the patient themselves, i.e. without initiation by medical or cosmetic specialists. Thus, for example, plasters can be worn under clothing, so that irradiation is also possible during working hours, in leisure time or during sleep. Complex inpatient/outpatient treatments can in many cases be avoided or their frequency reduced. The devices according to the invention may be intended for reuse or be disposable articles, which can be disposed of after use once, twice or three times.

Further advantages over the prior art are, for example, lower evolution of heat and emotional aspects. Thus, newborn being treated owing to jaundice typically have to be irradiated blindfolded in an incubator without physical contact with the parents, which represents an emotional stress situation for parents and newborn. With the aid of a blanket according to the invention comprising the OLEDs and/or OLECs according to the invention, the emotional stress can be reduced significantly. In addition, better temperature control of the child is possible due to reduced heat production of the devices according to the invention compared with conventional irradiation equipment.

The compounds according to the invention and the electronic devices according to the invention, in particular organic electroluminescent devices, are distinguished by the following surprising advantages over the prior art:

1. The compounds according to the invention or compounds of the formula (1) employed as host or matrix material for fluorescent or phosphorescent emitters result in very high efficiencies and long lifetimes. This applies, in particular, if the compounds are employed as matrix material for a phosphorescent emitter.

2. The compounds according to the invention or compounds of the formula (1) are not only suitable as matrix for green- and red-phosphorescent compounds, but instead also for blue-phosphorescent compounds.

3. The compounds according to the invention or compounds of the formula (1) also exhibit good properties on use as electron-transport material.

4. In contrast to many compounds in accordance with the prior art which exhibit partial or complete pyrolytic decomposition on sublimation, the compounds according to the invention have high thermal stability.

5. The compounds according to the invention, employed in organic electroluminescent devices, result in high efficiencies and in steep current/voltage curves with low use voltages.

These above-mentioned advantages are not accompanied by an impairment of the other electronic properties.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

All features of the present invention can be combined with one another in any way, unless certain features and/or steps are mutually exclusive. This applies, in particular, to preferred features of the present invention. Equally, features of non-essential combinations can be used separately (and not in combination).

It should furthermore be pointed out that many of the features, and in particular those of the preferred embodiments of the present invention, should be regarded as inventive themselves and not merely as part of the embodiments of the present invention. Independent protection may be granted for these features in addition or as an alternative to each invention claimed at present.

The teaching regarding technical action disclosed with the present invention can be abstracted and combined with other examples.

The invention is explained in greater detail by the following examples without wishing it to be restricted thereby.

EXAMPLES

The following syntheses are carried out, unless indicated otherwise, under a protective-gas atmosphere in dried solvents. Starting materials (I), (III), (VI), (VII) and (XIII) are commercially available (Sigma-Aldrich, Alessa Syntec, VWR, Carbone Scientific Co., Ltd).

Example 1
Preparation of Compounds (II), (IV), (V), (VIII), (IX) and (X)
Synthetic Procedure for the Preparation of Compound (X):
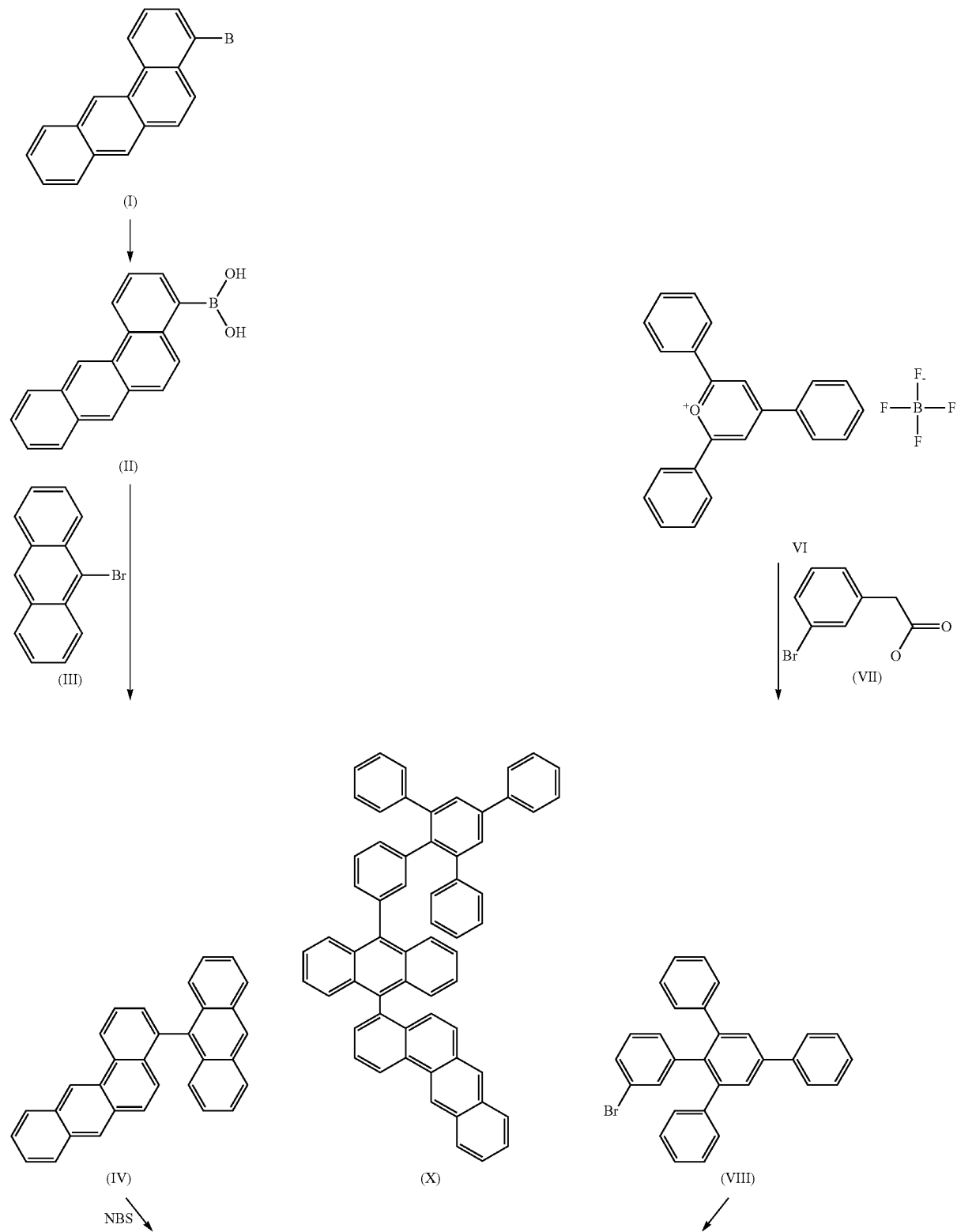

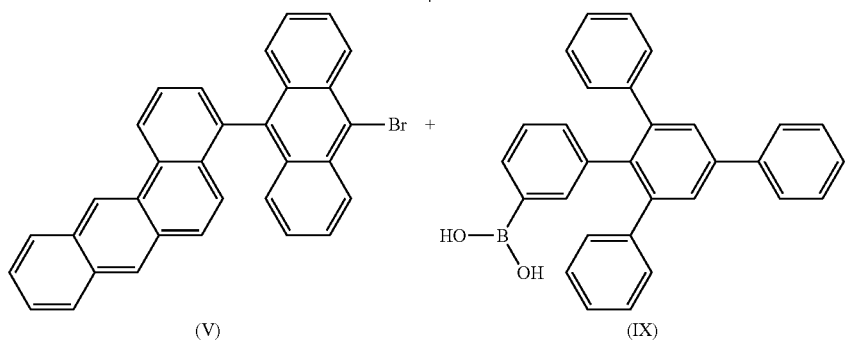

a) Synthesis of Compound (II)

52 ml (130 mmol) of n-butyllithium (2.5 M in n-hexane) are added dropwise with vigorous stirring to a suspension of 30.7 g (100 mmol) of 4-bromo-benz[a]anthracene (I) in 1000 ml of THF at −78° C., and the mixture is stirred for a further 2 h. 16.7 ml (150 mmol) of trimethyl borate are added in one portion to the red solution with vigorous stirring, the mixture is stirred at −78° C. for a further 30 min., then warmed to room temperature over the course of 3 h, 300 ml of water are added, and the mixture is stirred for 30 min. The organic phase is separated off and evaporated to dryness in vacuo. The solid is taken up in 100 ml of n-hexane, filtered off with suction, washed once with 100 ml of n-hexane and dried in vacuo. Yield: 23.7 g (87.0 mmol), 87.0%, purity about 90.0% (NMR) of boronic acid, with varying amounts of boronic anhydride and borinic acid. The boronic acid can be used in this form without further purification.

b) Synthesis of Compound (IV)

25.0 g (97.2 mmol) of 9-bromoanthracene (III), 27.0 g (99.2 mmol) of benz[a]anthracene-4-boronic acid (II) and 44.5 g (210 mmol) of tripotassium phosphate are suspended in 500 ml of toluene, 600 ml of water and 100 ml of dioxane. 1.83 g (6.01 mmol) of tri-o-tolylphosphine and then 225 mg (1.00 mmol) of palladium(II) acetate are added to this suspension, and the mixture is subsequently heated under reflux for 16 h. After cooling, the organic phase is separated off, washed three times with 500 ml of water, dried using sodium sulfate and subsequently evaporated to dryness. The solid is recrystallised from 300 ml of toluene and finally dried under reduced pressure. The yield is 26.2 g (64.8 mmol), corresponding to 64.8% of theory.

c) Synthesis of Compound (V)

1.30 g (8.02 mmol) of iron(III) chloride and then 13.3 g (74.7 mmol) of N-bromosuccinimide are added to a suspension, cooled to 0° C., of 26.0 g (64.3 mmol) of compound (IV) in 600 ml of chloroform, and the mixture is stirred at 0° C. for 4 h. After warming to room temperature, 400 ml of water are added, the organic phase is separated off, washed three times with 300 ml of water, dried using sodium sulfate and subsequently evaporated to dryness. The orange solid obtained is recrystallised from toluene and finally dried under reduced pressure. The yield is 23.7 g (49.0 mmol), corresponding to 76.6% of theory.

d) Synthesis of Compound (VIII)

8.60 g (159 mmol) of sodium methoxide are stirred for 30 min in 86 ml of methanol with 33.0 g (153 mmol) of 3-bromophenylacetic acid (VII) and subsequently evaporated to dryness. The 3-bromobenzoate formed is refluxed for 4 h with 30.4 g (76.7 mmol) of 2,4,6-triphenylpyrylium tetrafluoroborate (VI) in 165 ml of acetic anhydride. After cooling, the acetic anhydride is removed by distillation, the residue is taken up in 400 ml of dichloromethane and washed twice with 200 ml of water each time, dried using sodium sulfate and subsequently evaporated to dryness. The dark-green liquid is filtered through silica gel with a heptane/ethyl acetate mixture (9:1), corresponding fractions are evaporated to dryness. The orange solid obtained is recrystallised from ethanol and finally dried under reduced pressure. The yield is 18.1 g (39.2 mmol), corresponding to 51.1% of theory.

e) Synthesis of Compound (IX)

8.80 ml (22.0 mmol) of n-butyllithium (2.5 M in n-hexane) are added dropwise with vigorous stirring to a suspension of 10.0 g (21.7 mmol) of compound (VIII) in 500 ml of THF at −78° C., and the mixture is stirred for a further 1 h. 5.10 ml (22.2 mmol) of triisopropyl borate are added in one portion to the solution with vigorous stirring, the mixture is stirred at −78° C. for a further 2 h, then warmed to room temperature over the course of 1 h. After cooling to 0° C., 200 ml of 0.2 N hydrochloric acid are added dropwise, and 300 ml of ethyl acetate are added. The aqueous phase is separated off, extracted twice with 200 ml of ethyl acetate, the combined organic phases are washed once with 200 ml of water, once with 200 ml of saturated sodium hydrogencarbonate solution and once with 200 ml of saturated sodium chloride solution, dried using sodium sulfate and subsequently evaporated to dryness. The colourless solid obtained is stirred in a hot heptane/toluene mixture, filtered off with suction and finally dried under reduced pressure. The yield is 7.08 g (16.6 mmol), corresponding to 76.2% of theory.

f) Synthesis of Compound (X)

900 mg (1.86 mmol) of compound (V), 880 mg (2.06 mmol) of compound (IX) and 3.50 ml of a 2.0 M sodium carbonate solution (7.00 mmol) are suspended in 15 ml of toluene and 15 ml of ethanol. 30.0 mg (26.0 μmol) of tetrakis(triphenylphosphine)palladium(0) are added to this suspension, and the mixture is subsequently heated under reflux for 16 h. After cooling, the organic phase is separated off, washed three times with 20 ml of water and once with 20 ml of saturated sodium chloride solution, dried using sodium sulfate and subsequently evaporated to dryness. The residue is filtered through silica gel with a heptane/ethyl acetate mixture (9:1), corresponding fractions are evaporated to dryness. The solid obtained is recrystallised twice from a toluene/ethanol mixture and finally dried under reduced pressure. The yield is 1.18 g (1.50 mmol), corresponding to 78.7% of theory.

Example 2
Preparation of Compounds (XI), (XII) and (XIV) to (XVIII)
Synthetic Procedure for the Preparation of Compound (XVIII):
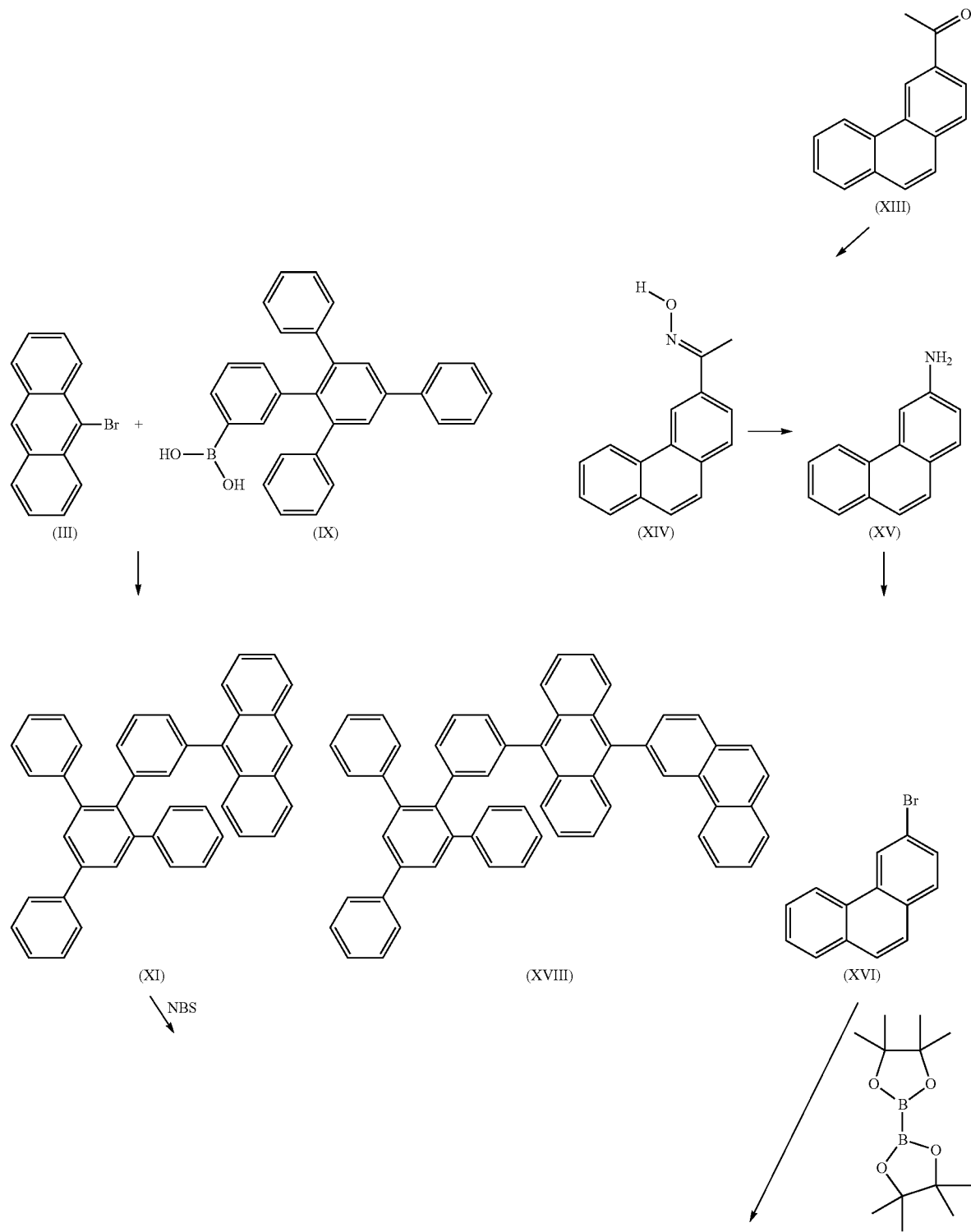

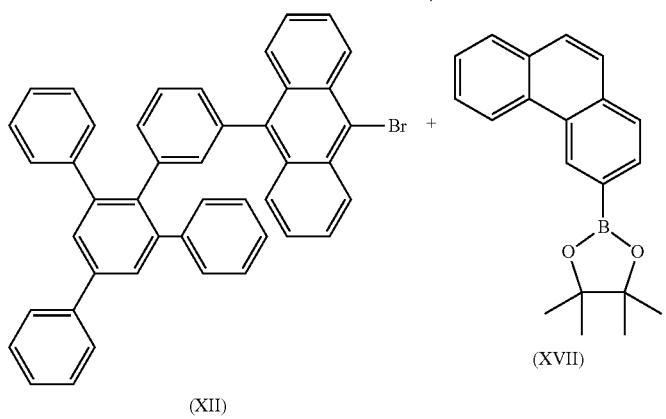

a) Synthesis of Compound (XI)

2.70 g (10.5 mmol) of 9-bromoanthracene (III), 5.00 g (11.7 mmol) of compound (IX) and 3.90 g (36.8 mmol) of sodium carbonate are suspended in 60 ml of toluene, 60 ml of ethanol and 14 ml of water. 130 mg (0.112 mmol) of tetrakis(triphenylphosphine)palladium(0) are added to this suspension, and the mixture is subsequently heated under reflux for 16 h. After cooling, the organic phase is separated off, washed three times with 50 ml of water, dried using sodium sulfate and subsequently evaporated to dryness. The solid is recrystallised from toluene and finally dried under reduced pressure. The yield is 5.19 g (9.29 mmol), corresponding to 88.5% of theory.

b) Synthesis of Compound (XII)

150 mg (0.925 mmol) of iron(III) chloride and then 1.90 g (10.7 mmol) of N-bromosuccinimide are added to a suspension, cooled to 0° C., of 5.00 g (8.95 mmol) of compound (XI) in 90 ml of chloroform, and the mixture is stirred at 0° C. for 2 h. After warming to room temperature, 100 ml of water are added, the organic phase is separated off, washed three times with 50 ml of water, dried using sodium sulfate and subsequently evaporated to dryness. The solid obtained is recrystallised from a heptane/ethyl acetate mixture and finally dried under reduced pressure. The yield is 4.30 g (6.74 mmol), corresponding to 75.4% of theory.

c) Synthesis of Compound (XIV)

200 g (908 mmol) of 3-acetylphenanthrene (XIII), 167 g (2.36 mol) of hydroxylammonium chloride and 257 ml (3.18 mmol) of pyridine are suspended in 800 ml of ethanol and refluxed at a bath temperature of 100° C. for 2 h. After cooling, 700 ml of ethyl acetate and 700 ml of water are added, the organic phase is separated off, washed three times with 500 ml of water, dried using sodium sulfate and subsequently evaporated to dryness. The residue is washed by stirring in 500 ml of ethanol and finally dried under reduced pressure. The yield is 160 g (682 mmol), corresponding to 75.1% of theory.

d) Synthesis of Compound (XV)

1.50 kg (15.3 mol) of polyphosphoric acid are heated to 100° C., 160 g (680 mmol) of compound (XIV) are added in portions over the course of one hour, and the mixture is stirred at 100° C. for a further 20 min. After cooling, 1000 ml of ice-water are carefully added, and the mixture is stirred at room temperature for 30 min. The solid formed is filtered off with suction, rinsed with water and dried under reduced pressure. 200 ml of 37% hydrochloric acid and 2.50 l of methanol are added to the solid, and the mixture is refluxed for 16 h. The majority of the methanol is removed under reduced pressure, the pale-green solid is filtered off with suction. This is suspended in 500 ml of water, neutralised using 300 ml of 30% NaOH solution and extracted three times with 300 ml of ethyl acetate each time. The combined organic phases are washed twice with 300 ml of water, dried using sodium sulfate and subsequently evaporated to dryness. The residue is filtered through silica gel with a heptane/ethyl acetate mixture (3:1), corresponding fractions are evaporated and finally dried under reduced pressure. The yield is 82.0 g (423 mmol), corresponding to 62.3% of theory.

e) Synthesis of Compound (XVI)

82.0 g (423 mmol) of phenanthren-3-ylamine (XV) and 95.0 g (425 mmol) of copper(II) bromide are suspended in 1.70 l of acetonitrile and cooled to 0° C. 100 ml (1.33 mol) of tert-butyl nitrite are added dropwise over the course of 45 min at such a rate that an internal temperature of 5° C. was not exceeded, and the mixture is stirred at 0° C. for a further 1 h. The batch is added to 1.50 kg of ice, stirred for a further 30 min, the dark-brown solid is filtered off with suction and discarded. 1000 ml of ethyl acetate are added to the mother liquor, the organic phase is separated off, washed twice with 500 ml of 2 N HCl each time and twice with 500 ml of water each time, dried using sodium sulfate and subsequently evaporated to dryness. The residue is filtered through silica gel with a heptane/ethyl acetate mixture (10:1), corresponding fractions are evaporated and finally dried under reduced pressure. The yield is 35.9 g (140 mmol), corresponding to 32.9% of theory.

f) Synthesis of Compound (XVII)

35.6 g (138 mmol) of 3-bromophenanthrene (XVI), 42.0 g (165 mmol) of bispinacolatodiboron and 46.0 g (469 mmol) of potassium acetate are suspended in 500 ml of dimethyl sulfoxide. 3.50 g (4.29 mmol) of 1,1-bis-(diphenylphosphino)ferrocenepalladium(II) dichloride*DCM are added to this suspension, and the reaction mixture is stirred at 80° C. for 6 h. After cooling, 1000 ml of ethyl acetate and 1000 ml of water are added, the organic phase is separated off, washed three times with 300 ml of water each time, dried using sodium sulfate and subsequently evaporated to dryness. The crude product is passed through a silica-gel column with a heptane/ethyl acetate mixture (10:1), corresponding fractions are evaporated and finally dried under reduced pressure. The yield is 38.5 g (127 mmol), corresponding to 92.0% of theory.

g) Synthesis of Compound (XVIII)

4.20 g (6.59 mmol) of compound (XII), 2.20 g (7.23 mmol) of compound (XVII) and 2.50 g (23.6 mmol) of sodium carbonate are suspended in 40 ml of toluene, 40 ml of ethanol and 10 ml of water. 100 mg (87.0 μmol) of tetrakis(triphenylphosphine)palladium(0) are added to this suspension, and the mixture is subsequently heated under reflux for 16 h. After cooling, the organic phase is separated off, washed three times with 50 ml of water and once with 50 ml of saturated sodium chloride solution, dried using sodium sulfate and subsequently evaporated to dryness. The residue is recrystallised from a heptane/toluene mixture and extracted with hot toluene. The yield is 4.08 g (5.55 mmol), corresponding to 84.3% of theory.

Example 3

Comparative Example

Preparation of Compound (XX)

Synthetic Procedure for the Preparation of Compound (XX)

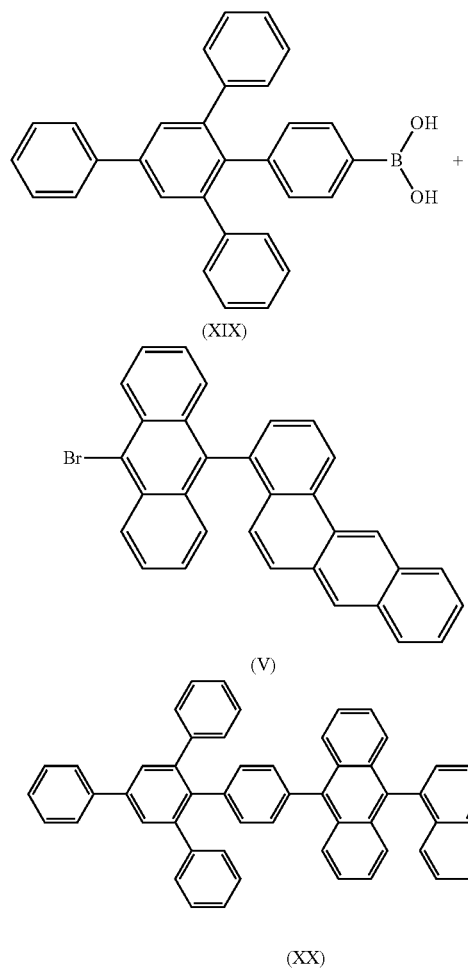

The synthesis of compound (XX) is carried out analogously to that of compound (X), with compound (IX) being replaced by 880 mg (2.06 mmol) of compound (XIX). The yield is 1.10 g (1.40 mmol), corresponding to 75.3% of theory.

Example 4

Comparative Example

Preparation of Compound (XXIV)

Synthetic Procedure for the Preparation of Compound (XXIV)

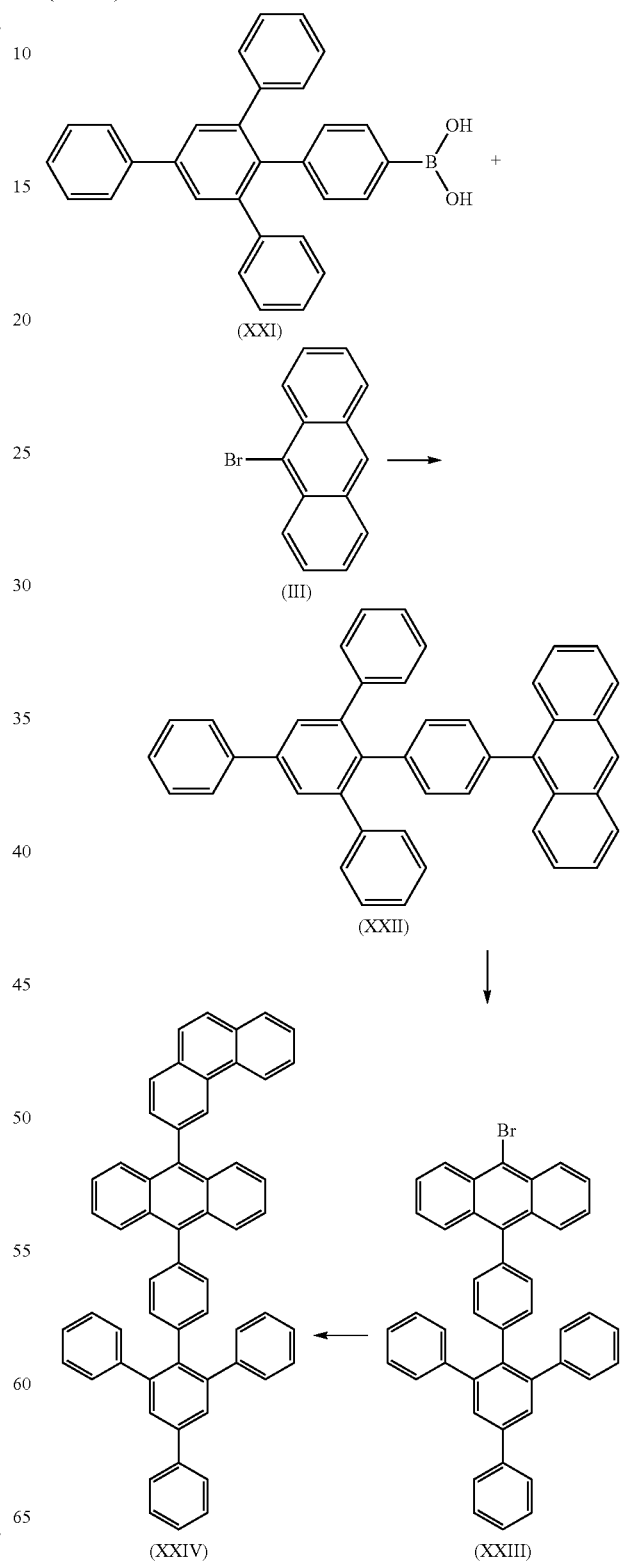

a) Synthesis of Compound (XXII)

The synthesis of compound (XXII) is carried out analogously to that of compound (XI), with compound (IX) being replaced by 5.00 g (11.7 mmol) of compound (XXI). The yield is 5.01 g (8.96 mmol), corresponding to 85.4% of theory.

b) Synthesis of Compound (XXIII)

The synthesis of compound (XXIII) is carried out analogously to that of compound (XII), with compound (XI) being replaced by 5.00 g (8.95 mmol) of compound (XXII). The yield is 4.46 g (6.99 mmol), corresponding to 78.1% of theory.

c) Synthesis of Compound (XXIV)

The synthesis of compound (XXIV) is carried out analogously to that of compound (XVIII), with compound (XII) being replaced by 4.20 g (6.59 mmol) of compound (XXII). The yield is 4.03 g (5.48 mmol), corresponding to 83.2% of theory.

Example 5

Production and Characterisation of Fluorescent Organic Electroluminescent Devices Comprising the Compounds According to the Invention The structures of SEB-1 (synthesised in accordance with WO 08/006,449) and ETM-1 (WO 2005/053055) are depicted below for the sake of clarity.

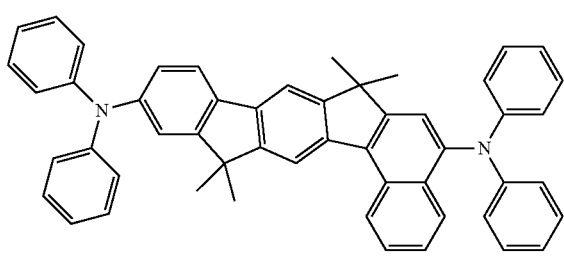
SEB-1

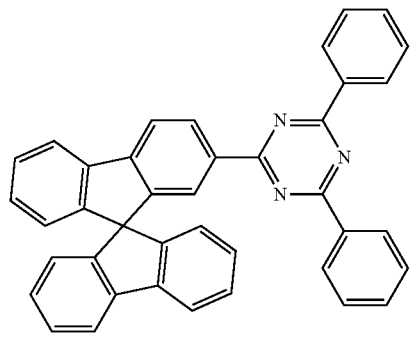
ETM-1

The materials according to the invention can be used from solution, where they result in simple devices having nevertheless very good properties. The devices described are produced using techniques which are very well known to the person skilled in the art in the area. The production of such components is based on the production of polymeric light-emitting diodes (PLEDs), which has already been described many times in the literature (for example in WO 2004/037887). In the present case, compounds (X) and (XVIII) according to the invention or the likewise soluble comparative compounds (XX) and (XXIV) are dissolved in toluene. The emitter proportion is 5% by weight. The typical solids content of such solutions is 15 g/l.

The structure of the device is as follows: cathode (Al 100 nm)/ETL (20 nm)/EML (50 nm)/interlayer (20 nm)/buffer layer (PEDOT:PSS, 20 nm)/anode, where ETL is the electron-transport layer, which comprises 20% by weight of compound ETM-1 and 80% by weight of Liq, and EML represents the emitting layer. The emitting layer comprises 95% by weight of the host material according to the invention and 5% by weight of emitter SEB-1. Structured ITO substrates (Technoprint) and the material for the so-called buffer layer (PEDOT:PSS) (as Clevios Baytron P aqueous dispersion from H.C. Starck) are commercially available. The interlayer used serves for hole injection; in this case, HIL-012 from Merck KGaA is used. The emission layer is applied by spin coating in an inert-gas atmosphere, in the present case argon, and dried by heating at 120° C. for 10 min. Finally, an aluminium cathode is applied by vacuum vapour deposition. A hole-blocking layer and/or an electron-transport layer can also be applied between the emitting layer and the cathode by vapour deposition, and the interlayer can also be replaced by one or more layers, which merely have to satisfy the condition of not being detached again by the subsequent processing step of deposition of the emitting layer from solution.

The devices are characterised as standard by means of methods which are well known to the person skilled in the art. The OLED examples given have not yet been optimised. Table 1 summarises the data obtained. In the case of the processed devices, it is apparent that the materials according to the invention are superior to those previously available in terms of efficiency and/or lifetime.

TABLE 1

Results with solution-processed materials according to the invention in the device configuration described (Ba/Al)/EML/interlayer/buffer layer/ITO.

| Ex. | EML 50 nm | Max. eff. [cd/A] | Voltage [V] at 1000 cd/m$^2$ | CIE (x, y) | Lifetime [h], initial luminance 1000 cd/m$^2$ |
|---|---|---|---|---|---|
| 3 comp. | (XX): SEB-1 | 4.5 | 4.9 | 0.14, 0.18 | 300 |
| 1 | (X): SEB-1 | 5.9 | 4.8 | 0.14, 0.18 | 500 |
| 4 comp. | (XXIV): SEB-1 | 4.4 | 4.8 | 0.14, 0.18 | 350 |
| 2 | (XVIII): SEB-1 | 6.1 | 4.8 | 0.14, 0.18 | 600 |

Example 6

Preparation of Compound (XXVI)

Synthetic Procedure for the Preparation of Compound (XXVI)

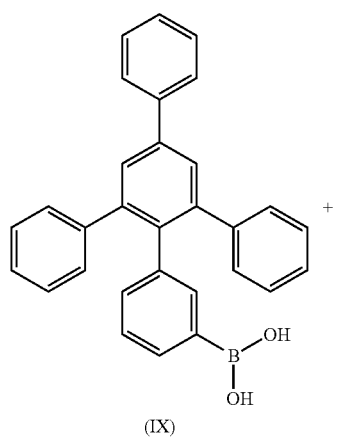

(IX)

+

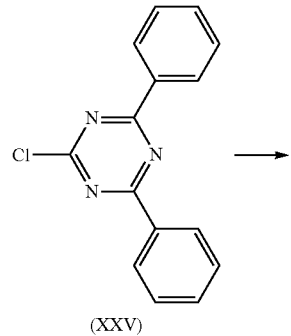

(XXV)

→

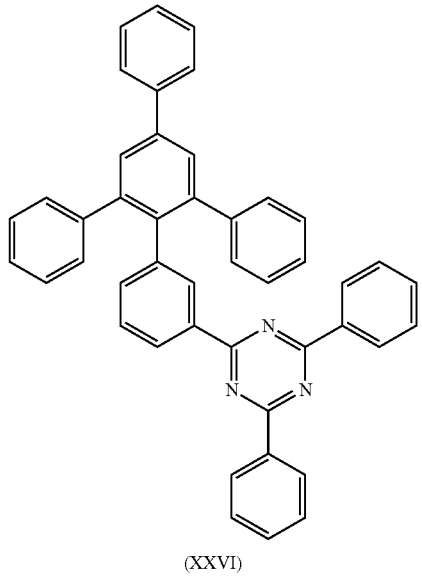

(XXVI)

10.0 g (20 mmol) of 4,4,5,5-tetramethyl-2-(3-(2,4,6-triphenyl)phenyl)phenyl-1,3,2-dioxaborolane and 500 ml of toluene are added to a solution of 33.0 g (310 mol) of sodium carbonate in dist. water (3 ml). One drop of Aliquat, 5.0 g of compound (XXV) (19 mmol) and subsequently 0.2 g of tetrakis(triphenylphosphine)palladium (0.2 mmol) is to the reaction mixture. The reaction mixture is stirred at 90° C. for two days. After addition of 150 ml of dichloromethane, the organic phase is washed with a sodium chloride solution (sat.), dried over magnesium sulfate and subsequently evaporated to dryness. The residue is purified by column chromatography over silica gel (CH:DCM=4:1). The product is subsequently dissolved in dichloromethane and precipitated from methanol. The colourless solid is dissolved in boiling toluene and re-precipitated by addition of n-pentane. The yield is 5.0 g (8 mmol), corresponding to 41.0% of theory.

Example 7

Comparative Example

Preparation of Compounds (XXVII) to (XXIX)

Synthetic Procedure for the Preparation of Compound (XXIX)

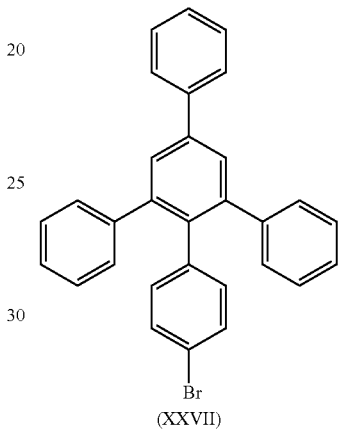

(XXVII)

↓

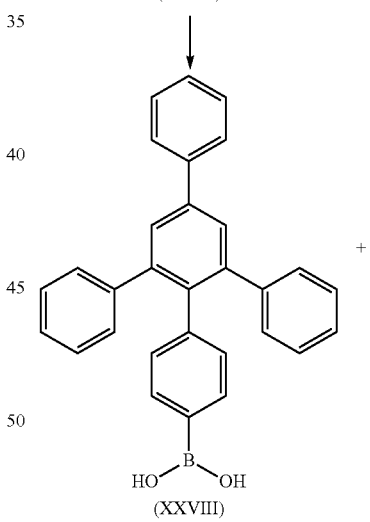

(XXVIII)

+

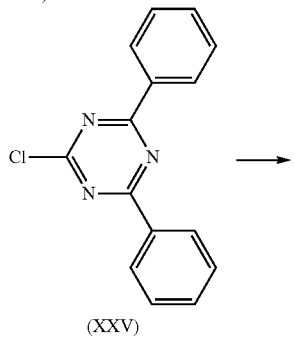

(XXV)

→

-continued

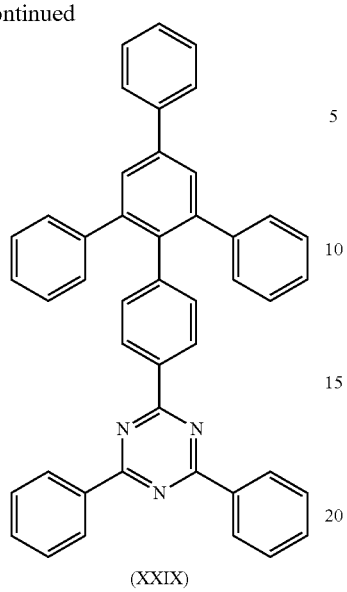

(XXIX)

a) Synthesis of Compound (XXVII)

The synthesis of compound (XXVII) is carried out analogously to that of compound (VIII), with the 3-bromophenylacetic acid being replaced by 42.2 g (195 mmol) of 4-bromophenylacetic acid. The yield is 23.2 g (50.2 mmol), corresponding to 50.9% of theory.

b) Synthesis of Compound (XXVIII)

The synthesis of compound (XXVIII) is carried out analogously to that of compound (IX), with compound (VIII) being replaced by 20.0 g (43.4 mmol) by compound (XXVII). The yield is 14.20 g (33.2 mmol), corresponding to 76.2% of theory.

c) Synthesis of Compound (XXIX)

The synthesis of compound (XXIX) is carried out analogously to that of compound (XXVI), with compound (IX) being replaced by 12.0 g (45.5 mmol) of compound (XXVIII). The yield is 12.1 g (19.1 mmol), corresponding to 42.0% of theory.

Example 8

Production and Characterisation of Phosphorescent Organic Electroluminescent Devices Comprising the Compounds According to the Invention The structures of emitter TEG-1 (synthesised in accordance with WO 2004/085449) and co-host C1 (in accordance with WO 2009/124627) are depicted below for the sake of clarity.

TEG-1

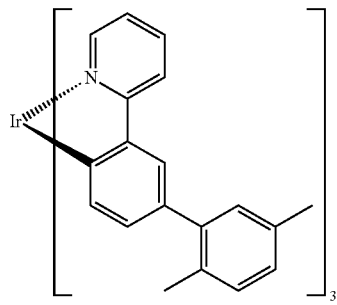

C1

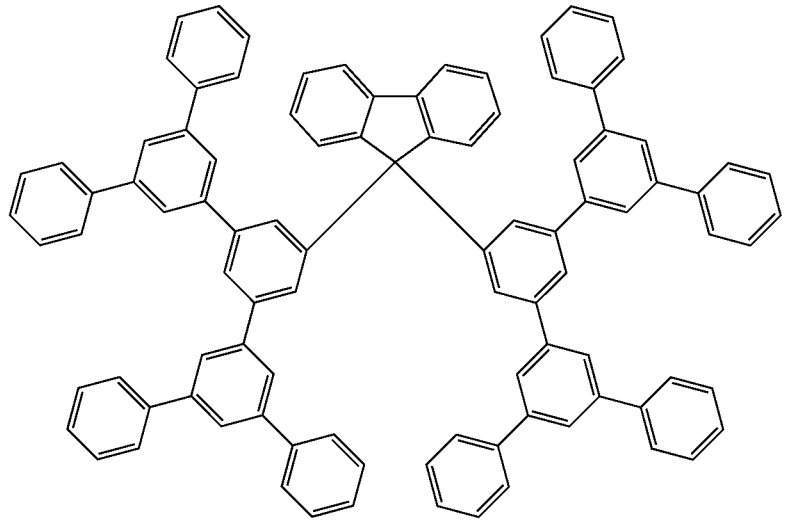

The materials according to the invention can be used from solution, where they result in simple devices having nevertheless very good properties. The devices described are produced using techniques which are very well known to the person skilled in the art in the area. The production of such components is based on the production of polymeric light-emitting diodes (PLEDs), which has already been described many times in the literature (for example in WO 2004/037887). In the present case, the compounds according to the invention (for example the compound of the formula (XXVI)) or the likewise soluble comparative compounds (XXIX) are dissolved in toluene. The typical solids content of such solutions is between 16 and 25 g/l, if, as here, the typical layer thickness of 80 nm for a device is to be achieved by means of spin coating. The structure of the device is as follows: cathode (Ba/Al:3 nm/150 nm)/EML (80 nm)/interlayer (20 nm)/buffer layer (PEDOT:PSS, 80 nm)/anode, where EML represents the emitting layer, which, in the present case, comprises either 83% by weight of the matrix material (XXVI or XXIX) or 41.5% by weight of the matrix material (XXVI or XXIX) and 41.5% by weight of co-host C1, and 17% by weight of the emitter. Structured ITO substrates (Technoprint) and the material for the so-called buffer layer (PEDOT:PSS) (as Clevios Baytron P aqueous dispersion from H.C. Starck) are commercially available. The interlayer used serves for hole injection; in this case, HIL-012 from Merck KGaA is used. The emission layer is applied by spin coating in an inert-gas atmosphere, in the present case argon, and dried by heating at 120° C. for 10 min. Finally, a barium and aluminium cathode is applied by vacuum vapour deposition. A hole-blocking layer and/or an electron-transport layer can also be applied between the emitting layer and the cathode by vapour deposition, and the interlayer can also be replaced by one or more layers, which merely have to satisfy the condition of not being detached again by the subsequent processing step of deposition of the emitting layer from solution.

The devices are characterised as standard by means of methods which are well known to the person skilled in the art. The OLED examples given have not yet been optimised. Table 2 summarises the data obtained. In the case of the processed devices, it is apparent that the materials according to the invention are superior to those previously available in terms of efficiency and/or lifetime.

TABLE 2

Results with solution-processed materials according to the invention in the phosphorescent device configuration described (Ba/Al)/EML/interlayer/buffer layer/ITO.

| Ex. | EML 80 nm | Max. eff. [cd/A] | Voltage [V] at 1000 cd/m² | CIE (x, y) | Lifetime [h], initial luminance 1000 cd/m² |
|---|---|---|---|---|---|
| 7 comp. | (XXIX): TEG-1 | 12 | 4.7 | 0.33/0.63 | 8000 |
| 6 | (XXVI): TEG-1 | 20 | 4.6 | 0.33/0.63 | 18000 |
| 7 comp. | (XXIX): C1: TEG-1 | 15 | 4.6 | 0.33/0.63 | 12000 |
| 6 | (XXVI): C1: TEG-1 | 34 | 4.6 | 0.33/0.63 | 37000 |

The invention claimed is:

1. A compound of the formula (2)

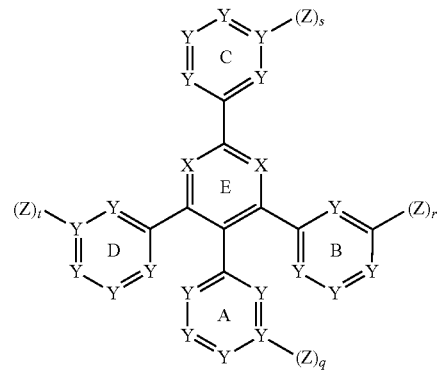

formula (2)

where the following applies to the symbols and indices used:

X is on each occurrence;

Y is $CR^1$;

$R^1$ is, identically or differently on each occurrence, H, D, F, Cl, Br, I, $N(R^2)_2$, CN, $NO_2$, $Si(R^2)_3$, $B(OR^2)_2$, C(=O)$R^2$, P(=O)$(R^2)_2$, S(=O)$R^2$, S(=O)$_2R^2$, $OSO_2R^2$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^2$, where one or more non-adjacent $CH_2$ groups is optionally replaced by $R^2C=CR^2$, C≡C, $Si(R^2)_2$, $Ge(R^2)_2$, $Sn(R^2)_2$, C=O, C=S, C=Se, C=$NR^2$, P(=O)$(R^2)$, SO, $SO_2$, $NR^2$, O, S or $CONR^2$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy, arylalkoxy or heteroaryloxy group having 5 to 60 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals $R^2$, or a combination of two or more of these groups or a crosslinkable group Q;

$R^2$ is, identically or differently on each occurrence, H, D, F, Cl, Br, I, $N(R^3)_2$, CN, $NO_2$, $Si(R^3)_3$, $B(OR^3)_2$, C(=O)$R^3$, P(=O)$(R^3)_2$, S(=O)$R^3$, S(=O)$_2R^3$, $OSO_2R^3$, a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals $R^3$, where one or more non-adjacent $CH_2$ groups is optionally replaced by $R^3C=CR^3$, C≡C, $Si(R^3)_2$, $Ge(R^3)_2$, $Sn(R^3)_2$, C=O, C=S, C=Se, C=$NR^3$, P(=O)$(R^3)$, SO, $SO_2$, $NR^3$, O, S or $CONR^3$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy, arylalkoxy or heteroaryloxy group having 5 to 60 aromatic ring atoms, which is optionally substituted by one or more radicals R³, or a diarylamino group, diheteroarylamino group or arylheteroarylamino group having 10 to 40 aromatic ring atoms, which is optionally substituted by one or more radicals R³, or a combination of two or more of these groups; two or more adjacent radicals R² here may form a mono- or polycyclic, aliphatic or aromatic ring system with one another;

R³ is, identically or differently on each occurrence, H, D, F or an aliphatic, aromatic and/or heteroaromatic hydrocarbon radical having 1 to 20 C atoms, in which, in addition, one or more H atoms is optionally replaced by F; two or more substituents R³ here may also form a mono- or polycyclic, aliphatic or aromatic ring system with one another; and Z is on each occurrence, identically or differently, R¹, with the proviso that at least one of the radicals Z must be an aromatic or heteroaromatic group having 5 to 60 aromatic ring atoms; and q, r, s and t is, independently of one another, either 0 or 1 and u=q+r+s+t=1, 2, 3 or 4.

2. The compound according to claim 1, wherein the compound has the formula (18)

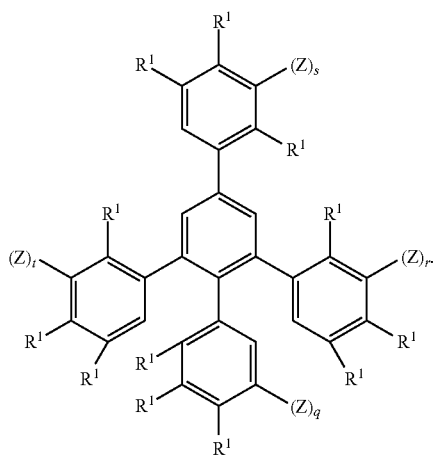

formula (18)

3. The compound according to claim 1, wherein the compound has the formula (20)

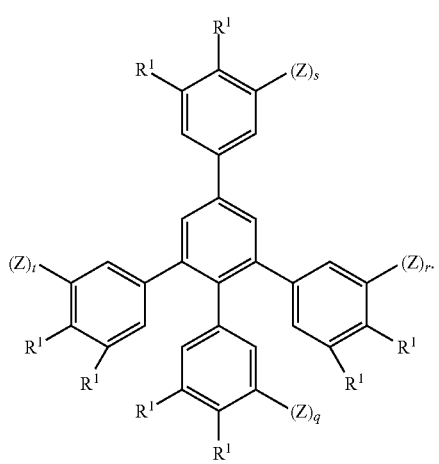

formula (20)

4. The compound according to claim 1, wherein Z, identically or differently on each occurrence, H, D, F, Cl, Br, I, N(R²)₂, CN, NO₂, Si(R²)₃, B(OR²)₂, C(=O)R², P(=O)(R²)₂, S(=O)R², S(=O)₂R², OSO₂R², a straight-chain alkyl, alkoxy or thioalkoxy group having 1 to 40 C atoms or a straight-chain alkenyl or alkynyl group having 2 to 40 C atoms or a branched or cyclic alkyl, alkenyl, alkynyl, alkoxy, alkylalkoxy or thioalkoxy group having 3 to 40 C atoms, each of which is optionally substituted by one or more radicals R², where one or more non-adjacent CH₂ groups is optionally replaced by R²C=CR², Si(R²)₂, Ge(R²)₂, Sn(R²)₂, C=O, C=S, C=Se, C=NR², P(=O)(R²), SO, SO₂, NR², O, S or CONR² and where one or more H atoms is optionally replaced by D, F, Cl, Br, I, CN or NO₂, or an aromatic or heteroaromatic ring system having 5 to 60 aromatic ring atoms, which may in each case be substituted by one or more radicals R², or an aryloxy, arylalkoxy or heteroaryloxy group having 5 to 60 aromatic ring atoms, which is optionally substituted by one or more radicals R², or a diarylamino group, diheteroarylamino group or arylheteroarylamino group having 10 to 40 aromatic ring atoms, which is optionally substituted by one or more radicals R², or a combination of two or more of these groups, with the proviso that at least one of the radicals Z occurring must be an aromatic or heteroaromatic group having 5 to 60 aromatic ring atoms.

5. The compound according to claim 1, wherein Z is, identically or independently of one another on each occurrence, an aromatic or heteroaromatic group having 5 to 60 aromatic ring atoms, where the group of the aromatic and heteroaromatic groups having 5 to 60 ring atoms also include condensed aromatic and heteroaromatic ring systems.

6. The compound according to claim 1, wherein Z is selected from the group of the radicals having the following formulae (66) to (80)

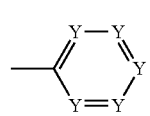

formula (66)

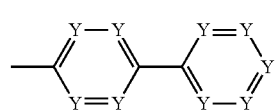

formula (67)

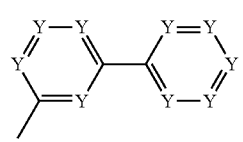

formula (68)

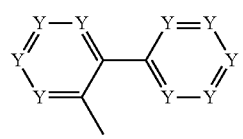

formula (69)

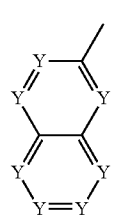

formula (70)

formula (71)

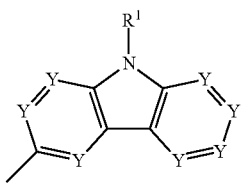

formula (72)

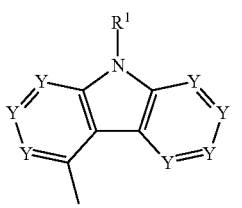

formula (73)

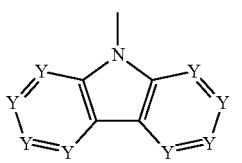

formula (74)

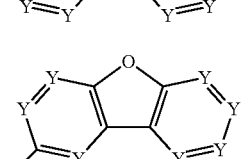

formula (75)

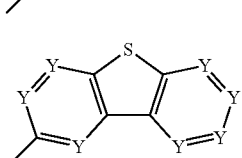

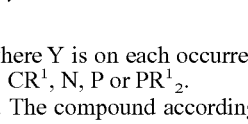

formula (76)

formula (77)

formula (78)

formula (79)

formula (80)

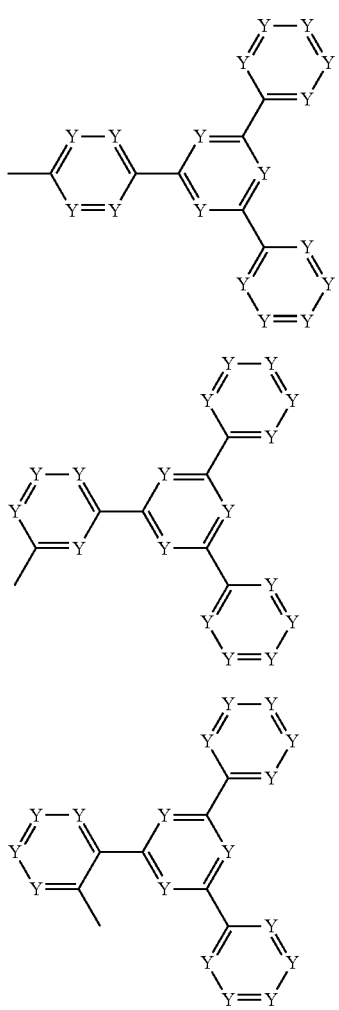

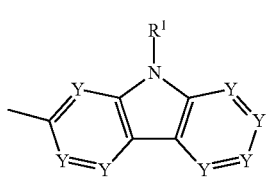

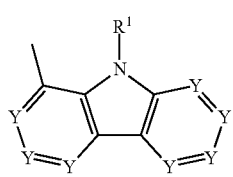

where Y is on each occurrence, identically or differently, $CR^1$, N, P or $PR^1_2$.

7. The compound according to claim 6, wherein Y is on each occurrence, identically or differently, $CR^1$ or N.

8. A formulation comprising at least one compound according to claim 1 and at least one solvent.

9. A composition comprising at least one of the compounds according to claim 1 and at least one further organically functional material selected from the group consisting of the emitters, host materials, matrix materials, electron-transport materials (ETM), electron-injection materials (EIM), hole-transport materials (HTM), hole-injection materials (HIM), electron-blocking materials (EBM), hole-blocking materials (HBM) and exciton-blocking materials (ExBM).

10. A composition comprising at least one of the compounds according to claim 1 and at least one further organically functional material selected from the group consisting of fluorescent and phosphorescent emitters.

11. A process for the therapy and/or diagnosis of diseases and/or cosmetic conditions which comprises utilizing the compound according to claim 1.

* * * * *

UNITED STATES PATENT AND TRADEMARK OFFICE
CERTIFICATE OF CORRECTION

PATENT NO.         : 8,906,893 B2  
APPLICATION NO.    : 13/991919  
DATED              : December 9, 2014  
INVENTOR(S)        : Rémi M. Anémian et al.

Page 1 of 1

It is certified that error appears in the above-identified patent and that said Letters Patent is hereby corrected as shown below:

In the Claims:

In claim 1, column 146, line 24, "X is on each occurrence;" should read -- X is on each occurrence CH; --.

Signed and Sealed this  
Twenty-first Day of July, 2015

Michelle K. Lee  
*Director of the United States Patent and Trademark Office*